US007960408B2

(12) United States Patent
McGee et al.

(10) Patent No.: US 7,960,408 B2
(45) Date of Patent: *Jun. 14, 2011

(54) QUINOLINYL AND BENZOTHIAZOLYL MODULATORS

(75) Inventors: Lawrence R. McGee, Pacifica, CA (US); Jonathan B. Houze, San Mateo, CA (US); Steven M. Rubenstein, Pacifica, CA (US); Atsushi Hagiwara, Osaka (JP); Noboru Furukawa, Osaka (JP); Hisashi Shinkai, Osaka (JP)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/372,699

(22) Filed: Feb. 17, 2009

(65) Prior Publication Data

US 2009/0221635 A1    Sep. 3, 2009

Related U.S. Application Data

(63) Continuation of application No. 10/719,997, filed on Nov. 20, 2003, now Pat. No. 7,601,841, which is a continuation of application No. 10/278,851, filed on Oct. 21, 2002, now abandoned, which is a continuation of application No. 09/894,980, filed on Jun. 27, 2001, now Pat. No. 6,583,157.

(60) Provisional application No. 60/214,810, filed on Jun. 28, 2000.

(51) Int. Cl.
    *A61K 31/04*     (2006.01)
(52) U.S. Cl. ........................................ 514/311; 514/312
(58) Field of Classification Search .................. 514/311, 514/312
    See application file for complete search history.

(56) References Cited

U.S. PATENT DOCUMENTS

| 2,407,309 | A | 9/1946 | Lott et al. |
|---|---|---|---|
| 3,033,870 | A | 5/1962 | Druey et al. |
| 3,034,955 | A | 5/1962 | Frick et al. |
| 3,174,901 | A | 3/1965 | Sterne |
| 3,669,966 | A | 6/1972 | Ambrogi et al. |
| 3,674,843 | A | 7/1972 | Shen et al. |
| 3,686,192 | A | 8/1972 | Moore et al. |
| 4,003,734 | A | 1/1977 | Johnston |
| 4,013,621 | A | 3/1977 | Knell |
| 4,061,642 | A | 12/1977 | Fleckenstein et al. |
| 4,062,950 | A | 12/1977 | Frommer et al. |
| 4,218,237 | A | 8/1980 | Nishiyama et al. |
| 4,248,619 | A | 2/1981 | Serban et al. |
| 4,289,876 | A | 9/1981 | Algieri et al. |
| 4,499,304 | A | 2/1985 | Gabrielsen et al. |
| 4,549,901 | A | 10/1985 | James |
| 4,565,568 | A | 1/1986 | Johnston et al. |
| 4,572,912 | A | 2/1986 | Yoshioka et al. |
| 4,577,028 | A | 3/1986 | Martin et al. |
| 4,670,045 | A | 6/1987 | Ehr et al. |
| 4,731,090 | A | 3/1988 | Boger et al. |
| 4,756,739 | A | 7/1988 | Fuss et al. |
| 4,851,419 | A | 7/1989 | Cox |
| 4,866,079 | A | 9/1989 | Boger et al. |
| 4,900,751 | A | 2/1990 | Cox |
| 4,946,854 | A | 8/1990 | Maienfisch et al. |
| 4,952,235 | A | 8/1990 | Andree et al. |
| 4,987,141 | A | 1/1991 | Bushell et al. |
| 5,008,276 | A | 4/1991 | Clough et al. |
| 5,070,096 | A | 12/1991 | Mohrs et al. |
| 5,081,125 | A | 1/1992 | Maienfisch et al. |
| 5,093,340 | A | 3/1992 | Mohrs et al. |
| 5,143,937 | A | 9/1992 | Lang et al. |
| 5,151,428 | A | 9/1992 | Sakamoto et al. |
| 5,202,336 | A | 4/1993 | Mohrs et al. |
| 5,204,354 | A | 4/1993 | Chakravarty et al. |
| 5,250,549 | A | 10/1993 | Yoshino et al. |
| 5,304,532 | A | 4/1994 | Munro et al. |
| 5,360,810 | A | 11/1994 | Hayase et al. |
| 5,444,036 | A | 8/1995 | Iwasaki et al. |
| 5,514,696 | A | 5/1996 | Murugesan et al. |
| 5,545,669 | A | 8/1996 | Adams et al. |
| 5,610,320 | A | 3/1997 | Yoshino et al. |
| 5,624,937 | A | 4/1997 | Reel |
| 5,643,914 | A | 7/1997 | Daines |
| 5,684,195 | A | 11/1997 | Huang et al. |
| 5,716,993 | A | 2/1998 | Ozaki et al. |
| 5,780,483 | A | 7/1998 | Widdowson et al. |
| 5,814,646 | A | 9/1998 | Heinz |
| 5,880,136 | A | 3/1999 | Duggan et al. |
| 5,990,126 | A | 11/1999 | Park |
| 6,022,897 | A | 2/2000 | Evans et al. |
| 6,028,052 | A | 2/2000 | Heyman et al. |
| 6,200,995 | B1 | 3/2001 | De la Brouse-Elwood et al. |

(Continued)

FOREIGN PATENT DOCUMENTS

| CH | 592 411 | 10/1977 |
|---|---|---|
| DE | 3632329 A1 | 3/1988 |
| EP | 069585 A1 | 1/1983 |
| EP | 0148730 A2 | 7/1985 |
| EP | 0261539 A2 | 3/1988 |
| EP | 0306222 | 3/1989 |
| EP | 0749751 A2 | 12/1996 |
| EP | 0778267 A1 | 6/1997 |
| EP | 0472053 | 6/1998 |
| EP | 0855391 A1 | 7/1998 |

(Continued)

OTHER PUBLICATIONS

Clark, J Leukocyte Biololgy, vol. 71, Mar. 2002. pp. 388-400.*
Berger, J of Biological Chemistry, vol. 274, No. 10, Mar. 1999, pp. 6718-6725.*
http:/www.en.wikipedia.org/wiki/Biguanide (2007).

(Continued)

*Primary Examiner* — D. Margaret Seaman
(74) *Attorney, Agent, or Firm* — Jones Day

(57) ABSTRACT

Compounds, compositions and methods are provided that are useful in the treatment or prevention of a condition or disorder mediated by PPARγ. In particular, the compounds of the invention modulate the function of PPARγ. The subject methods are particularly useful in the treatment and/or prevention of diabetes, obesity, hypercholesterolemia, rheumatoid arthritis and atherosclerosis.

16 Claims, No Drawings

U.S. PATENT DOCUMENTS

| | | | |
|---|---|---|---|
| 6,214,850 B1 | 4/2001 | Evans et al. |
| 6,262,112 B1 | 7/2001 | Mittendorf et al. |
| 6,294,559 B1 | 9/2001 | Smith |
| 6,348,474 B1 | 2/2002 | Kayakiri et al. |
| 6,353,011 B1 | 3/2002 | Pershadsingh et al. |
| 6,369,075 B1 | 4/2002 | Ruggeri et al. |
| 6,376,512 B1 | 4/2002 | Jayyosi et al. |
| 6,403,607 B1 | 6/2002 | Hidaka et al. |
| 6,469,054 B1 | 10/2002 | Mittendorf et al. |
| 6,472,779 B2 | 10/2002 | Hwang et al. |
| 6,545,050 B1 | 4/2003 | Mittendorf et al. |
| 6,573,278 B2 | 6/2003 | Mittendorf et al. |
| 6,583,157 B2 | 6/2003 | McGee et al. |
| 6,586,475 B1 | 7/2003 | Kato et al. |
| 6,620,827 B2 | 9/2003 | De la Brouse-Elwood et al. |
| 6,653,309 B1 | 11/2003 | Saunders et al. |
| 6,653,332 B2 | 11/2003 | Jaen et al. |
| 6,677,488 B2 | 1/2004 | Reitz et al. |
| 6,770,648 B2 | 8/2004 | McGee et al. |
| 7,041,691 B1 | 5/2006 | McGee et al. |
| 7,132,546 B2 | 11/2006 | Kato et al. |
| 7,223,761 B2 | 5/2007 | Kruk et al. |
| 7,439,242 B2 | 10/2008 | Houze et al. |
| 7,601,841 B2 * | 10/2009 | McGee et al. ............. 546/153 |
| 7,626,033 B2 | 12/2009 | McGee et al. |
| 2001/0028200 A1 | 10/2001 | Hwang et al. |
| 2003/0088103 A1 | 5/2003 | Houze et al. |
| 2003/0171399 A1 | 9/2003 | McGee et al. |
| 2004/0048891 A1 | 3/2004 | Kato et al. |
| 2004/0176409 A1 | 9/2004 | McGee et al. |
| 2004/0248882 A1 | 12/2004 | McGee et al. |
| 2004/0259918 A1 | 12/2004 | Jaen et al. |

FOREIGN PATENT DOCUMENTS

| | | |
|---|---|---|
| GB | 2373725 | 10/2002 |
| JP | 64-6245 | 1/1989 |
| JP | 9-255656 | 9/1997 |
| JP | 55-79369 | 6/2002 |
| WO | WO 95/01326 A | 1/1995 |
| WO | WO 95/33461 | 12/1995 |
| WO | WO 95/33462 | 12/1995 |
| WO | WO 96/09294 | 3/1996 |
| WO | WO 96/15118 | 5/1996 |
| WO | WO 97/00857 | 1/1997 |
| WO | WO 97/30677 | 8/1997 |
| WO | WO 97/31907 | 9/1997 |
| WO | WO 97/36579 | 10/1997 |
| WO | WO 98/02437 | 1/1998 |
| WO | WO 98/16503 | 4/1998 |
| WO | WO 98/27081 | 6/1998 |
| WO | WO 98/37061 | 8/1998 |
| WO | WO 98/50029 | 11/1998 |
| WO | WO 98/50030 | 11/1998 |
| WO | WO 99/00372 | 1/1999 |
| WO | WO 99/06378 | 2/1999 |
| WO | WO 99/10320 | 3/1999 |
| WO | WO 99/20275 | 4/1999 |
| WO | WO 99/24404 | 5/1999 |
| WO | WO 99/32465 | 7/1999 |
| WO | WO 99/38845 | 8/1999 |
| WO | WO 99/50237 | 10/1999 |
| WO | WO 99/55663 | 11/1999 |
| WO | WO 00/10967 | 3/2000 |
| WO | WO 00/12073 | 3/2000 |
| WO | WO 00/12623 | 3/2000 |
| WO | WO 00/17202 | 3/2000 |
| WO | WO 00/31021 | 6/2000 |
| WO | WO 00/10968 | 11/2000 |
| WO | WO 01/00579 | 1/2001 |
| WO | WO 01/30343 | 5/2001 |
| WO | WO 01/60807 | 8/2001 |
| WO | WO 01/70723 | 9/2001 |
| WO | WO 01/82916 | 11/2001 |
| WO | WO 01/83427 | 11/2001 |
| WO | WO 01/87860 | 11/2001 |
| WO | WO 01/87861 | 11/2001 |
| WO | WO 01/87862 | 11/2001 |
| WO | WO 01/95906 | 12/2001 |
| WO | WO 02/00611 | 1/2002 |
| WO | WO 02/00633 A1 | 1/2002 |
| WO | WO 02/08188 | 1/2002 |
| WO | WO 02/13812 | 2/2002 |
| WO | WO 02/13864 | 2/2002 |
| WO | WO 02/14291 | 2/2002 |
| WO | WO 02/17901 | 3/2002 |
| WO | WO 02/18355 | 3/2002 |
| WO | WO 02/26729 | 4/2002 |
| WO | WO 02/26737 | 4/2002 |
| WO | WO 02/28832 | 4/2002 |
| WO | WO 02/28857 | 4/2002 |
| WO | WO 02/30860 | 4/2002 |
| WO | WO 02/30863 | 4/2002 |
| WO | WO 02/30884 | 4/2002 |
| WO | WO 02/30895 | 4/2002 |
| WO | WO 02/40020 | 5/2002 |
| WO | WO 02/46161 | 6/2002 |
| WO | WO 02/49626 | 6/2002 |
| WO | WO 02/051397 | 7/2002 |
| WO | WO 02/051820 | 7/2002 |
| WO | WO 02/053546 | 7/2002 |
| WO | WO 02/059098 | 8/2002 |
| WO | WO 02/060434 | 8/2002 |
| WO | WO 02/062772 | 8/2002 |
| WO | WO 02/062774 | 8/2002 |
| WO | WO 02/062798 | 8/2002 |
| WO | WO 02/062799 | 8/2002 |
| WO | WO 02/064094 | 8/2002 |
| WO | WO 02/066028 | 8/2002 |
| WO | WO 02/072003 | 9/2002 |
| WO | WO 02/074291 | 9/2002 |
| WO | WO 02/080913 | 10/2002 |
| WO | WO 02/081454 | 10/2002 |
| WO | WO 02/090882 | 11/2002 |
| WO | WO 02/092084 | 11/2002 |
| WO | WO 02/092590 | 11/2002 |
| WO | WO 2005/033074 A2 | 4/2005 |

OTHER PUBLICATIONS http://www.en.wikipedia.org/wiki/Troglitazone (2007).

Adams, B. et al., "Quinone Imides. XXV. Addition of Mercaptans to p-Quinonedibenzenesulfonimide," The Notes Chemical Laboratory, University of Illinois, Feb. 5, 1953, vol. 2:663-665 (1953).

Badilescu, I., Chemical Abstracts., vol. 67(9), Aug. 28, 1967, Columbus, OH, US; Abstract No. 43516y, p. 4076; XP002099084; "Synthesis of Some N-aryl- and N,N-dialkyl-p-chloro-benzensulfonamides," Rev.Chim., vol. 17(11):705-706 (1966).

Baguley et al., Database Accession No. 108:179602, Database Chemabs 'Online!, RN 106831-10-1 CAPLUS, Eur. J. Cancer Clin. Oncol., vol. 24(2):205-210 (1988).

Burmistrov et al., Database Accession No. 115:8165, Database Chemabs 'Online!, RNs 98187-76-9 CAPLUS, 134284-4-5 CAPLUS, Ah., Org. Khim, vol. 26(9):1995-1998 (1990).

Burmistrov et al., Database Accession No. 122:132338, Database Chemabs 'Online!, RN 134284-40-5 CAPLUS, Zh. Org. Khim, vol. 30(5):744-747 (1994).

Cain et al., "Potential Antitumor Agents. 14. Acridylmethanesulfonanilides," J. Med. Chem., vol. 17(9):922-930 (1974).

Chaturvedi et al., "Antibacterial Studies of 7-(α-substituted sulfonamide)methyl- and 7-(α-substituted sulfonamide)phenyl-8-hydroxyquinolines," Journal of the Indian Chemical Society, vol. 61(2):175-176 (1984) (Abstract Chem. Abstract Accession No. 101:87311).

Collins et al., "N-(2-Benzoylphenyl)-L-tyrosine PPARγ Agonists. 2. Structure-Activity Relationship and Optimization of the Phenyl Alkyl Ether Moiety," J. Med. Chem., vol. 41(25):5037-5054 (1998).

Denny et al., Database Accession No. 96:79437, Database Chemabs 'Online!, RNs 80260-24-8 CAPLUS, 80260-260 CAPLUS, J. Med. Chem., vol. 25(3):276-315 (1982).

Dumas, Chemical Abstracts 131:336969, Abstract of Bioorg. Med. Chem. Legg., vol. 9(17)2531-2536 (1999).

Foreman et al., "15-Deoxy-Δ12-14-Prostagladin J2 is a Ligand for the Adipocyte Determination Factor PPARγ," Cell, vol. 83:803-812 (1995).

Jiang et al., "PPAR-γ Agonists Inhibit Production of Monocyte Inflammatory Cytokines," Nature, vol. 391:82-86 (1998).

Lehmann et al., "Peroxisome Proliferator-Activated Receptors α and γ Are Activated by Indomethacin and Other Non-Steroidal Anti-Inflammatory Drugs," The Journal of biological Chemistry, vol. 272(6):3406-3410 (1997).

Lehman et al., "An Antidiabetic Thiazolidinedione is a High Affinity Ligand for Peroxisome Proliferator-Activated Receptor γ (PPARγ)," J. Biol. Chem., vol. 270(22):12953-12956 (1995).

Merck Index, The, 10$^{th}$ Ed., Windholz et al., eds. Merck & Co. Inc., Rahway, N.J., pp. 849-850, Abstract 5792 (1983).

Misra, V., "Synthesis of new Substituted Quinoline & Study of Their Effect on the Tobacco Mosaic Virus," Indian Journal of Chemistry, Section B: Organic Chemistry Including Medicinal Chemistry, vol. 18B(3):262-264 (1979).

Mysyk et al., Database Accession No. 92:163637, Database Chemabs 'Online!, RN 73320-75-9 CAPLUS, Zh. Org. Khim, vol. 15(12): 2499-2502 (1979).

Pieper et al., Database Accession No. 112:138679, Database Chemabs 'Online!, RN 101513-48-8 CAPLUS, Arzneim.-Forsch, vol. 39(9):1073-1080 (1989).

Ricote et al., "The Peroxisome Proliferator-Activated Receptor-γ is a Negative Regulator of macrophage Activation," Nature, vol. 391:79-82 (1998).

Sarul et al., Database Accession No. 103:123106, Database Chemabs 'Online!, RN 98187-77-0 CAPLUS, Latv. Psr Ainat. Akad. Vestis, Kim. Ser., vol. 2:225-228 (1985).

Sebe et al., Database Accession No. 117:214517, Database Chemabs 'Online!, RNs 144206-02-0 CAPLUS, 144232-65-5 CAPLUS, Rev. Chim, vol. 43(5-6):222-225 (1992).

Shah et al., "Ouinaldine Sulphonamide Derivatives," Journal of the Institution of Chemists, vol. 59(6):257-258 (1987).

Spiegelman, B.M., "PPAR-γ: Adipogenic Regulator and Thiazolidinedione Receptor," Diabetes, vol. 47:507-514 (1998).

Willson et al., "The PPARs: From Orphan Receptors to Drug Discovery," Journal of Medicinal Chemistry, vol. 43(4):527-550 (2000).

Willson et al., "The Structure-Activity Relationship Between Peroxisome Proliferator-Activated Receptor γ Agonism and the Antohyperglycemic Activity of Thiazolidinediones," J. Med. Chem., vol. 39:665-668 (1996).

Wollweber et al., Database Accession No. 101:151540, Database Chemabs 'Online!, RN 92114-63-1 CAPLUS, Arzneim.-Forsch., vol. 34(5):531-542(1984).

Zaitseva et al., Database Accession No. 86:43377, Database Chemabs 'Online!, RN 61381-98-4 CAPLUS, Zh. Org. Khim, vol. 12(9):1987-1992 (1976).

ISA/EP International Search Report, dated May 16, 2002, for International Application No. PCT/US2001/14393, filed May 2, 2001.

IPEA/EP International Preliminary Examination Report, dated Nov. 13, 2002, for International Application No. PCT/US2001/14393.

ISA/EP International Search Report, dated May 7, 1999, for International Application No. PCT/US1999/01147, filed Jan. 20, 1999.

ISA/EP International Written Opinion, dated Oct. 8, 1999, for International Application No. PCT/US1999/01147, filed Jan. 20, 1999.

IPEA/RU Examination Report dated Mar. 14, 2005, for Application No. 2002/02750.

AU—Australian Patent Office Examination Report dated Jul. 8, 2003, for Application No. 60643/00.

AU—Australian patent office Examination Report dated Jul. 27, 2004, for Application No. 60643/00.

CN—Intellectual Property Office of the People's Republic of China, Office action dated Feb. 20, 2004, for Application No. 01812017.2, filed Jun. 27, 2001.

EPO—European Official Action dated Oct. 8, 2007, in EP Patent Application No. 00 946 961.0-2101.

IPOS—Intellectual Property Office of Singapore, Examination Report dated Oct. 4, 2007, for Singapore Patent Application No. 200403480-7, based on the attached Examination Report of the Australian Patent Office, dated Sep. 12, 2007.

JPO—Japanese Official Action dated Jun. 24, 2008, in JP Patent Application No. 2001-506989.

JPO—Japanese Official Action dated Jun. 24, 2008, in JP Patent Application No. 2001-530082.

NO—Norway Patent Office Official action dated May 10, 2007, for Norwegian Patent Application No. 20026156, based on the attached English language Examination Report of the Russian Preliminary Examining Authority, dated Mar. 14, 2005.

U.S.P.T.O. Restriction Requirement dated Dec. 28, 2001; issued in U.S. Appl. No. 09/847,887, filed May 2, 2001.

U.S.P.T.O. Non-Final Office action dated Jun. 6, 2002; issued in U.S. Appl. No. 09/847,887, filed May 2, 2001.

U.S.P.T.O. Notice of Allowance and Fees Due dated Feb. 27, 2003; issued in U.S. Appl. No. 09/847,887, filed May 2, 2001.

U.S.P.T.O. Non-Final Office action dated Jan. 23, 2003; issued in U.S. Appl. No. 10/209,205, filed Jul. 30, 2002.

U.S.P.T.O. Notice of Allowance and Fees due dated Jun. 13, 2003; issued in U.S. Appl. No. 10/209,205, filed Jul. 30, 2002.

U.S.P.T.O. Non-Final Office action dated Nov. 12, 2004; issued in U.S. Appl. No. 10/456,932, filed Jun. 5, 2003.

U.S.P.T.O. Final Office action dated May 26, 2005; issued in U.S. Appl. No. 10/456,932, filed Jun. 5, 2003.

U.S.P.T.O. Express Abandonment Under 37 CFR 1.138 dated Dec. 16, 2005; issued in U.S. Appl. No. 10/456,932, filed Jun. 5, 2003.

U.S.P.T.O. Non-Final Office action dated Jun. 15, 2005; issued in U.S. Appl. No. 10/956,251, filed Oct. 1, 2004.

U.S.P.T.O. Mar. 23, 2006 Interview Summary dated Mar. 30, 2006; issued in U.S. Appl. No. 10/956,251, filed Oct. 1, 2004.

U.S.P.T.O. Advisory Action dated Apr. 27, 2006; issued in U.S. Appl. No. 10/956,251, filed Oct. 1, 2004.

U.S.P.T.O. Non-Final Office action dated Jun. 22, 2006; issued in U.S. Appl. No. 10/956,251, filed Oct. 1, 2004.

U.S.P.T.O. Notice of Allowance dated Jan. 22, 2007; issued in U.S. Appl. No. 10/956,251, filed Oct. 1, 2004.

U.S.P.T.O. Restriction Requirement dated Oct. 25, 2006; issued in U.S. Appl. No. 11/258,817, filed Oct. 26, 2005.

U.S.P.T.O. Non-Final Office action dated May 22, 2007; issued in U.S. Appl. No. 11/258,817, filed Oct. 26, 2005.

U.S.P.T.O. Non-Final Office action dated Dec. 12, 2007; issued in U.S. Appl. No. 11/258,817, filed Oct. 26, 2005.

U.S.P.T.O. Final Office action dated Aug. 29, 2008; issued in U.S. Appl. No. 11/258,817, filed Oct. 26, 2005.

U.S.P.T.O. Non-Final Office action dated Feb. 3, 2009; issued in U.S. Appl. No. 11/258,817, filed Oct. 26, 2005.

Bastin et al., "Salt Selection and Optimisation Procedures for Pharmaceutical New Chemical Entities," Organic Process Research and Development, Cambridge, GB, vol. 4, No. 5, Jan. 1, 2000, pp. 427-435.

ISA International Search Report dated Oct. 13, 2000 for PCT/US00/18178.

ISA International Search Report dated Oct. 29, 2001 for PCT/US01/20756.

ISA International Search Report and Written Opinion dated Apr. 6, 2005 for PCT/US04/32552.

ISEA/EP International Preliminary Examination Report dated Aug. 3, 2001 for PCT/US00/18178.

ISEA/EP International Preliminary Examination Report dated Jun. 10, 2002 for PCT/US01/20756.

ISEA/EP International Preliminary Report on Patentability dated Apr. 3, 2006 for PCT/US04/032552.

EPO—Supplementary European Search Report dated Feb. 17, 2009 for European Patent Application No. EP 04 79 4053.1.

RU—Russian Office Action (with English translation) dated Feb. 26, 2009 for Russian Patent Application No. 200600701(2006050002).

AU—Australian Examiner's Report dated Apr. 6, 2009 for Australian Patent Application No. 2004278416.

EPO—European Communication Pursuant to Article 94(3) EPC dated Jul. 13, 2009 for European Patent Application No. EP 00 946 961.0.

CA—Canadian Office Action dated Aug. 18, 2009 for Canadian Patent Application No. 2,377,309.

CN—Intellectual Property Office of the People's Republic of China Decision of Rejection (with English translation) dated Sep. 25, 2009 for Chinese Patent Application No. 200480034669.7.

U.S.P.T.O. Final Office Action dated Mar. 11, 2009 for U.S. Appl. No. 10/810,325.

U.S.P.T.O. Non-final Office Action dated Apr. 15, 2009 for U.S. Appl. No. 11/258,817.

U.S.P.T.O. Non-final Office Action dated Dec. 16, 2009 for U.S. Appl. No. 11/258,817.

U.S.P.T.O. Issue Notification dated Nov. 11, 2009 for U.S. Appl. No. 10/810,325.

Campbell, I. W., "The Clinical Significance of PPAR Gamma Agonism," Current Molecular Medicine, 2005, 5, pp. 349-363.

U.S.P.T.O. Non-Final Office Action, dated Apr. 19, 2007, for U.S. Appl. No. 10/123,298.

U.S.P.T.O. Non-Final Office Action, dated Feb. 15, 2002, for U.S. Appl. No. 09/741,415.

U.S.P.T.O. Non-Final Office Action, dated Jul. 29, 2002, for U.S. Appl. No. 09/741,415.

U.S.P.T.O. Final Office Action, dated Jan. 4, 2006, for U.S. Appl. No. 10/956,251.

U.S.P.T.O. Non-final Office Action, dated Dec. 3, 2001, for U.S. Appl. No. 09/606,433.

* cited by examiner

QUINOLINYL AND BENZOTHIAZOLYL MODULATORS

CROSS-REFERENCES TO RELATED APPLICATIONS

This application is a continuation of U.S. patent application Ser. No. 10/719,997, filed Nov. 20, 2003, now U.S. Pat. No. 7,601,841, which is a continuation of U.S. patent application Ser. No. 10/278,851, filed Oct. 21, 2002, now abandoned, which is a continuation of U.S. patent application Ser. No. 09/894,980, filed Jun. 27, 2001, now U.S. Pat. No. 6,583,157, which claims the benefit of U.S. Provisional Application No. 60/214,810, filed June 28, 2000, all of which applications are herein incorporated by reference in their entireties.

FIELD OF THE INVENTION

The present invention relates to compounds that modulate the PPARγ receptor and are useful in the diagnosis and treatment of type II diabetes (and complications thereof), hypercholesterolemia (and related disorders associated with abnormally high or low plasma lipoprotein or triglyceride levels) and inflammatory disorders.

BACKGROUND OF THE INVENTION

The peroxisome proliferator-activated receptors (PPARs) are transducer proteins belonging to the steroid/thyroid/retinoid receptor superfamily. The PPARs were originally identified as orphan receptors, without known ligands, but were named for their ability to mediate the pleiotropic effects of fatty acid peroxisome proliferators. These receptors function as ligand-regulated transcription factors that control the expression of target genes by binding to their responsive DNA sequence as heterodimers with RXR. The target genes encode enzymes involved in lipid metabolism and differentiation of adipocytes. Accordingly, the discovery of transcription factors involved in controlling lipid metabolism has provided insight into regulation of energy homeostasis in vertebrates, and further provided targets for the development of therapeutic agents for disorders such as obesity, diabetes and dyslipidemia.

PPARγ is one member of the nuclear receptor superfamily of ligand-activated transcription factors and has been shown to be expressed in an adipose tissue-specific manner. Its expression is induced early during the course of differentiation of several preadipocyte cell lines. Additional research has now demonstrated that PPARγ plays a pivotal role in the adipogenic signaling cascade. PPARγ also regulates the ob/leptin gene which is involved in regulating energy homeostasis, and adipocyte differentiation which has been shown to be a critical step to be targeted for anti-obesity and diabetic conditions.

In an effort to understand the role of PPARγ in adipocyte differentiation, several investigators have focused on the identification of PPARγ activators. One class of compounds, the thiazolidinediones, which were known to have adipogenic effects on preadipocyte and mesenchymal stem cells in vitro, and antidiabetic effects in animal models of non-insulin-dependent diabetes mellitus (NIDDM) were also demonstrated to be PPARγ-selective ligands. More recently, compounds that selectively activate murine PPARγ were shown to possess in vivo antidiabetic activity in mice.

Despite the advances made with the thiazolidinedione class of antidiabetes agents, unacceptable side effects have limited their clinical use. Accordingly, there remains a need for potent, selective activators of PPARγ which will be useful for the treatment of NIDDM and other disorders related to lipid metabolism and energy homeostasis. Still further, compounds that block PPARγ activity would be useful for interfering with the maturation of preadipocytes into adipocytes and thus would be useful for the treatment of obesity and related disorders associated with undesirable adipocyte maturation. Surprisingly, the present invention provides compounds that are useful as activators as well as antagonists of PPARγ activity, compositions containing them and methods for their use.

SUMMARY OF THE INVENTION

In one aspect, the present invention provides methods of treating or preventing a metabolic disorder or an inflammatory condition. The methods typically involve administering to a subject in need thereof a therapeutically effective amount of a compound having the formula (I):

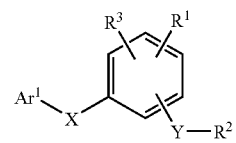

in which the symbol $Ar^1$ represents substituted or unsubstituted 2-benzothiazolyl or substituted or unsubstituted quinolinyl; X is a divalent linkage selected from —O—, —C(O)—, —CH($R^{10}$)—, —N($R^{11}$)—, and —S(O)$_k$—, wherein $R^{10}$ is selected from hydrogen, cyano and ($C_1$-$C_4$)alkyl, $R^{11}$ is selected from hydrogen and ($C_1$-$C_8$)alkyl, and the subscript k is an integer of from 0 to 2; with the proviso that when $Ar^1$ is a substituted or unsubstituted 2-benzothiazolyl, then X is other than —S(O)$_k$—.

The letter Y represents a divalent linkage having the formula —N($R^{12}$)—S(O)$_2$—, wherein $R^{12}$ is hydrogen or ($C_1$-$C_8$)alkyl.

The symbol $R^1$ represents hydrogen, ($C_2$-$C_8$)heteroalkyl, halogen, ($C_1$-$C_8$)alkyl, ($C_1$-$C_8$)alkoxy, —C(O)$R^{14}$, —CO$_2R^{14}$, —C(O)NR$^{15}$R$^{16}$, —S(O)$_p$—R$^{14}$, —S(O)$_q$—NR$^{15}$R$^{16}$, —O—C(O)—R$^{17}$ or —N(R$^{14}$)—C(O)—R$^{17}$; wherein $R^{14}$ is selected from hydrogen, ($C_1$-$C_8$)alkyl, ($C_2$-$C_8$)heteroalkyl, aryl and aryl($C_1$-$C_4$)alkyl; $R^{15}$ and $R^{16}$ are independently selected from hydrogen, ($C_1$-$C_8$)alkyl, ($C_2$-$C_8$)heteroalkyl, aryl, and aryl($C_1$-$C_4$)alkyl, or taken together with the nitrogen to which each is attached form a 5-, 6- or 7-membered ring; $R^{17}$ is selected from ($C_1$-$C_8$)alkyl, ($C_2$-$C_8$)heteroalkyl, aryl and aryl($C_1$-$C_4$)alkyl; the subscript p is an integer of from 0 to 3; and the subscript q is an integer of from 1 to 2.

$R^2$ is substituted or unsubstituted aryl; and $R^3$ is selected from halogen and ($C_1$-$C_8$)alkoxy.

In another aspect, the present invention provides methods of treating or preventing a condition or disorder mediated by PPARγ and methods for modulating PPARγ.

In yet another aspect, the present invention provides compounds of formula I and pharmaceutical compositions containing compounds of formula I.

DETAILED DESCRIPTION OF THE INVENTION

Abbreviations and Definitions

The abbreviations used herein are conventional, unless otherwise defined.

As used herein, "diabetes" refers to type I diabetes mellitus (juvenile diabetes) or type II diabetes mellitus (non-insulin-dependent diabetes mellitus or NIDDM), preferably, type II diabetes mellitus.

The terms "treat", "treating" and "treatment" refer to a method of alleviating or abrogating a disease and/or its attendant symptoms.

The terms "prevent", "preventing" and "prevention" refer to a method of decreasing the probability or eliminating the possibility that a disease will be contracted.

As used herein, the term "PPARγ-mediated condition or disorder" and the like refers to a condition or disorder characterized by inappropriate, e.g., less than or greater than normal, PPARγ activity. A PPARγ-mediated condition or disorder may be completely or partially mediated by inappropriate PPARγ activity. However, a PPARγ-mediated condition or disorder is one in which modulation of PPARγ results in some effect on the underlying condition or disease (e.g., a PPARγ antagonist results in some improvement in patient well-being in at least some patients). Exemplary PPARγ-mediated conditions and disorders include metabolic disorders, e.g., diabetes, obesity, hyperglycemia, insulin resistance, hyperinsulinemia, hypercholesterolemia, hypertension, hyperlipoproteinemia, hyperlipidemia, hypertriglylceridemia and dyslipidemia, and inflammatory conditions, e.g., rheumatoid arthritis and atherosclerosis.

The term "modulate" refers to the ability of a compound to increase or decrease the function, or activity, of PPARγ. Modulation, as described herein, includes the inhibition or activation of PPARγ, either directly or indirectly. Inhibitors are compounds that, e.g., bind to, partially or totally block stimulation, decrease, prevent, delay activation, inactivate, desensitize, or down regulate signal transduction, e.g., antagonists. Activators are compounds that, e.g., bind to, stimulate, increase, open, activate, facilitate, enhance activation, sensitize or up regulate signal transduction, e.g., agonists.

The term "therapeutically effective amount" refers to that amount of the compound being administered sufficient to prevent development of or alleviate to some extent one or more of the symptoms of the condition or disorder being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms are optionally oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, as well as all other linking group provided in the present invention, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-benzothiazolyl, 5-benzothiazolyl, 2-benzoxazolyl, 5-benzoxazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. Substituents for each of the above noted aryl ring systems are selected from the group of acceptable substituents described below. The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R''', —OC(O)R', —C(O)R', —CO$_2$R', CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. R', R" and R''' each independently refer to hydrogen, unsubstituted (C$_1$-C$_8$)alkyl and heteroalkyl, unsubstituted aryl, aryl substituted with 1-3 halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g. —C(O)CH$_3$, —C(O)CF$_3$, —C(O)CH$_2$OCH$_3$, and the like). Preferably, the alkyl groups (and related alkoxy, heteroalkyl, etc.) are unsubstituted or have 1 to 3 substituents selected from halogen, —OR', =O, —NR'R", —SR', —OC(O)R', —C(O)R', —CO$_2$R', —CONR'R", —NR"C(O)R', —S(O)$_2$R', —S(O)$_2$NR'R", —CN and —NO$_2$. More preferably, the alkyl and related groups have 0, 1 or 2 substituents selected from halogen, —OR', =O, —NR'R", —SR', —CO$_2$R', —CONR'R", —NR"C(O)R', —CN and —NO$_2$.

Similarly, substituents for the aryl groups are varied and are selected from halogen, —OR', —OC(O)R', —NR'R", —SR', —R', —CN, —NO$_2$—, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl, (unsubstituted aryl)-(C$_1$-C$_4$)alkyl, and (unsubstituted aryl)oxy-(C$_1$-C$_4$)alkyl. Preferably, the aryl groups are unsubstituted or have from 1 to 3 substituents selected from halogen, —OR', —OC(O)R', —NR'R", —SR', —R', —CN, —NO$_2$— —CO$_2$R', —CONR'R", —C(O)R', —NR"C(O)R', —S(O)$_2$R', —S(O)$_2$NR'R", perfluoro(C$_1$-C$_4$)alkoxy, and perfluoro(C$_1$-C$_4$)alkyl. Still more preferably, the aryl groups have 0, 1 or 2 substituents selected from halogen, —OR', —NR'R", —SR', —R', —CN, —NO$_2$— —CO$_2$R', —CONR'R", —NR"C(O)R', —S(O)$_2$R', —S(O)$_2$NR'R", perfluoro(C$_1$-C$_4$) alkoxy, and perfluoro(C$_1$-C$_4$)alkyl.

Two of the substituents on adjacent atoms of the aryl ring may optionally be replaced with a substituent of the formula wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

EMBODIMENTS OF THE INVENTION

A new class of compounds that modulate PPARγ has now been discovered. Depending on the biological environment (e.g., cell type, pathological condition of the subject, etc.), these compounds of the present invention can activate or inhibit PPARγ activity. Thus, the compounds of the invention are useful in the treatment or prevention of conditions and disorders associated with energy homeostasis, lipid metabolism, adipocyte differentiation and inflammation (see, Ricote et al. (1998) *Nature* 391:79-82 and Jiang et al. (1998) *Nature* 391:82-86). For example, compounds that activate PPARγ are useful in the treatment of metabolic disorders, such as diabetes. Additionally, the compounds of the invention are useful for the prevention and treatment of complications of metabolic disorders, such as diabetes, e.g., neuropathy, retinopathy, glomerulosclerosis and cardiovascular disorders.

In addition to their anti-diabetic activity, many synthetic PPARγ ligands also promote increased body weight gain, a situation that can aggravate the diabetic and obese condition. The ligands exemplified herein improve upon this profile by providing effective lowering of serum glucose levels in the absence of such profound increases in body weight.

Related compounds of the more general class have in certain instances been modified to produce pharmacologically active metabolites with exposures and in vivo lifetimes that exceed the parent compounds. In the treatment of certain chronic conditions, such metabolites have been linked to untoward conditions. Some of the compounds contemplated by the present invention avoid the formation of such long-lived metabolites while still maintaining the desirable pharmacological properties of the general class.

PPARγ Modulators

The present invention provides compounds which are represented by the formula (I):

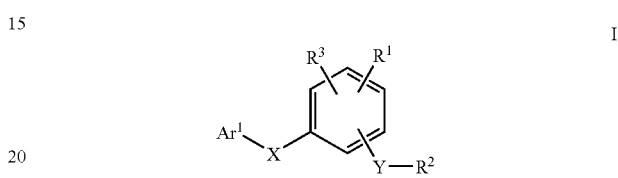

In formula I, the symbol $Ar^1$ represents a substituted or unsubstituted 2-benzothiazolyl or substituted or unsubstituted quinolinyl group. The letter X represents a divalent linkage selected from —O—, —C(O)—, —CH($R^{10}$)—, —N($R^{11}$)—, and —S(O)$_k$—, wherein $R^{10}$ is represents hydrogen, cyano or ($C_1$-$C_4$)alkyl; and $R^{11}$ represents hydrogen or ($C_1$-$C_8$)alkyl, and the subscript k is an integer of from 0 to 2; with the proviso that when $Ar^1$ is a substituted or unsubstituted 2-benzothiazolyl, then X is other than —S(O)$_k$—.

The letter Y represents a divalent linkage having the formula —N($R^{12}$)—S(O)$_2$—, wherein $R^{12}$ is hydrogen or ($C_1$-$C_8$)alkyl. The symbol $R^1$ represents hydrogen, ($C_2$-$C_8$)heteroalkyl, halogen, ($C_1$-$C_8$)alkyl, ($C_1$-$C_8$)alkoxy, —C(O)$R^{14}$, —CO$_2R^{14}$, —C(O)NR$^{15}$R$^{16}$, —S(O)$_p$—$R^{14}$, —S(O)$_q$—NR$^{15}$R$^{16}$, —O—C(O)—$R^{17}$ or —N($R^{14}$)—C(O)—$R^{17}$, wherein $R^{14}$ is selected from hydrogen, ($C_1$-$C_8$)alkyl, ($C_2$-$C_8$)heteroalkyl, aryl and aryl($C_1$-$C_4$)alkyl; $R^{15}$ and $R^{16}$ are members independently selected from hydrogen, ($C_1$-$C_8$)alkyl, ($C_2$-$C_8$)heteroalkyl, aryl, and aryl($C_1$-$C_4$)alkyl, or taken together with the nitrogen to which each is attached form a 5-, 6- or 7-membered ring; $R^{17}$ is selected from ($C_1$-$C_8$)alkyl, ($C_2$-$C_8$)heteroalkyl, aryl and aryl($C_1$-$C_4$)alkyl; the subscript p is an integer of from 0 to 3; and the subscript q is an integer of from 1 to 2.

The symbol $R^2$ represents a substituted or unsubstituted aryl; and $R^3$ represents a halogen or ($C_1$-$C_8$)alkoxy.

One of skill in the art will understand that a number of structural isomers are represented by formula I. In one group of embodiments, the isomers are those in which the groups on the phenyl ring occupy positions that are not contiguous. In other embodiments, the compounds are those having the structural orientations represented by the formulae (Ia-Ij):

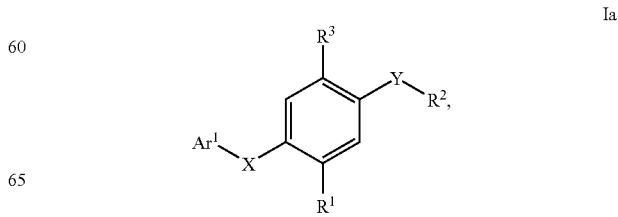

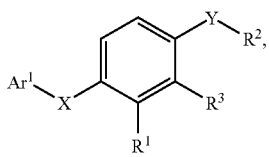
Ib

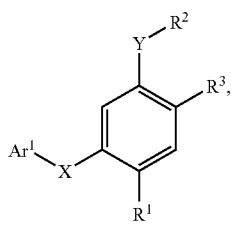
Ic

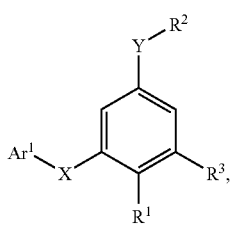
Id

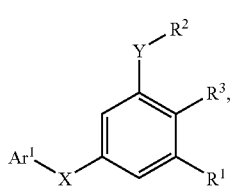
Ie

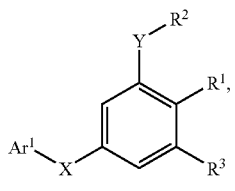
If

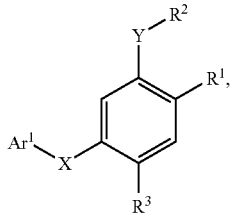
Ig

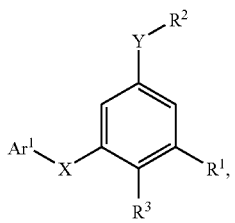
Ih

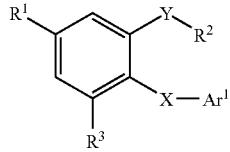
Ii and

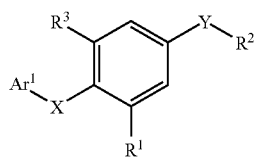
Ij $Ar^1$ is Substituted or Unsubstituted 2-benzothiazolyl

A number of preferred embodiments are provided herein. For example, in one preferred embodiment, $Ar^1$ is a substituted or unsubstituted 2-benzothiazolyl; X is —O— or —N($R^{11}$)—; Y is —NH—S(O)$_2$—; $R^1$ is hydrogen, halogen, ($C_1$-$C_8$)alkoxy, ($C_1$-$C_8$)alkyl, —CO$_2R^{14}$ or —C(O)NR$^{15}R^{16}$ wherein $R^{14}$ is hydrogen, ($C_1$-$C_8$)alkyl, ($C_2$-$C_8$)heteroalkyl, aryl and aryl($C_1$-$C_4$)alkyl, $R^{15}$ and $R^{16}$ are independently selected from hydrogen, ($C_1$-$C_8$)alkyl, ($C_2$-$C_8$)heteroalkyl, aryl, and aryl($C_1$-$C_4$)alkyl, or taken together with the nitrogen to which each is attached form a 5-, 6- or 7-membered ring; $R^2$ is substituted or unsubstituted phenyl; and $R^3$ is halogen or ($C_1$-$C_4$)alkoxy.

In a further preferred embodiment, $R^1$ is selected from halogen, cyano, ($C_1$-$C_8$)alkoxy, ($C_1$-$C_8$)alkyl, —CO$_2R^{14}$ and —C(O)NR$^{15}R^{16}$ wherein $R^{14}$ is ($C_1$-$C_8$)alkyl; $R^{15}$ and $R^{16}$ are independently selected from hydrogen and ($C_1$-$C_8$)alkyl, or taken together with the nitrogen to which each is attached form a 5- or 6-membered ring.

In still other preferred embodiments, $R^1$ is selected from halogen, cyano, ($C_1$-$C_8$)alkoxy, and ($C_1$-$C_8$)alkyl. In yet other preferred embodiments, X is selected from —O— and —NH—. In still other preferred embodiments, $R^2$ is substituted phenyl having from 1 to 3 substituents independently selected from halogen, cyano, nitro, —OCF$_3$, —OH, —O($C_1$-$C_6$)alkyl, —CF$_3$, ($C_1$-$C_8$)alkyl.

In a particularly preferred embodiment of the invention, $Ar^1$ is a substituted or unsubstituted 2-benzothiazolyl group; X is —O— or —NH—; Y is —NH—S(O)$_2$—; $R^1$ is hydrogen, halogen, cyano, ($C_1$-$C_8$)alkoxy, ($C_1$-$C_8$)alkyl, —CO$_2R^{14}$ or —C(O)NR$^{15}R^{16}$, wherein $R^{14}$ is hydrogen or ($C_1$-$C_8$)alkyl; $R^{15}$ and $R^{16}$ are independently selected from hydrogen and ($C_1$-$C_8$)alkyl, or taken together with the nitrogen to which each is attached form a 5-, 6- or 7-membered ring; $R^2$ is substituted phenyl having from 1 to 3 substituents independently selected from halogen, cyano, nitro, —OCF$_3$, —OH, —O($C_1$-$C_6$)alkyl, —CF$_3$, ($C_1$-$C_8$)alkyl; and $R^3$ is halogen or ($C_1$-$C_4$)alkoxy. Still further preferred are those embodiments in which the compound is represented by a formula selected from:

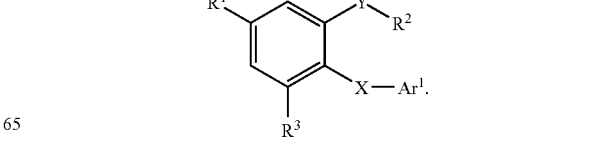
Ii and Ij

In the most preferred embodiments, the compound is selected from:

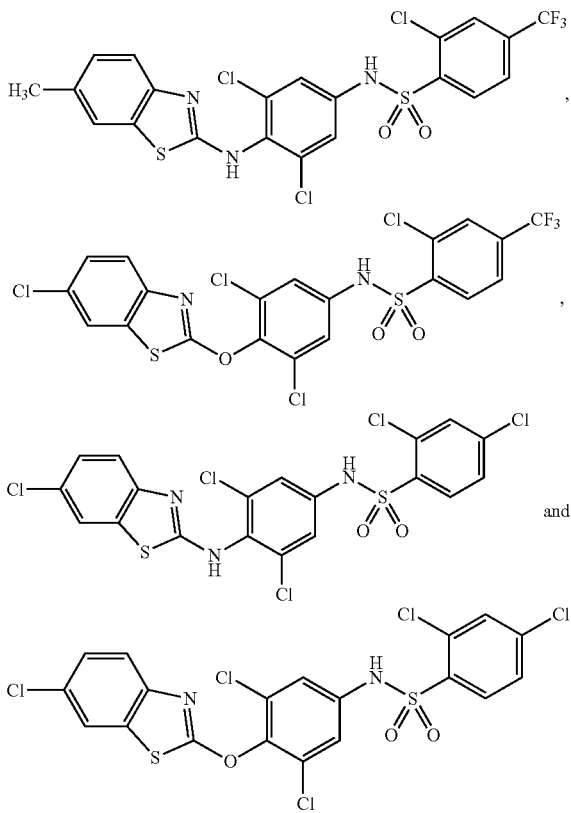

Ar¹ is Substituted or Unsubstituted Quinolinyl

In another group of preferred embodiments, Ar¹ is a substituted or unsubstituted quinolinyl group; X is selected from —O—, —S— and —N(R¹¹)—; Y is —N(R¹²)—S(O)₂—, wherein R¹² is selected from hydrogen and (C₁-C₈)alkyl; R¹ is selected from hydrogen, halogen, cyano, (C₁-C₈)alkoxy, (C₁-C₈)alkyl, —CO₂R¹⁴ and —C(O)NR¹⁵R¹⁶, wherein R¹⁴ is selected from hydrogen, (C₁-C₈)alkyl, (C₁-C₈)heteroalkyl, aryl and aryl(C₁-C₄)alkyl, and R¹⁵ and R¹⁶ are independently selected from hydrogen, (C₁-C₈)alkyl, (C₂-C₈)heteroalkyl, aryl, and aryl(C₁-C₄)alkyl, or taken together with the nitrogen to which each is attached form a 5-, 6- or 7-membered ring; R² is substituted or unsubstituted phenyl; and R³ is selected from halogen and (C₁-C₈)alkoxy.

Still further preferred are those compounds in which R¹ is selected from halogen, cyano, (C₁-C₈)alkoxy, (C₁-C₈)alkyl, —CO₂R¹⁴ and —C(O)NR¹⁵R¹⁶ wherein R¹⁴ is (C₁-C₈)alkyl; R¹⁵ and R¹⁶ are independently selected from hydrogen and (C₁-C₈)alkyl, or taken together with the nitrogen to which each is attached form a 5- or 6-membered ring.

In still other preferred embodiments, R¹ is selected from halogen, cyano, (C₁-C₈)alkoxy, and (C₁-C₈)alkyl. In yet other preferred embodiments, X is selected from —O—, —S— and —NH—. In still other preferred embodiments, Y is —NH—S(O)₂—. In other preferred embodiments, R² is substituted phenyl having from 1 to 3 substituents independently selected from halogen, cyano, nitro, —OCF₃, —OH, —O(C₁-C₆)alkyl, —CF₃, (C₁-C₈)alkyl.

In a particularly preferred embodiment of the invention, Ar¹ is a substituted or unsubstituted quinolinyl group; X is —O—, —S— or —NH—; Y is —NH—S(O)₂—; R¹ is hydrogen, halogen, cyano, (C₁-C₈)alkoxy, (C₁-C₈)alkyl, —CO₂R¹⁴ or —C(O)NR¹⁵R¹⁶, wherein R¹⁴ is hydrogen or (C₁-C₈)alkyl; R¹⁵ and R¹⁶ are independently selected from hydrogen and (C₁-C₈)alkyl, or taken together with the nitrogen to which each is attached form a 5-, 6- or 7-membered ring; R² is substituted phenyl having from 1 to 3 substituents independently selected from halogen, cyano, nitro, —OCF₃, —OH, —O(C₁-C₆)alkyl, —CF₃, (C₁-C₈)alkyl; and R³ is halogen or (C₁-C₄)alkoxy. Still further preferred are those embodiments in which the compound is represented by a formula selected from:

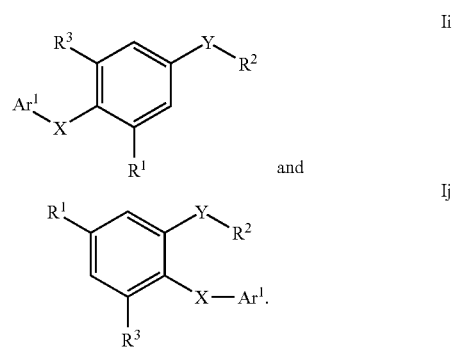

In the most preferred embodiments, the compound is selected from:

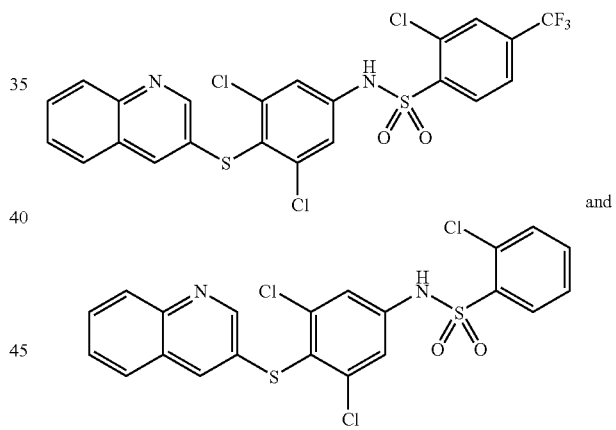

In another aspect, the present invention provides pharmaceutical compositions comprising at least one of the above compounds in admixture with a pharmaceutically acceptable excipient.

In yet another aspect, the present invention provides methods for modulating conditions mediated by PPARγ. More particularly, the conditions are selected from non-insulin-dependent diabetes mellitus, obesity, conditions associated with abnormal plasma levels of lipoproteins or triglycerides, and inflammatory conditions such as, for example, rheumatoid arthritis and atherosclerosis.

Preparation of the Compounds

The compounds of the present invention can be prepared using standard synthetic methods. Schemes 1-3 illustrate exemplary methods for the preparation of compounds of structural formula (Ia). One of skill in the art will understand that similar methods can be used for the synthesis of compounds in the other structural classes.

As shown in Scheme 1, compounds of the present invention can be prepared beginning with commercially available 2-chloro-5-nitrobenzonitrile (i). Treatment of i with a phenol, thiophenol, or optionally protected aniline in the presence of base and heat provides the adduct (ii). Reduction of the nitro group in ii with, for example, $H_2$ in the presence of Raney nickel catalyst provides an aniline derivative (iii). Sulfonylation of iii with an appropriate arylsulfonyl halide ($Ar^1SO_2C_1$) in the presence of base (typically a tertiary amine) provides a target compound (iv). Compound iii can also be converted to a related compound of formula (vi) in which the orientation of the sulfonamide linkage is reversed. Thus, conversion of the aniline iii to the benzenesulfonyl chloride v can be accomplished using methods described in Hoffman, *Organic Syntheses Collective Volume VII*, pp. 508-511. Subsequent treatment of v with an appropriate aniline provides the target compound vi.

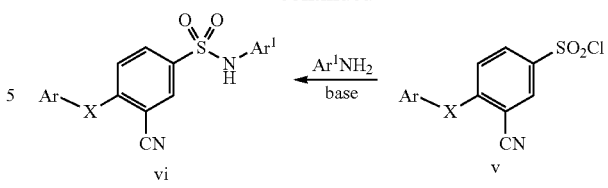

Scheme 2 depicts an alternative preparation of compounds of formula I (wherein $Ar^1$ is substituted or unsubstituted 2-benzothiazolyl and X is —O—).

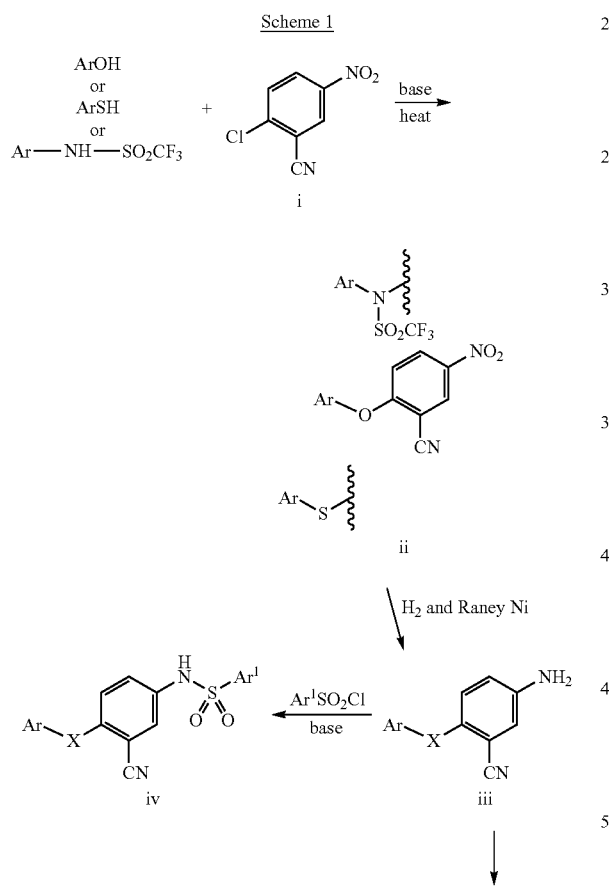

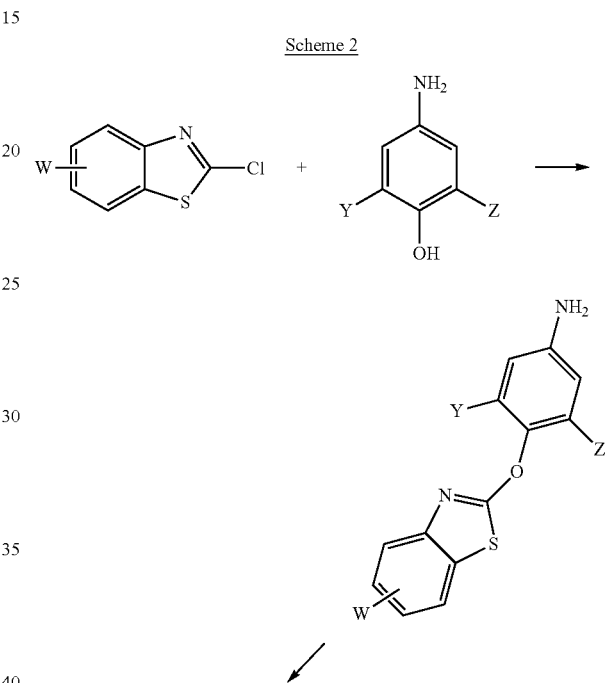

Scheme 3 depicts an alternative preparation of compounds of formula I, wherein $Ar^1$ is substituted or unsubstituted 2-benzothiazolyl and X is —$N(R^{11})$—.

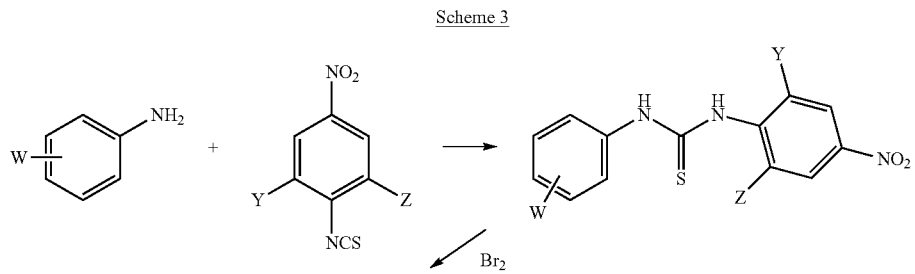

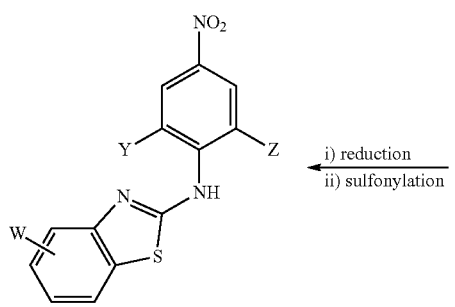 i) reduction ii) sulfonylation 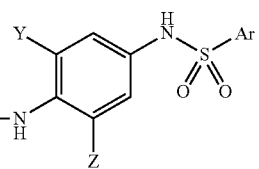

Other compounds of the present invention can be prepared beginning with, for example, 3,4-difluoronitrobenzene, 3-chloro-4-fluoronitrobenzene, 2-chloro-5-nitroanisole, 3-bromo-4-fluoronitrobenzene and the like.

Analysis of the Compounds

The compounds of the present invention can be evaluated for modulation of the PPARγ receptor using assays such as those described in Jiang, et al., *Nature* 391:82-86 (1998), Ricote, et al., *Nature* 391:79-82 (1998) and Lehmann, et al., *J. Biol. Chem.* 270(12): 12953-12956 (1995). Alternatively, the compounds can be evaluated for their ability to displace radiolabeled BRL 49653 from a PPARγ-GST fusion protein as follows:

Materials:

PPARγ-GST fusion protein (prepared according to standard procedures), [$^3$H]—BRL 49653 having 50 Ci/mmol specific activity, Polyfiltronics Unifilter 350 filtration plate and glutathione-Sepharose® beads (from Pharmacia: washed twice with 10× binding buffer in which BSA and DTI can be left out).

Method:

Binding buffer (10 mM Tris-HCl, pH 8.0, 50 mM KCl, 10 mM DTT, 0.02% BSA and 0.01% NP-40) is added in 80-μL amounts to the wells of the filtration plate. The test compound is then added in 10 μL of DMSO. The PPARγ-GST fusion protein and radiolabeled BRL compound are premixed in binding buffer containing 10 mM DTT and added in 10-μL amounts to the wells of the plate to provide final concentrations of 1 μg/well of PPARγ-GST fusion protein and 10 nM [$^3$H]—BRL 49653 compound. The plate is incubated for 15 min. Glutathione-agarose bead is added in 50 μL of binding buffer, and the plate is vigorously shaken for one hour. The plate is washed four times with 200 μL/well of binding buffer (without BSA and DTT). The bottom of the plate is sealed and 200 μL/well of scintillation cocktail is added. The top of the plate is then sealed and the radioactivity is determined.

Compositions

The compounds of the present invention can administered via any suitable route, most preferably orally or parenterally, in a preparation appropriately tailored to that route. Thus, the compounds of the present invention can be administered by injection, for example, intravenously, intramuscularly, intracutaneously, subcutaneously, intraduodenally, or intraperitoneally. The present invention also contemplates the use of depot formulations in which the active ingredient(s) is released over a defined time period. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of formula I or a pharmaceutically acceptable salt of a compound of formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment of obesity, diabetes, inflammatory conditions or other conditions or disorders mediated by PPARγ, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compositions may be advantageously combined and/or used in combination with agents useful in the treatment and/or prevention of metabolic disorders and inflammatory conditions, complications thereof and pathologies associated therewith (e.g., cardiovascular disease and hypertension). In many instances, administration of the subject compounds or compositions in conjunction with these alternative agents enhances the efficacy of such agents. Accordingly, in some instances, the present compounds, when combined or administered in combination with, e.g., anti-diabetic agents, can be used in dosages which are less than the expected amounts when used alone, or less than the calculated amounts for combination therapy.

Suitable agents for combination therapy include those that are currently commercially available and those that are in development or will be developed. Exemplary agents useful in the treatment of metabolic disorders include, but are not limited to: (a) anti-diabetic agents such as insulin, sulfonylureas (e.g., meglinatide, tolbutamide, chlorpropamide, acetohexamide, tolazamide, glyburide, glipizide and glimepiride), biguanides, e.g., metformin (Glucophage®), α-glucosidase inhibitors (acarbose), thiazolidinone compounds, e.g., rosiglitazone (Avandia®), troglitazone (Rezulin®) and pioglitazone (Actos®); (b) $\beta_3$ adrenergic receptor agonists, leptin or derivatives thereof and neuropeptide Y antagonists; (c) bile acid sequestrants (e.g., cholestyramine and colestipol), HMG-CoA reductase inhibitors, e.g., statins (e.g., lovastatin, atorvastatin, fluvastatin, pravastatin and simvastatin), nicotinic acid (niacin), fibric acid derivatives (e.g., gemfibrozil and clofibrate) and nitroglycerin. Exemplary agents useful in the treatment of inflammatory conditions include, but are not limited to: (a) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (b) cyclooxygenase-2 (COX-2) inhibitors such as celecoxib (Celebrex®) and rofecoxib (Vioxx®) and (c) inhibitors of phosphodiesterase type IV (PDE-IV).

Methods of Use

The present invention provides methods of using the foregoing compounds and compositions to treat or prevent a metabolic disorder or an inflammatory condition. The present invention also provides methods of using the foregoing compounds and compositions to treat or prevent a condition or disorder mediated by PPARγ. The methods comprise administering to a subject in need thereof a therapeutically effective amount of a compound of formula I.

In still another aspect, the present invention provides methods of using the foregoing compounds and compositions to modulate PPARγ. The methods comprise contacting a cell with the compound of formula I.

The following examples are offered by way of illustration and are not intended to limit the scope of the invention.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 μL was infused with the delivery solvent into the mass spectrometer which scanned from 100 to 1500 daltons (D). All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent.

Abbreviations

Triethylamine (Et$_3$N), methanol (MeOH), dimethylsulfoxide (DMSO), N-methylmorpholine (NMM), dimethylformamide (DMF), 4-dimethylamino)pyridine (DMAP), 3-chloroperoxybenzoic acid (mCPBA), ethyl acetate (AcOEt), ethanol (EtOH), hexamethylphosphoramide (HMPA), acetic acid (AcOH), silver benzoate (AgOBz), tetrahydrofuran (THF), N-hydroxybenzotriazole (HOBT), 2-(1H-benzotriazole-1-yl)-1,1,3,3-tetramethyluronium hexafluorophosphate (HBTU), 1-hydroxy-7-azabenzotriazole (HOAT), O-(7-azabenzotriazole-1-yl)-N,N,N',N'-tetramethyluronium hexafluorophosphate (HATU), 1-(3-dimethylaminopropyl)-3-ethylcarbodiimide hydrochloride (EDCI).

Certain intermediates used in preparing the compounds below are described in co-pending U.S. patent application Ser. No. 09/606,433, filed Jun. 28, 2000.

Example 1

The following benzenesulfonyl chlorides were prepared by the procedure of R. V. Hoffman (*Org. Syn. Coll. Vol. VII*, 508-511) from the corresponding commercially available anilines and used to make the indicated examples.

2-Chloro-4-t-butylbenzenesulfonyl chloride (1a). Yield 34%. $^1$H NMR (CDCl$_3$) δ 8.06 (1H, d, J=8.4 Hz), 7.62 (1H, s), 7.48 (1H, d, J=8.4 Hz), 1.37 (9H, s); m.p. 68.8° C.

2-Trifluoromethyl-4-chlorobenzenesulfonyl chloride (1b). Yield 76% as a solid. $^1$H NMR (CDCl$_3$) δ 8.325 (d, J=8.4 Hz, 1H), 7.966 (br s, 1H), 7.829 (br d, J=8.4 Hz, 1H). m.p. 37.0° C.

2-Chloro-4-methylbenzenesulfonyl chloride (1c). Yield 47% as an oil.

$^1$H NMR (CDCl$_3$) δ 8.02 (1H, d, J=8.8 Hz), 7.46 (1H, s), 7.28 (1H, d, J=8.8 Hz), 2.47 (3H, s)

Example 2

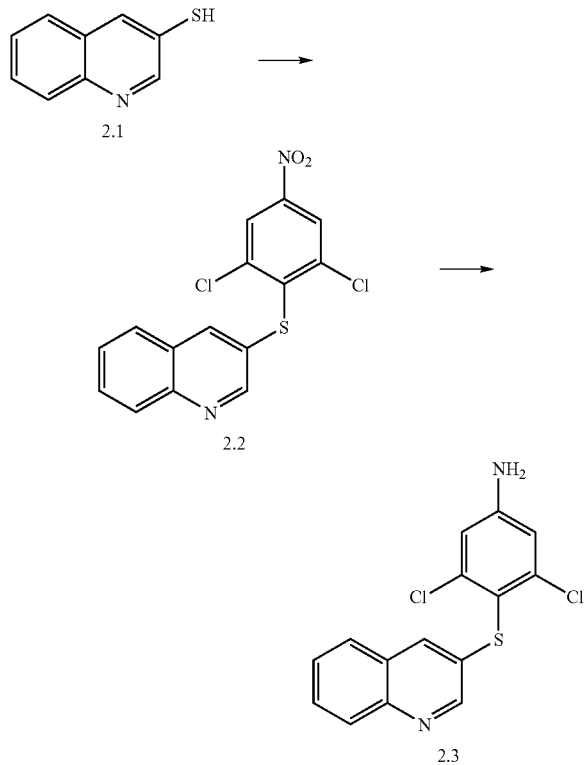

Compound 2.3. Compound 2.1 was prepared by a modification of the published procedure of Albert and Barlin (*J. Chem. Soc.* 2384-2396 (1959)). 3-Aminoquinoline (15.0 g, 105 mmol) was suspended in a mixture of 10N HCl (40 mL), ice (21 g) and water (100 mL) at 0-5° C., before sodium nitrite (7.6 g, 110 mmol) was added slowly. The mixture was then added portionwise to another solution of potassium ethyl xanthate (20.8 g, 125 mmol) in water (60 mL) at 45° C. The mixture was heated for 1 h before cooling off. The mixture was then extracted with ether. The ethereal solution was washed with 2N NaOH solution, water, and brine before drying over magnesium sulfate. After filtration, the removal of the solvent gave a brown oil (15 g), which was then dissolved in ethanol (150 mL) and refluxed with KOH (25 g) under nitrogen overnight. The ethanol solvent was then removed under vacuum, and the residue was separated between water and ether. The ethereal solution was discarded. The aqueous solution was acidified to pH=~4, before it was extracted with ether. Then ethereal solution was washed with brine, dried over magnesium sulfate, filtered and concentrated under vacuum to give crude product (7.5 g) as a brown oil. Subsequent flash chromatography with eluent (0%-5%-10% ethyl acetate/dichloromethane) produced 3-mercaptoquinoline (2.1) (5.35 g, 32% yield) as a solid. $^1$H NMR (DMSO) δ 9.02 (1H, d, J=2.3 Hz), 8.63 (1H, d, J=2.2 Hz), 7.95-8.05 (2H, m), 7.75-8.02 (1H, m), 7.60-7.67 (1H, m).

To a mixture of 3-mercaptoquinoline (2.1) (1.18 g, 7.33 mmol) and 1,2,3-chloro-5-nitrobenzene (1.66 g, 7.33 mmol) dissolved in ethanol (100 mL), was added a THF solution of t-BuOK (7.5 mL, 1M). The mixture was then heated at 80° C. overnight before cooling off. After the removal of ethanol solvent, the mixture was separated between ethyl acetate and water. The organic solution was washed with brine, dried over magnesium sulfate and filtered. The filtrate was then concentrated to give a crude product, which was then flash chromatographed with eluent (10% hexanes/dichloromethane) to afford 2.2 (1.80 g, 70% yield) as a yellow oil. $^1$H NMR (DMSO) δ 8.75 (1H, d, J=2.3), 8.51 (1H, s), 8.22 (1H, s), 8.01 (1H, d, J=8.4 Hz), 7.92 (1H, d, J=7.6 Hz), 7.74-7.80 (1H, m), 7.60-7.66 (1H, m).

An ethyl acetate solution (100 mL) of 2.2 (1.80 g, 5.1 mmol) and tin chloride (II) dihydrate (6.88 g, 30 mmol) was heated at reflux overnight before cooling off. The solution was then poured into 1N NaOH solution (400 mL). After stirring for 30 min, the mixture was separated, and the organic solution was washed with water, saturated sodium bicarbonate and brine. After drying over magnesium sulfate, the solution was filtered and concentrated under vacuum. The residue was mixed with dichloromethane (10 mL) and sonicated. Subsequent vacuum filtration provided the aniline 2.3 (1.35 g, 82% yield) as an off-white solid. $^1$H NMR (DMSO) δ 8.61 (1H, d, J=2.4), 7.96 (1H, d, J=8.4 Hz), 7.88 (1H, d, J=8.2 Hz), 7.83 (1H, d, J=2.2 Hz), 7.67-7.72 (1H, m), 7.54-7.60 (1H, m). mp 213.2° C.

Example 3

Compound 3. The aniline 2.3 (250 mg, 0.78 mmol) and 2-chlorobenzenesulfonyl chloride (339 mg, 1.60 mmol) were dissolved in a mixed solvent of THF (5 mL) and dichloromethane (5 mL). To the solution was added pyridine (0.185 mL, 2.34 mmol) and catalytic amount of DMAP. The solution was heated at 50° C. to distill off dichloromethane, and then THF with assistance of vacuum. The residue was flash chromatographed with eluent (2.5% ethyl acetate/dichloromethane) to give sulfonamide 3 (see Table 1) (302 mg, 78%) as an off-white solid. $^1$H NMR (DMSO) δ 11.58 (1H, s), 8.61 (1H, d, J=2.4 Hz), 8.19 (1H, d, J=7.6 Hz), 7.83-8.00 (3H, m), 7.67-7.75 (3H, m), 7.56-7.65 (2H, m), 7.31 (2H, s). MS (M+H) 494.9. mp: 219.6° C. Anal. calcd: C 50.87, H 2.64, N 5.65; found C 50.86, H 2.62, N 5.52.

TABLE 1

[Structure: sulfonamide with Ra, Rb, Rc, Rd substituents on one phenyl ring; other ring has Cl, Cl substituents and S(=O)k linkage to quinoline]

| Compound | k | $R_a$ | $R_b$ | $R_c$ | $R_d$ | m/e (M + H) |
|---|---|---|---|---|---|---|
| 3 | 0 | Cl | H | H | H | 495 |
| 4.1 | 0 | Cl | H | Cl | H | 529 |
| 4.2 | 0 | H | H | H | H | 461 |
| 4.3 | 0 | Cl | H | CF$_3$ | H | 561 (M – H) |
| 5.1 | 1 | Cl | H | H | H | 511 |
| 5.2 | 1 | Cl | H | Cl | H | 543 (M – H) |
| 5.3 | 1 | H | H | H | H | 477 |

Example 4

The compounds of Table 1 were prepared by the method of Example 3 from compound 2.3 and the corresponding arylsulfonyl chloride.

Example 4.1

$^1$H NMR (DMSO) δ 11.66 (1H, broad), 8.63 (1H, d, J=2.3 Hz), 8.18 (1H, d, J=8.6 Hz), 7.85-8.00 (4H, m), 7.70-7.75 (2H, m), 7.57-7.62 (1H, m), 7.32 (2H, s).

MS (M+H) 529.0. mp 214.0° C. Elemental Analysis: theory C 47.56, H 2.28, N 5.28; Found C47.30, H 2.36, N 5.37.

Example 4.2

$^1$H NMR (DMSO): δ 11.22 (1H, s), 8.61 (1H, d, J=2.3 Hz), 7.82-7.98 (5H, m), 7.57-7.75 (5H, m), 7.34 (2H, s). MS (M+H) 461.0. mp 246.8° C. Elemental Analysis theory C 54.67, H 3.06, N 6.07; found C 54.71, H 3.05, N 5.94.

Example 4.3

$^1$H NMR (DMSO) δ 11.70-12.00 (1H, broad), 8.60-8.67 (1H, m), 8.35-8.43 (1H, m), 8.20-8.25 (1H, m), 7.56-8.06 (6H, m), 7.32-7.38 (2H, m). MS (M–H) 560.9. mp: 225.1° C. Elemental Analysis: theory C 46.86, H 2.15, N 4.97; found C. 47.01, H 2.26, N 4.98.

Example 5

General procedure for sulfur oxidation to the sulfoxide. A naphthylthioether of Examples 3 or 4 (0.2 mmol) was dissolved in a mixed solvent of dichloromethane (10 mL) and methanol (5 mL). To the solution was added mCPBA (120 mg, 0.7 mmol, 77% pure) in six batches over 20 min. intervals. Then the solution was washed with 5% sodium thiosulfate solution, 1% sodium bicarbonate solution and brine and then dried over magnesium sulfate. After filtering, the filtrate was concentrated to give a crude product, which was then flash chromatographed with eluent (5%-30% ethyl acetate/dichloromethane) to afford the corresponding sulfoxide.

Example 5.1

$^1$H NMR (DMSO): δ 11.75 (1H, s), 8.82 (1H, s), 8.68 (1H, s), 8.15-8.20 (2H, m), 8.09 (1H, d, J=8.5 Hz), 7.85-7.91 (1H, m), 7.67-7.75 (3H, m), 7.57-7.64 (1H, m), 7.17 (2H, s). MS (M+H) 511. mp 239.5° C. with decomposition. Elemental Analysis: theory C 49.28, H 2.56, N 5.47; found C 49.30, H 2.63, N 5.37.

Example 5.2

$^1$H NMR (DMSO): δ 11.5-12.0 (broad), 8.83 (1H, s), 8.68 (1H, s), 8.15-8.20 (2H, m), 8.09 (1H, d, J=8.5 Hz), 7.85-7.92 (2H, m), 7.55-7.75 (2H, m), 7.17 (2H, s). MS (M–H) 542.9. mp: 234.4. Elemental Analysis: theory C 46.17, H 2.21, N 5.13; found C 45.97, H 2.26, N 4.92.

Example 5.3

$^1$H NMR (DMSO) δ 11.43 (1H, s), 8.81 (1H, s), 8.68 (1H, s), 8.18 (1H, d, J=8.2 Hz), 8.09 (1H, d, J=8.5 Hz), 7.82-7.90 (3H, m), 7.58-7.74 (4H, m), 7.21 (2H, s). MS (M+H) 476.9. mp 261.8° C. with decomposition. Elemental Analysis: theory C 52.83, H 2.96, N 5.87; found C 52.71, H 3.05, N 5.71.

Example 6

2-Amino-4-chloro-benzenethiol hydrochloride (6). By the procedure of Danley et al. (1965) Can. J. Chem. 43:2610-2612, sodium tetrasulfide was obtained by dissolving sulfur (Aldrich, 9.6 g, 300 mmol) in molten sodium sulfide nonahydrate (Aldrich, 24.0 g, 100 mmol). This hot liquid was added to a solution of 2,5-dichloronitrobenzene (Aldrich, 38.4 g, 200 mmol) in 95% ethanol (140 mL). After the exothermic reaction had ceased, the mixture was refluxed for 2 hours and filtered while hot. The precipitate was washed with water (50 mL) and ethanol (50 mL) to give 37.7 g of intermediate trisulfide as a yellow solid. $^1$H NMR (CDCl$_3$) δ 8.83 (d, J=2.3 Hz, 1H), 7.76 (d, J=8.6 Hz, 1H), 7.55 (dd, J=8.6, 2.3 Hz, 1H).

Concentrated hydrochloric acid (125 mL) was slowly (overnight, 15 hours) added to a well-stirred suspension of the trisulfide (37.7 g) described above and tin (Aldrich, 88 g, 737 mmol) in 95% ethanol (200 mL). After filtration of the hot solution, the filtrate was allowed to stand at room temperature overnight to precipitate the crude product. The precipitate was collected by filtration, washed with 1:1 ethanol/concentrated HCl. Recrystallization from 1:1 MeOH/concentrated HCl gave compound 6 (13.8 g) as white needles. $^1$H NMR (DMSO-d$_6$) δ 6.96 (d, J=8.3 Hz, 1H), 6.86 (d, J=2.3 Hz, 1H), 6.50 (dd, J=8.3, 2.3 Hz, 1H).

Example 7

2-Amino-4-methyl-benzenethiol hydrochloride (7). bis-(4-Methyl-2-nitrophenyl)-trisulfide was prepared using the method in Example 6, starting from 4-chloro-3-nitro-toluene (Aldrich, 34.3 g, 200 mmol), sulfur (Aldrich, 9.6 g, 300 mmol) and sodium sulfide nonahydrate (Aldrich, 24.0 g, 100 mmol) in 95% EtOH (150 mL). 27.7 g of the trisulfide was obtained as a yellow solid. $^1$H NMR (400 MHz, CDCl$_3$) δ 8.21 (d, J=8.3 Hz, 1H), 8.07 (br s, 1H), 7.58 (dd, J=8.3, 1.3 Hz, 1H), 2.48 (s, 3H).

Reduction of the bis-(4-Methyl-2-nitrophenyl)trisulfide as in Example 6 gave compound 7 (11.3 g) as a mixture after recrystallization, but which was used directly in subsequent reactions.

Example 8

5-Chloro-2-(2,6-dichloro-4-nitro-benzyl)-benzothiazole (8). By a modification of the procedure of D. L. Boger (*J. Org. Chem.* 43:2296-2297 (1978)) a solution of $P_2O_5/MeSO_3H$ (Aldrich, 7.5 g, 1:10, w:w) was treated with 2-amino-4-chlorobenzenethiol hydrochloride (Example 6, 1.96 g, 10.0 mmol) and (2,6-dichloro-4-nitro-phenyl)-acetic acid (2.50 g, 10.0 mmol). The resulting mixture was stirred at room temperature for 1 hour, then heated at 90° C. overnight (15 hours). After cooled to room temperature, the reaction mixture was poured to ice and the resulting mixture was extracted 3× with EtOAc (50 mL). The organic layers were combined and washed twice with a brine solution (100 mL), dried over $Na_2SO_4$, and concentrated under vacuum. The crude solid was chromatographed ($CH_2Cl_2$) to yield 3.7 g (99%) of compound 8 as a pale yellow solid. $^1$H NMR (CDCl$_3$) δ 8.28 (s, 2H), 7.98 (d, J=1.9 Hz, 1H), 7.76 (d, J=8.5 Hz, 1H), 7.38 (dd, J=8.5, 1.9 Hz, 1H), 4.87 (s, 2H). MS (M+H) 373.

The compounds of Table 2 were prepared using the method of Example 8.

TABLE 2

| Compound | A | B |
|---|---|---|
| 8 | Cl | Cl |
| 9 | Cl | H |
| 10 | CF$_3$ | Cl |
| 11 | CF$_3$ | H |
| 12 | H | Cl |
| 13 | H | H |
| 14 | Me | Cl |
| 15 | Me | H |

Example 9

5-Chloro-2-(2-chloro-4-nitro-benzyl)-benzothiazole (9).
$^1$H NMR (400 MHz, DMSO-d$_6$) δ 8.35 (d, J=2.3 Hz, 1H), 8.25 (dd, J=8.5, 2.4 Hz, 1H), 8.10 (d, J=8.6 Hz, 1H), 8.02 (d, J=2.0 Hz, 1H), 7.89 (d, J=8.5 Hz, 1H), 7.48 (dd, J=8.6, 2.0 Hz, 1H), 4.77 (s, 2H). MS (M+H) 339.

Example 10

2-(2,6-Dichloro-4-nitro-benzyl)-5-trifluoromethyl-benzothiazole (10).
$^1$H NMR (DMSO-d$_6$) δ 8.42 (s, 2H), 8.34 (d, J=8.4 Hz, 1H), 8.28 (br s, 1H), 7.76 (d, J=8.4 Hz, 1H), 4.94 (s, 2H). MS (M+H) 407.

Example 11

2-(2-Chloro-4-nitro-benzyl)-5-trifluoromethyl-benzothiazole (11). $^1$H NMR (CDCl$_3$) δ 8.33 (d, J=2.3 Hz, 1H), 8.27 (br s, 1H), 8.14 (dd, J=8.5, 2.3 Hz, 1H), 7.96 (br d, J=8.3 Hz, 1H), 7.63 (d, J=8.5 Hz, 2H) 4.70 (s, 2H). MS (M+H) 371.

Example 12

2-(2,6-Dichloro-4-nitro-benzyl)-benzothiazole (12). $^1$H NMR (DMSO-d$_6$) δ 8.41 (s, 2H), 8.06 (d, J=8.0 Hz, 1H), 7.90 (d, J=7.9 Hz, 1H), 7.50-7.38 (m, 2H), 4.94 (s, 2H). MS (M−H) 337.

Example 13

2-(2-Chlor-4-nitrobenzyl)-benzothiazole (13). $^1$H NMR (CDCl$_3$) δ 8.35 (d, J=2.2 Hz, 1H), 8.25 (dd, J=8.4, 2.2 Hz, 1H), 8.05 (d, J=7.9 Hz, 1H), 7.93 (d, J=8.1 Hz, 1H), 7.3 (d, J=8.5 Hz, 1H), 7.49 (t, J=7.9 Hz, 1H), 7.42 (t, J=7.6 Hz, 1H), 4.76 (s, 2H). MS (M+H) 305.

Example 14

2-(2,6-Dichloro-4-nitro-benzyl)-5-methyl-benzothiazole (14). $^1$H NMR (DMSO-d$_6$) δ 8.41 (s, 2H), 7.91 (d, J=8.2 Hz, 1H), 7.71 (br s, 1H), 7.25 (d, J=8.2 Hz, 1H), 4.85 (s, 2H), 2.41 (s, 3H). MS (M+H) 353.

Example 15

2-(2-Chloro-4-nitro-benzyl)-5-methyl-benzothiazole (15). $^1$H NMR (DMSO-d$_6$) δ 8.35 (d, J=2.3 Hz, 1H), 8.24 (dd, J=8.5, 2.3 Hz, 1H), 7.91 (d, J=8.2 Hz, 1H), 7.85 (d, J=8.5 Hz, 1H), 7.74 (br s, 1H), 7.25 (dd, J=8.2, 1.0 Hz, 1H), 4.73 (s, 2H), 2.42 (s, 3H). MS (M−H) 317.

Examples 16-23

The compounds of Table 2 were reduced to the anilines of Table 3 using one of the methods described below, as indicated in Table 3.

Method A. To a solution of the nitro compound in ethyl acetate (0.1 M) at reflux was added tin (II) dichloride dihydrate (5 equiv.). After 0.5 to 2 h at reflux, the hot mixture is poured into a separatory funnel containing 2× the volume of ethyl acetate and 50 equiv. of 1N KOH, freshly prepared and still warm. The mixture is rapidly extracted and separated. The organic layer is washed with brine, dried over MgSO$_4$ and concentrated to give aniline which can usually be used directly in the next step.

Method B. See Example 39.

Method C. To a solution of nitro compound (7 mmol) in isopropanol (50 mL)/THF (20 mL) was added a slurry (0.5 mL) of Raney Nickel in water. The reaction was stirred under an atmosphere of hydrogen at ambient pressure and temperature for 24 h. After filtration through a Celite plug, the solution was concentrated under vacuum to afford the desired aniline. The residual Raney Nickel on the Celite plug was suspended in halogenated solvent for deactivation.

TABLE 3

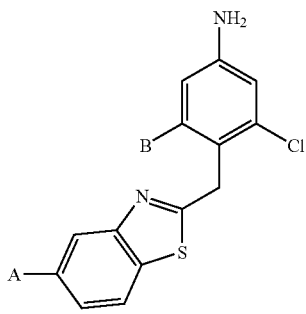

| Compound | A | B | Method |
|---|---|---|---|
| 16 | Cl | Cl | A |
| 17 | Cl | H | B |
| 18 | CF$_3$ | Cl | A |
| 19 | CF$_3$ | H | B |
| 20 | H | Cl | B |
| 21 | H | H | B |
| 22 | Me | Cl | B |
| 23 | Me | H | B |

Example 16

3,5-Dichloro-4-(5-chloro-benzothiazol-2-ylmethyl)-phenylamine (16). $^1$H NMR (DMSO-d$_6$) δ 8.03 (d, J=8.4 Hz, 1H), 8.01 (d, J=2.1 Hz, 1H), 7.45 (dd, J=8.5, 2.2 Hz, 1H), 6.70 (s, 2H), 5.79 (s, 2H), 4.52 (s, 2H). MS (M+H) 343.

Example 17

3-Chloro-4-(5-chloro-benzothiazol-2-ylmethyl)phenylamine (17). $^1$H NMR (DMSO-d$_6$) δ 8.05-7.95 (m, 2H), 7.43 (dd, J=8.5, 2.1 Hz, 1H), 7.17 (d, J=8.2 Hz, 1H), 6.66 (d, J=2.2 Hz, 1H), 6.53 (dd, J=8.2, 2.2 Hz, 1H), 5.44 (s, 2H), 4.36 (s, 2H). MS (M+H) 309.

Example 18

3,5-Dichloro-4-(5-trifluoromethyl-benzothiazol-2-ylmethyl)-phenylamine (18). $^1$H NMR (DMSO-d$_6$) δ 8.29 (br s, 1H), 8.26 (d, J=8.4 Hz, 1H), 7.72 (d, J=8.4 Hz, 1H), 6.70 (s, 2H), 5.81 (s, 2H), 4.56 (s, 2H). MS (M+H) 377.

Example 19

3-Chloro-4-(5-trifluoromethyl-benzothiazol-2-ylmethyl)-phenylamine (19). $^1$H NMR (DMSO-d$_6$) δ 8.25 (br s, 1H), 8.26 (d, J=8.4 Hz, 1H), 7.72 (dd, J=8.4, 1.3 Hz, 1H), 7.19 (d, J=8.2 Hz, 1H), 6.67 (d, J=2.2 Hz, 1H), 6.54 (dd, J=8.2, 2.2 Hz, 1H), 5.46 (s, 2H), 4.40 (s, 2H). MS (M+H) 343.

Example 20

4-Benzothiazol-2-ylmethyl-3,5-dichloro-phenylamine (20). $^1$H NMR (DMSO-d$_6$) δ 7.99 (dd, J=8.0, 0.6 Hz, 1H), 7.92 (d, J=8.1 Hz, 1H), 7.45 (td, J=8.2, 1.2 Hz, 1H), 7.38 (td, J=8.0, 1.0 Hz, 1H), 6.70 (s, 2H), 5.78 (s, 2H), 4.51 (s, 2H). MS (M+H) 309.

Example 21

4-Benzothiazol-2-ylmethyl-3-chloro-phenylamine (21). $^1$H NMR (DMSO-d$_6$) δ 7.98 (d, J=8.0 Hz, 1H), 7.92 (d, J=8.0 Hz, 1H), 7.47 (td, J=7.9, 1.2 Hz, 1H), 7.38 (td, J=7.9, 1.0 Hz, 1H), 7.17 (d, J=8.3 Hz, 1H), 6.66 (d, J=2.2 Hz, 1H), 6.54 (dd, J=8.2, 2.2 Hz, 1H), 5.44 (s, 2H), 4.35 (s, 2H). MS (M+H) 275.

Example 22

3,5-Dichloro-4-(5-methyl-benzothiazol-2-ylmethyl)-phenylamine (22). $^1$H NMR (DMSO-d$_6$) δ 7.84 (d, J=8.2 Hz, 1H), 7.73 (br s, 1H), 7.21 (dd, J=8.2, 1.0 Hz, 1H), 6.69 (s, 2H), 5.77 (s, 2H), 4.48 (s, 2H), 2.43 (s, 3H). MS (M+H) 323.

Example 23

3-Chloro-4-(5-methyl-benzothiazol-2-ylmethyl)-phenylamine (23). $^1$H NMR (DMSO-d$_6$) δ 7.84 (d, J=8.2 Hz, 1H), 7.73 (s, 1H), 7.21 (d, J=8.2 Hz, 1H), 7.15 (d, J=8.2 Hz, 1H), 6.65 (d, J=2.1 Hz, 1H), 6.52 (dd, J=8.2, 2.1 Hz, 1H), 5.41 (s, 2H), 4.32 (s, 2H), 2.43 (s, 3H). MS (M+H) 289.

The compounds of Table 4 were prepared using conventional methods from compounds in Table 3 and corresponding arylsulfonyl chloride.

TABLE 4

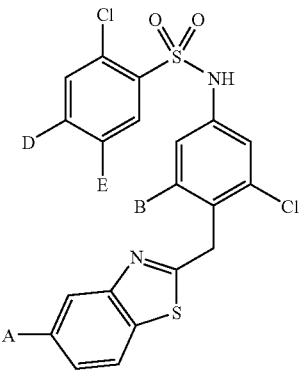

| Compound | A | B | D | E |
|---|---|---|---|---|
| 24 | Cl | Cl | CF$_3$ | H |
| 25 | Cl | Cl | Cl | H |
| 26 | Cl | Cl | Cl | Me |
| 27 | Cl | H | CF$_3$ | H |
| 28 | CF$_3$ | Cl | CF$_3$ | H |
| 29 | CF$_3$ | Cl | Cl | H |
| 30 | CF$_3$ | H | CF$_3$ | H |
| 31 | CF$_3$ | H | Cl | H |
| 32 | H | Cl | CF$_3$ | H |
| 33 | H | Cl | Cl | H |
| 34 | H | Cl | Cl | Me |
| 35 | H | H | CF$_3$ | H |
| 36 | Me | Cl | CF$_3$ | H |
| 37 | Me | H | CF$_3$ | H |

Example 24

2-Chloro-N-[3,5-dichloro-4-(5-chloro-benzothiazol-2-ylmethyl)-phenyl]-4-trifluoromethyl-benzenesulfonamide (24). $^1$H NMR (DMSO-d$_6$) δ 11.56 (br s, 1H), 8.35 (d, J=8.2 Hz, 1H), 8.20 (d, J=1.1 Hz, 1H), 8.03 (d, J=8.6 Hz, 1H), 8.00-7.95 (m, 2H), 7.45 (dd, J=8.6, 2.1 Hz, 1H), 7.23 (s, 2H), 4.62 (s, 2H). MS (M−H) 583.

Example 25

2,4-Dichloro-N-[3,5-dichloro-4-(5-chloro-benzothiazol-2-ylmethyl)-phenyl]-benzenesulfonamide (25). $^1$H NMR (DMSO-d$_6$) δ 11.40 (br s, 1H), 8.14 (d, J=8.6 Hz, 1H), 8.05

(d, J=8.6 Hz, 1H), 8.02 (d, J=2.0 Hz, 1H), 7.94 (d, J=2.1 Hz, 1H), 7.70 (dd, J=8.6, 2.1 Hz, 1H), 7.46 (dd, J=8.6, 2.0 Hz, 1H), 7.20 (s, 2H), 4.62 (s, 2H). MS (M−H) 549.

Example 26

2,4-Dichloro-N-[3,5-dichloro-4-(5-chloro-benzothiazol-2-ylmethyl)-phenyl]-5-methyl-benzenesulfonamide (26). $^1$H NMR (DMSO-d$_6$) δ 11.33 (br s, 1H), 8.28 (s, 1H), 8.17 (s, 1H), 8.04 (d, J=8.6 Hz, 1H), 8.01 (d, J=1.9 Hz, 1H), 7.87 (s, 1H), 7.45 (dd, J=8.6, 1.9 Hz, 1H), 7.22 (s, 2H), 4.61 (s, 2H), 2.40 (s, 3H). MS (M−H) 563.

Example 27

2-Chloro-N-[3-chloro-4-(5-chloro-benzothiazol-2-ylmethyl)-phenyl]-4-trifluoromethyl-benzenesulfonamide (27). $^1$H NMR (DMSO-d$_6$) δ 11.24 (br s, 1H), 8.29 (d, J=8.3 Hz, 1H), 8.16 (br s, 1H), 8.02 (d, J=8.6 Hz, 1H), 8.00 (d, J=1.8 Hz, 1H), 7.96 (d, J=8.3 Hz, 1H), 7.45 (d, J=8.3 Hz, 2H), 7.20 (d, J=2.0 Hz, 1H), 7.10 (dd, J=8.4, 2.0 Hz, 1H), 4.47 (s, 2H). MS (M−H) 549.

Example 28

2-Chloro-N-[3,5-dichloro-4-(5-trifluoromethyl-benzothiazol-2-ylmethyl)-phenyl]-4-trifluoromethyl-benzenesulfonamide (28). $^1$H NMR (DMSO-d$_6$) δ 11.56 (s, 1H), 8.35 (d, J=8.2 Hz, 1H), 8.27 (d, J=8.3 Hz, 1H), 8.26 (br s, 1H), 8.20 (br s, 1H), 7.99 (dd, J=8.3, 1.0 Hz, 1H), 7.73 (dd, J=8.2, 1.2 Hz, 1H), 7.24 (s, 2H), 4.67 (s, 2H). MS (M−H) 617.

Example 29

2,4-Dichloro-N-[3,5-dichloro-4-(5-trifluoromethyl-benzothiazol-2-ylmethyl)-phenyl]-benzenesulfonamide (29). $^1$H NMR (DMSO-d$_6$) δ 11.41 (s, 1H), 8.29 (br s, 1H), 8.27 (d, J=8.6 Hz, 1H), 8.15 (d, J=8.6 Hz, 1H), 7.94 (d, J=2.0 Hz, 1H), 7.73 (dd, J=8.4, 1.4 Hz, 1H), 7.70 (dd, J=8.6, 2.0 Hz, 1H), 7.21 (s, 2H), 4.67 (s, 2H). MS (M−H).

Example 30

2-Chloro-N-[3-chloro-4-(5-trifluoromethyl-benzothiazol-2-ylmethyl)-phenyl]-4-trifluoromethyl-benzenesulfonamide (30). $^1$H NMR (DMSO-d$_6$) δ 11.25 (br s, 1H), 8.32-8.22 (m, 3H), 8.16 (br s, 1H), 7.96 (d, J=8.4 Hz, 1H), 7.72 (d, J=8.4 Hz, 1H), 7.46 (d, J=8.3 Hz, 1H), 7.21 (s, 1H), 7.11 (d, J=8.4 Hz, 1H), 4.52 (s, 2H). MS (M−H) 583.

Example 31

2,4-Dichloro-N-[3-chloro-4-(5-trifluoromethyl-benzothiazol-2-ylmethyl)-phenyl]-benzenesulfonamide (31). $^1$H NMR (DMSO-d$_6$) δ 11.10 (br s, 1H), 8.28 (br s, 1H), 8.26 (d, J=8.5 Hz, 1H), 8.08 (d, J=8.5 Hz, 1H), 7.89 (d, J=2.0 Hz, 1H), 7.72 (dd, J=8.4, 1.4 Hz, 1H), 7.65 (dd, J=8.6, 2.1 Hz, 1H), 7.46 (d, J=8.4 Hz, 1H), 7.18 (d, J=2.2 Hz, 1H), 7.10 (dd, J=8.3, 2.2 Hz, 1H), 4.52 (s, 2H). MS (M−H) 549.

Example 32

N-(4-Benzothiazol-2-ylmethyl-3,5-dichloro-phenyl)-2-chloro-4-trifluoromethyl-benzenesulfonamide (32). $^1$H NMR (DMSO-d$_6$) δ 11.54 (s, 1H), 8.35 (d, J=8.3 Hz, 1H), 8.20 (br s, 1H), 7.99 (d, J=8.3 Hz, 2H), 7.88 (d, J=7.8 Hz, 1H), 7.46 (td, J=8.0, 1.0 Hz, 1H), 7.40 (td, J=7.8, 0.9 Hz, 1H), 7.23 (s, 2H), 4.61 (s, 2H). MS (M−H) 549.

Example 33

N-(4-Benzothiazol-2-ylmethyl-3,5-dichloro-phenyl)-2,4-dichloro-benzenesulfonamide (33). $^1$H NMR (DMSO-d$_6$) δ 11.38 (s, 1H), 8.14 (d, J=8.6 Hz, 1H), 8.00 (d, J=7.9 Hz, 1H), 7.94 (d, J=2.0 Hz, 1H), 7.90 (d, J=8.0 Hz, 1H), 7.70 (dd, J=8.6, 2.0 Hz, 1H), 7.46 (m, 1H), 7.40 (m, 1H), 7.20 (s, 2H), 4.60 (s, 2H). MS (M−H) 515.

Example 34

N-(4-Benzothiazol-2-ylmethyl-3,5-dichloro-phenyl)-2,4-dichloro-5-methyl-benzenesulfonamide (34). $^1$H NMR (DMSO-d$_6$) δ 11.32 (s, 1H), 8.17 (s, 1H), 8.00 (d, J=7.9 Hz, 1H), 7.90 (d, J=8.1 Hz, 1H), 7.88 (s, 1H), 7.46 (t, J=7.3 Hz, 1H), 7.39 (t, J=7.4 Hz, 1H), 7.16 (s, 2H), 4.60 (s, 2H), 2.40 (s, 3H). MS (M−H) 531.

Example 35

N-(4-Benzothiazol-2-ylmethyl-3-chloro-phenyl)-2-chloro-4-trifluoromethyl-benzenesulfonamide (35). $^1$H NMR (DMSO-d$_6$) δ 11.23 (br s, 1H), 8.29 (d, J=8.3 Hz, 1H), 8.15 (br s, 1H), 7.98 (d, J=7.9 Hz, 1H), 7.96 (d, J=8.4 Hz, 1H), 7.90 (d, J=8.1 Hz, 1H), 7.46 (td, J=7.9, 1.0 Hz, 1H), 7.44 (d, J=7.8 Hz, 1H), 7.38 (t, J=7.7 Hz, 1H), 7.20 (d, J=2.1 Hz, 1H), 7.11 (dd, J=8.3, 2.1 Hz, 1H), 4.46 (s, 2H). MS (M−H) 517.

Example 36

2-Chloro-N-[3,5-dichloro-4-(5-methyl-benzothiazol-2-ylmethyl)-phenyl]-4-trifluoromethyl-benzenesulfonamide (36). $^1$H NMR (DMSO-d$_6$) δ 11.54 (s, 1H), 8.36 (d, J=8.2 Hz, 1H), 8.19 (br s, 1H), 8.00 (dd, J=8.2, 1.0 Hz, 1H), 7.84 (d, J=8.2 Hz, 1H), 7.70 (br s, 1H), 7.26-7.18 (m, 3H), 4.58 (s, 2H), 2.40 (s, 3H). MS (M−H) 563.

Example 37

2-Chloro-N-[3-chloro-4-(5-methyl-benzothiazol-2-ylmethyl)-phenyl]-4-trifluoromethyl-benzenesulfonamide (37). $^1$H NMR (DMSO-d$_6$) δ 11.22 (br s, 1H), 8.19 (d, J=8.2 Hz, 1H), 8.15 (br s, 1H), 7.45 (dd, J=8.3, 1.1 Hz, 1H), 7.83 (d, J=8.2 Hz, 1H), 7.71 (br s, 1H), 7.43 (d, J=8.4 Hz, 1H), 7.24-7.19 (m, 2H), 7.05 (dd, J=8.5, 2.2 Hz, 1H), 4.43 (s, 2H), 2.41 (s, 3H). MS (M−H) 529.

Example 38

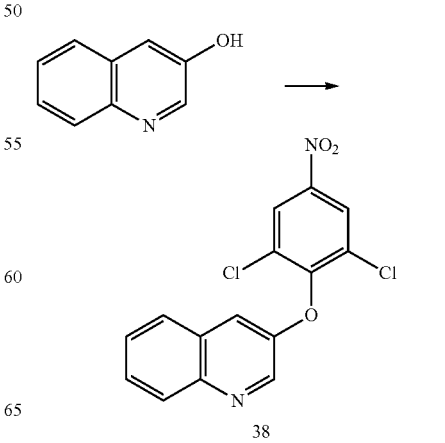

38

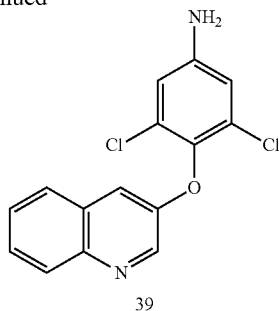

39

3-Hydroxyquinoline (prepared according to the procedure of Naumann, et. al., *Synthesis*, 1990, 4, 279-281)) (3 g) and 1,2,3-trichloro-5-nitrobenzene (4.7 g) were dissolved in DMF (80 mL) and heated with cesium carbonate (7.4 g) for 2 h at 60° C. The reaction was poured into ice/water (500 mL). The resulting off-white precipitate was collected by filtration and rinsed with hexane to afford compound 38 as a solid (6.9 g) suitable for use in the next reaction. $^1$H NMR in CDCl$_3$ 8.863 (d, J=2.2 Hz, 1H), 8.360 (s, 2H), 8.106 (d, J=8.6 Hz, 1H), 7.646 (m, 2H), 7.529 (d, J=8.6 Hz, 1H), 7.160 (d, J=2.2 Hz, 1H).

Example 39

To a solution of compound 38 (6.9 g) in ethanol/THF/water (ratio 40:20:10) was added ammonium chloride (3.3 g) and powdered iron (3.4 g). This mixture was heated to reflux for 5 h. The hot mixture was then filtered through Celite and concentrated. The residue was dissolved in ethyl acetate and washed with saturated NaHCO$_3$ solution followed by water and then brine. The solution was dried over magnesium sulfate and concentrated to afford compound 39 as an off-white solid (5.6 g). $^1$H NMR in (DMSO) δ 8.846 (d, J=2.9 Hz, 1H), 8.010 (m, 1H), 7.915 (m, 1H), 7.645 (m, 1H), 7.560 (m, 1H), 7.401 (d, J=2.9 Hz, 1H), 6.778 (s, 2H), 5.762 (s, 2H).

Treatment of the aniline 39 with various sulfonyl chlorides according to conventional methods gave the sulfonamides 40-44 of Table 5.

TABLE 5

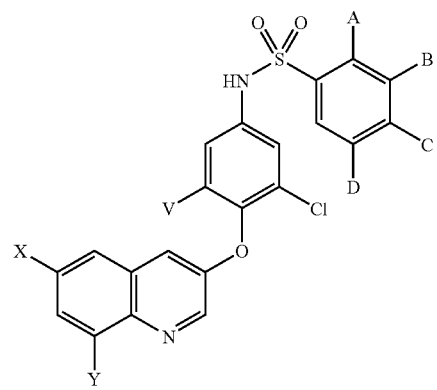

| Compound | X | Y | V | A | B | C | D |
|---|---|---|---|---|---|---|---|
| 40 | H | H | Cl | CF$_3$ | H | Cl | H |
| 41 | H | H | Cl | Cl | H | CF$_3$ | H |
| 42 | H | H | Cl | Cl | H | Cl | H |
| 43 | H | H | Cl | Cl | H | Cl | Me |
| 44 | H | H | H | Cl | H | Cl | H |

TABLE 5-continued

| Compound | X | Y | V | A | B | C | D |
|---|---|---|---|---|---|---|---|
| 45 | CO$_2$Me | H | Cl | Cl | H | Cl | H |
| 46 | H | CO$_2$Me | Cl | Cl | H | Cl | H |
| 47 | H | Cl | Cl | H | Cl | H | |
| 48 | H | CO$_2$H | Cl | Cl | H | Cl | H |
| 49 | Me | H | Cl | Cl | H | Cl | Me |
| 50 | H | H | F | Cl | H | Cl | Me |

Example 40

$^1$H NMR (DMSO) δ 11.4-11.6 (1H, broad), 8.87 (1H, d, J=2.9 Hz), 8.15-8.22 (2H, m), 8.00-8.08 (2H, m), 7.87 (1H, d, J=8.0 Hz), 7.55-7.68 (2H, m), 7.47 (1H, d, J=2.9 Hz), 7.35 (2H, s). MS (M−H) 545. mp 98.8° C.

Example 41

$^1$H NMR (DMSO) δ 11.58 (1H, s), 8.86 (1H, d, J=2.9 Hz), 8.38 (1H, d, J=8.4 Hz), 8.23 (1H, s), 8.01 (1H, d, J=8.4 Hz), 7.86 (1H, d, J=8.1 Hz), 7.53-7.68 (2H, m), 7.46 (1H, d, J=2.9 Hz), 7.34 (2H, s). MS (M−H) 545.0.

Example 42

$^1$H NMR (d$_6$-acetone) δ 9.9 (1H, br s), 8.794 (1H, d, J=2.9 Hz), 8.23 (1H, d, J=8.4 Hz), 8.035 (1H, br d, J=8.4 Hz), 7.793 (1H, d, J=1.5 Hz), 7.78 (1H, m), 7.62-7.70 (2H, m), 7.57 (1H, td, J=6.8, 1.2 Hz), 7.476 (2H, s), 7.364 (1H, d, J=2.6 Hz). MS (M−H) 511.0.

Example 43

$^1$H NMR (300 MHz/CDCl$_3$) δ 2.43 (3H, s), 7.10 (1H, d, J=3 Hz), 7.26 (2H, s), 7.48-7.64 (4H, m), 7.96 (1H, s), 8.09 (1H, d, J=8.7 Hz), 8.78 (1H, d, J=3 Hz). MS (M+H) 527. mp 233-235° C.

Example 44

$^1$H NMR (300 MHz/CDCl$_3$) δ 7.14 (1H, dd, J=2.6 Hz, J=8.9 Hz), 7.26 (1H, d, J=8.9 Hz), 7.33 (1H, d, J=2.6 Hz), 7.56-7.58 (2H, m), 7.66-7.69 (2H, m), 7.87 (1H, m), 7.93 (1H, d, J=2.0 Hz), 8.00 (1H, m), 8.09 (1H, d, J=8.5 Hz), 8.80 (1H, d, J=2.9 Hz), 11.06 (1H, brs). MS (M+H)) 479. mp 122° C.

Example 45

3-[2,6-Dichloro-4-(2,4-dichloro-benzenesulfonylamino)-phenoxy]-quinoline-6-carboxylic acid methyl ester (45). A solution of 3-(4-amino-2,6-dichloro-phenoxy)-quinoline-6-carboxylic acid methyl ester (96) (0.93 mmol) and 2,4-dichlorobenzenesulfonyl chloride (250 mg, 1.02 mmol) in pyridine (0.13 mL, 1.53 mmol) $CH_2Cl_2$ (3.7 mL) was stirred at room temperature for 12 h. Sat $NaHCO_3$ was added to the reaction mixture, which was then extracted twice with AcOEt. Organic layer was washed by brine, dried over anhydrous $MgSO_4$, and concentrated. Crude residue was purified by column chromatography (hexane/AcOEt=2/1, 80 g of silica gel) to afford compound 45 (237 mg, 41%, in 3 steps). $^1H$ NMR (300 MHz, DMSO-$d_6$) δ 3.90 (3H, s), 7.31 (2H, s), 7.72 (1H, dd, J=1.8, 7.8 Hz), 7.79 (1H, d, J=3.0 Hz), 7.96 (1H, d, J=1.8 Hz), 8.11 (2H, s), 8.18 (1H, d, J=7.8 Hz), 8.64 (1H, s), 8.99 (1H, d, J=3.0 Hz), 11.42 (1H, br s). MS (M+H) 571.

Example 46

3-[2,6-Dichloro-4-(2,4-dichloro-benzenesulfonylamino)-phenoxy]-quinoline-8-carboxylic acid methyl ester (46). To a solution of 3-(4-Amino-2,6-dichloro-phenoxy)-quinoline-8-carboxylic acid methyl ester (99) (1.26 mmol) in pyridine (0.15 mL, 1.80 mmol) and $CH_2Cl_2$ (5 mL), was added 2,4-Dichlorolbenzenesulfonyl chloride (381 mg, 1.55 mmol). The mixture was stirred at room temperature for 12 h. Sat $NaHCO_3$ was added to the reaction mixture, which was then extracted twice with AcOEt. Organic layer was washed by brine, dried over $MgSO_4$, and concentrated. The crude residue was purified by column chromatography (hexane/AcOEt=2/1, 80 g of silica gel) to afford compound 46 (506 mg, 70%) as a white solid. $^1H$ NMR (300 MHz, DMSO-$d_6$) δ 3.91 (3H, s), 7.31 (2H, s), 7.57-7.65 (2H, m), 7.72 (1H, dd, J=2.1, 8.6 Hz), 7.83 (1H, d, J=8.6 Hz), 7.96 (2H, d, J=2.1 Hz), 8.03 (1H, d, J=8.6 Hz), 8.18 (1H, d, J=8.6 Hz), 8.94 (1H, d, J=2.1 Hz), 11.4 (1H, br s), MS (M+H) 571.

Example 47

3-[2,6-Dichloro-4-(2,4-dichloro-benzenesulfonylamino)-phenoxy]-quinoline-6-carboxylic acid (47). To a solution of 3-[2,6-Dichloro-4-(2,4-dichloro-benzenesulfonylamino)-phenoxy]-quinoline-6-carboxylic acid methyl ester (45) (200 mg, 0.35 mmol) in THF/MeOH (2 mL/2 mL) was added 4N NaOH (0.1 mL, 0.4 mmol). This mixture was refluxed for 2.5 h. The reaction mixture was cooled to room temperature and was neutralized with 2N HCl, and then concentrated. The residue was extracted twice with AcOEt. Organic layer was washed by brine, dried over anhydrous $MgSO_4$, and concentrated to give a solid. Crude product was recrystallized by hexane/AcOEt to afford compound 47 (153 mg, 78%). $^1H$ NMR (300 MHz, DMSO-$d_6$) δ 7.16 (2H, s), 7.62 (1H, dd, J=2.0, 8.5 Hz), 7.73 (1H, d, J=2.9 Hz), 7.82 (1H, s), 8.08-8.11 (3H, m), 8.60 (1H, s), 8.95 (1H, d, J=2.9 Hz), 13.2 (1H, br s), MS (M+H) 557. mp 228-2.

Example 48

3-[2,6-Dichloro-4-(2,4-dichloro-benzenesulfonylamino)-phenoxy]-quinoline-8-carboxylic acid (48). To a solution of 3-[2,6-Dichloro-4-(2-chloro-4-trifluoromethyl-benzenesulfonylamino)-phenoxy]-quinoline-8-carboxylic acid methyl ester (47) (402 mg, 0.7 mmol) in THF/MeOH=0.1 mL/0.3 mL was added 4N NaOH (0.2 mL, 0.77 mmol). The mixture was refluxed for 12 h. After cooling to room temperature the reaction mixture was filtered to remove insoluble materials. The filtrate was concentrated and the residue was dissolved in aq $NH_4Cl$ and extracted twice with AcOEt. Organic layer was washed by brine, and dried over anhydrous $MgSO_4$, and concentrated to afford compound 48 (197 mg, 50%) as a white solid. $^1H$ NMR (300 MHz, DMSO-$d_6$) δ 7.32 (2H, s), 7.70-7.81 (2H, m), 7.90 (1H, d, J=2.2 Hz), 7.96 (1H, d, J=2.2 Hz), 8.17-8.19 (1H, m), 8.22-8.24 (1H, m), 8.38-8.39 (1H, m), 9.11 (1H, d, J=2.2 Hz), 11.4 (1H, br s), 15.4 (1H, br s). MS (M+H) 557. mp 263-266° C.

Example 49

2,4-Dichloro-N-[3,5-dichloro-4-(6-methyl-quinoln-3-yloxy)-phenyl]-5-methyl-benzenesulfonamide (49). To a solution of 3,5-Dichloro-4-(6-methyl-quinlin-3-yloxy)-phenylamine (100) (400 mg, 1.25 mmol) in pyridine (0.12 mL, 1.48 mmol)-$CH_2Cl_2$ (4 mL) was added 2,4-dichloro-5-methylbenzenesulfonyl chloride (325 mg, 1.25 mmol). The mixture was stirred at room temperature for 12 h. The reaction mixture was concentrated and the residue was purified by column chromatography (hexane/AcOEt=2/1, 80 g of silica gel) to provide compound (49) (453 mg, 66%) as a white solid. $^1H$ NMR (300 MHz, DMSO-$d_6$) δ 2.41 (3H, s), 2.44 (3H, s), 7.31 (3H, s), 7.49 (1H, d, J=8.7 Hz), 7.61 (1H, s), 7.88-7.91 (2H, m), 8.19 (1H, s), 8.74 (1H, d, J=3.0 Hz), 11.3 (1H, br s), MS (M+H) 541. mp 228-230° C.

Example 50

Part 1
3-Chloro-5-fluoro-4-(quinolin-3-yloxy)nitrobenzene (50.1). To a solution of 3,4-difluoronitrobenzene 1.00 g in conc. $H_2SO_4$ (20 mL), was added portionwise $Cl_2O$ in $CCl_4$ (25 mL, prepared as described by Cady G. H. et al. in *Inorg. Synth.* Vol. 5, p. 156 (1957)). The mixture was stirred at room temperature overnight. The mixture was poured into crashed ice and extracted with $Et_2O$ (30 mL×3). Combined ether layers were washed with 10% $Na_2SO_3$ and brine, and dried over $Na_2SO_4$. The solvent was concentrated to about 10 mL (this solution contains 3-chloro-4,5-difluoronitrobenzene). This solution was diluted with acetone (60 mL), and then 3-hydroxyquinoline 0.75 g and $K_2CO_3$ 2.2 g were added to this solution. The mixture was heated to reflux for 1.5 h. After cooling the reaction mixture was filtered through a short celite pad. The filtrate was concentrated to give an oil, which was then purified by column chromatography (silica gel, AcOEt:hexane=1:5) to provide the intermediate compound 50.1 (0.980 g) as a yellow oil.

Part 2
3-Chloro-5-fluoro-4-(quinolin-3-yloxy)phenylamine (50.2). To a solution of 3-chloro-5-fluoro-4-(quinolin-3-yloxy)nitrobenzene (50.1) (0.980 g) and $NH_4Cl$ (1.64 g) in EtOH (50 mL)—$H_2O$ (5 mL), was added iron powder (1.92 g). The mixture was heated to reflux for 1 h. After cooling the reaction mixture was filtered through short celite pad. The filtrate was concentrated, diluted with sat. $NaHCO_3$ and extracted with AcOEt (30 mL×3). The combined organic layers were washed with brine and dried over $Na_2SO_4$. Concentration of solvent afford crude product, which was purified by column chromatography (silica gel, AcOEt:hexane=1:3) to provide aniline 50.2 (0.420 g) as a colorless solid.

Part 3
N-[3-Chloro-5-fluoro-4-(quinolin-3-yloxy)phenyl]-2,4-dichloro-5-methyl-benzenesulfonamide (50). To a solution of 3-chloro-5-fluoro-4-(quinolin-3-yloxy)phenylamine (50.2) (0.420 g) in pyridine (2.2 mL), was added 2,4-dichloro-5-methylbenzenesulfonylchloride 0.360 g. The mixture was stirred at room temperature for 1 h. The reaction mixture was purified directly by column chromatography (silica gel, AcOEt:hexane=1:3). The product was triturated by hexane to give title compound (0.522 g). Yield 73% as a solid. $^1$H NMR (300 MHz/CDCl$_3$) δ 2.43 (3H, s), 7.05 (1H, d, J=2.6 Hz), 7.09-7.11 (1H, m), 7.21 (1H, d, J=2.6 Hz), 7.36 (1H, brs), 7.49-7.66 (4H, m), 7.96 (1H, s), 8.10 (1H, d, J=8.2 Hz), 8.80 (1H, brs). MS (M+H) 511. mp 187° C.

Example 51

3-Chloro-4-(quinolin-3-yloxy)nitrobenzene (51). To a solution of 3-hydroxyquinoline (1.00 g) and 3-chloro-4-fluoronitrobenzene (1.21 g) in acetone (20 mL), was added K$_2$CO$_3$ (2.86 g). The mixture was refluxed for 1 h. After cooling the reaction mixture was filtered through a short celite pad. The filtrate was concentrated to provide compound 51 (2.07 g, quant.) as a brown oil. $^1$H NMR (300 MHz/CDCl$_3$) δ 7.02 (1H, d, J=9.1 Hz), 7.61 (1H, m), 7.72-7.80 (3H, m), 8.10-8.18 (2H, m), 8.45 (1H, d, J=2.7 Hz), 8.82 (1H, d, J=2.8 Hz).

Example 52

3-Chloro-4-(quinolin-3-yloxy)phenylamine (52). To a solution of nitrobenzene 51 (2.07 g) and NH$_4$Cl (1.84 g) in EtOH (40 mL)—H$_2$O (10 mL), was added iron powder (1.92 g). The mixture was heated to reflux for 1 h. After cooling the reaction mixture was filtered through short celite pad. The filtrate was concentrated, diluted with sat. NaHCO$_3$ (30 mL) and extracted with AcOEt (30 mL). The combined organic layers were washed with brine (30 mL) and dried over Na$_2$SO$_4$. Concentration of the solvent afforded the aniline 52 (1.77 g, 95%) as a yellow solid. $^1$H NMR (300 MHz/CDCl$_3$) δ 3.77 (2H, brs), 6.63 (1H, dd, J=2.7 Hz, J=8.6 Hz), 6.83 (1H, d, J=2.7 Hz), 6.99 (1H, d, J=8.6 Hz), 7.24 (1H, d, J=2.8 Hz), 7.49 (1H, m), 7.56-7.64 (2H, m), 8.08 (1H, m), 8.86 (1H, J=2.8 Hz)

The structures for Examples 53-54 and 56-61 are illustrated in Table 6.

TABLE 6

| Compound | V  | W  | X      | Y  | Z  | MS (M − H) |
|----------|----|----|--------|----|----|------------|
| 53       | Cl | H  | Cl     | H  | H  | 372        |
| 54       | H  | H  | H      | H  | H  | 304        |
| 56       | H  | Cl | H      | H  | Me | 352        |
| 57       | Cl | Cl | H      | Cl | H  | 406        |
| 58       | Cl | H  | H      | H  | Me | 354 (M + H)|
| 59       | Cl | H  | Me     | H  | H  | 354 (M + H)|
| 60       | Cl | Cl | H      | H  | H  | 372        |
| 61       | Cl | H  | SO$_2$Me | H  | H  | 416        |

Example 53

Compound 53. 2-amino-6-chlorobenzothiazole (3.68 g, 20 mmol) and 1,2,3-trichloro-5-nitrobenzene (4.53 g, 20 mmol) were dissolved in anhydrous DMSO (10 mL). Solid K$_2$CO$_3$ (3.04 g, 22 mmol) was added and the reaction mixture heated to 150° C. for 4 h. Let cool, then poured into 53 mL deionized water. A fine yellow solid precipitated which was collected by filtration after attempts to dissolve the product in ethyl acetate failed. The yellow solid was suspended in 100 mL of ethyl acetate and heated to reflux. After cooling to room temperature, filtration, rinsing with ethyl acetate followed by hexanes, and drying under vacuum provided the nitro compound 53 as a yellow powder. (1.06 g) $^1$H NMR (d$_6$-DMSO) δ 8.37 (s, 2H); 7.76 (bs, 1H); 7.30 (dd, 1H); 7.23 (bs, 1H). MS (M−H) 372.

Example 54

Compound 54. To a solution of 2-chloro-4-nitro aniline (2 g) and potassium t-butoxide (12 mmol) in THF (18 mL) was added a solution of 2-chlorobenzothiazole (2.75 g) in THF (6 mL). The mixture was heated at reflux overnight then quenched into water (100 mL). The product is extracted with methylene chloride and purified by flash chromatography to afford compound 54 (300 mg) as a yellow solid. $^1$H NMR (d$_6$-acetone) δ 9.74 (br s, 1H), 9.214 (br d, 1H), 8.346 (m, 2H), 7.891 (d, J=8 Hz, 1H), 7.794 (d, J=8 Hz, 1H), 7.466 (t, J=7.2 Hz, 1H), 7.321 (t, J=7.2 Hz, 1H). MS (M−H) 304.

Example 55

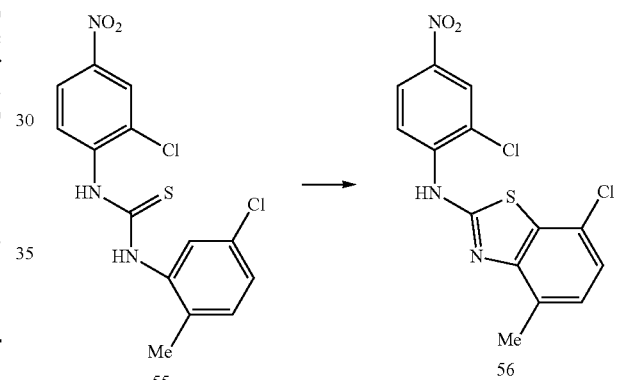

Compound 55. By the method of Abuzar et al, (Ind. J. Chem 20B, 230-233 (1981)) 2-chloro-4-nitro phenylisothiocyanate (Lancaster) (0.95 g) was coupled with 2-amino-4-chlorotoluene (0.69 g) in refluxing acetone to form the mixed thiourea 55 (1.5 g). $^1$H NMR (DMSO) δ 10.021 (s, 1H), 9.789 (s, 1H), 8.373 (m, 1H), 8.197 (m, 2H), 7.441 (d, J=1.6 Hz, 1H), 7.315 (d, J=8.4 Hz, 1H), 7.268 (dd, J=8.4, 2. Hz, 1H), 2.237 (s, 3H). MS (M+H) 356. CHN calc: 47.20% C, 3.11% H, 11.80% N. Found: 47.24% C, 3.15% N, 11.69% N.

Example 56

Compound 56. To a cool solution of thiourea 55 (0.63 g) in chloroform (6 mL) was added bromine (0.6 g) slowly. The mixture was then heated to reflux for 2 h. On cooling, the solids were collected by filtration and then triturated with acetone to afford benzothiazole 56 as its HBR salt (0.5 g). $^1$H NMR (DMSO) δ 8.989 (br d, J=8.4 Hz, 1H), 8.365 (d, J=2.4 Hz, 1H), 8.291 (dd, J=9.2, 2.8 Hz, 1H), 7.259 (m, 2H), 5.4 (br s), 2.557 (s, 3H). MS (M−H) 352. CHN calc for M+0.9HBr: 39.38% C, 2.34% H, 9.84% N; Found: 39.44% C, 2.35% H, 9.66% N.

Example 57

Compound 57. By the method of Examples 55 and 56, 2,6-dichloro-4-nitrophenylisothiocyanate was coupled with 3,5-dichloroaniline to form the corresponding mixed thiourea which was cyclized with bromine to afford benzothiazole 57 suitable for use in the next reaction. MS (M–H) 406

Example 58

By the method of Example 53, benzothiazole 58 was prepared in 78% yield as a yellow solid. MS (M+H) 354.

Example 59

By the method of Example 53, benzothiazole 59 was prepared in 30% yield as a yellow solid. MS (M+H) 354.

Example 60

Compound 60. 2,7-dichlorobenzothiazole (0.85 g, 4.2 mmol) and 2,6-dichloro-4-nitroaniline (2.1 g, 10.4 mmol) were dissolved in anhydrous DMSO (10 mL). Solid $Cs_2CO_3$ (4.1 g, 12.5 mmol) was added and the reaction mixture heated to 80° C. for 16 h. Let cool, then poured into 200 mL DI water. Excess cesium carbonate was neutralized with acetic acid. The aqueous layer was extracted 2×100 mL of ethyl acetate. The combined organic layers were washed with saturated brine, dried over $MgSO_4$, filtered, and concentrated to a yellow-brown solid. The insolubility of this compound prevented purification, so the crude material was used directly in the next reaction. $^1$H NMR (400 MHz) ($d_6$-acetone) δ 10.35 (bs, 1H); 8.36 (s, 2H); 7.37 (t, 1H); 7.30 (dd, 1H); 7.21 (dd, 1H). MS (M–H) 371.9.

Example 61

By the method of Examples 55 and 56, 2,6-dichloro-4-nitrophenylisothiocyanate (GB1131780 (1966)) was coupled with methyl-(4-aminophenyl)-sulfone to form the corresponding mixed thiourea which was cyclized with bromine to afford benzothiazole 61 suitable for use in the next reaction. $^1$H NMR (DMSO) δ 8.44 (s, 2H), 8.28 (br s, 2H), 7.82 (br d, 1H), 7.41 (br d, 1H), 3.19 (s, 3H). MS (M–H) 416.

Examples 62-69

Reduction of the nitro derivatives of Table 6 by Method A described in Examples 16-23 gave the corresponding anilines illustrated in Table 7.

TABLE 7

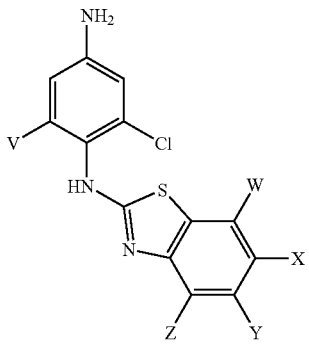

| Compound | V | X | X | Y | Z | MS (M + H) |
|---|---|---|---|---|---|---|
| 62 | Cl | H | Cl | H | H | 344 |
| 63 | H | H | H | H | H | 276 |
| 64 | H | Cl | H | H | Me | 324 |
| 65 | Cl | Cl | H | Cl | H | 378 |
| 66 | Cl | H | H | H | Me | 324 |

TABLE 7-continued

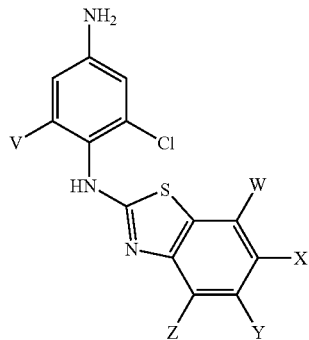

| Compound | V | X | X | Y | Z | MS (M + H) |
|---|---|---|---|---|---|---|
| 67 | Cl | H | Me | H | H | 324 |
| 68 | Cl | Cl | H | H | H | 344 |
| 69 | Cl | H | $SO_2Me$ | H | H | 388 |

Example 62

$^1$H NMR ($d_6$-acetone) δ 8.78 (s, 1H); 7.29 (d, 1H); 7.41 (d, 1H); 7.27 (d, 1H); 6.86 (s, 2H); 5.42 (s. 1H). MS (M+H) 344.

Example 65

$^1$H NMR (DMSO) δ 10.09 (s, 1H), 7.48 (br s, 1H), 7.31 (d, J=1.8 Hz, 1H), 6.72 (s, 2H), 5.91 (br s, 2H). MS (M+H) 378.

Example 68

Crude 58 was reduced with $SnCl_2.2H_2O$ according to methods described herein to afford compound 68 as a greenish/gray solid after recrystallization from hot ethyl acetate/hexanes (1.14 g). $^1$H NMR ($d_6$-acetone) δ 8.87 (bs, 1H); 7.40 (dd, 1H); 7.30 (t, 1H); 7.11 (d, 1H); 6.87 (s, 2H); 5.44 (bs, 2H). MS (M+H) 344.0.

Example 69

$^1$H NMR (DMSO) δ 10.08 (s, 1H), 8.31 (s, 1H), 7.76 (d, J=8.4 Hz, 1H), 7.57 (d, J=8.4 Hz, 1H), 6.73 (s, 2H), 5.90 (s, 2H), 3.17 (s, 3H). MS (M–H) 388.

Examples 70-91

Sulfonation of the anilines of Table 7 by the method of Example 3 or one of the methods below provides the compounds illustrated in Table 8.

Method D. To a solution of aniline in methylene chloride (10 mL/g) was added sulfonyl chloride (1.1 to 1.5 equiv.) in methylene chloride. Then pyridine (2 equiv.) is added. The mixture is slowly concentrated by placing on a rotary evaporator at ambient pressure with bath temperature at 40 to 60° C. After 2 to 18 h, the mixture is concentrated under vacuum and redissolved in methylene chloride. Flash chromatography with 0-20% ethyl acetate in methylene chloride provides the desired product which can often be triturated with ether or hexane to provide solid product.

Method E. A solution of aniline (0.5 mmol) in acetone (3 mL) was treated with aryl sulfonyl chloride (1 equiv.), 2,6-lutidine (1 equiv.) and catalytic DMAP overnight at ambient temperature. The reaction was diluted with methylene chloride, washed with 1 N HCl and then brine. The organic layer was concentrated then purified by flash chromatography to yield a foam which could often be crystallized by trituration with ether/hexane.

TABLE 8

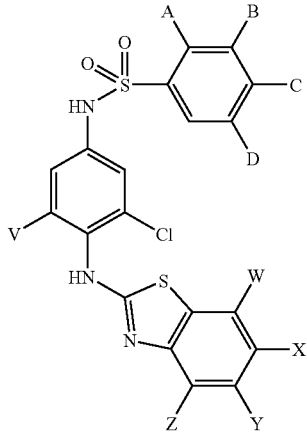

| Compound | A | B | C | D | V | W | X | Y | Z | MS (M − H) |
|---|---|---|---|---|---|---|---|---|---|---|
| 70 | Cl | H | Cl | Me | Cl | H | Cl | H | H | 564 |
| 71 | Cl | H | Cl | H | Cl | H | Cl | H | H | 550 |
| 72 | Cl | H | $CF_3$ | H | Cl | H | Cl | H | H | 584 |
| 73 | Cl | H | Cl | H | H | H | H | H | H | 482 |
| 74 | Cl | H | $CF_3$ | H | H | H | H | H | H | 516 |
| 75 | Cl | H | Cl | Me | H | H | H | H | H | 496 |
| 76 | Cl | H | Cl | H | Cl | H | Cl | H | Me | 530 |
| 77 | Cl | H | $CF_3$ | H | Cl | H | Cl | H | Me | 564 |
| 78 | Cl | H | Cl | H | Cl | Cl | H | Cl | H | 584 |
| 79 | Cl | H | $CF_3$ | H | Cl | Cl | H | Cl | H | 618 |
| 80 | Cl | H | Cl | Me | Cl | H | H | Cl | H | 598 |
| 81 | Cl | H | Cl | H | Cl | H | H | H | Me | 530 |
| 82 | Cl | H | $CF_3$ | H | Cl | H | H | H | Me | 564 |
| 83 | Cl | H | Cl | Me | H | H | H | H | Me | 544 |
| 84 | H | H | COMe | H | Cl | H | H | H | Me | — |
| 85 | Cl | H | Cl | H | Cl | H | Me | H | H | 530 |
| 86 | Cl | H | $CF_3$ | H | Cl | H | Me | H | H | 564 |
| 87 | Cl | H | Cl | Me | Cl | H | Me | H | H | 544 |
| 88 | Cl | H | Cl | H | Cl | Cl | H | H | H | 550 |
| 89 | Cl | H | $CF_3$ | H | Cl | Cl | H | H | H | 584 |
| 90 | Cl | H | Cl | H | Cl | H | $SO_2Me$ | H | H | 594 |
| 91 | Cl | H | $CF_3$ | H | Cl | H | $SO_2Me$ | H | H | 628 |

Example 70

$^1$H NMR ($d_6$-acetone) δ 9.19 (bs, 1H); 8.51 (s, 1H); 7.74 (d, 1H); 7.72 (s, 1H); 7.43 (s, 2H); 7.37 (d, 1H); 7.28 (dd, 1H); 2.46 (s, 3H). MS (M−H) 563.9

Example 71

$^1$H NMR ($d_6$-acetone) δ 9.19 (bs, 1H); 8.22 (d, 1H); 7.78 (d, 1H); 7.74 (d, 1H); 7.67 (dd, 1H); 7.43 (s, 2H); 7.37 (d, 1H); 7.28 (dd, 1H). MS (M−H) 549.8.

Example 72

$^1$H NMR ($d_6$-acetone) δ 10.05 (bs, 1H); 9.22 (bs, 1H); 8.45 (d, 1H); 8.06 (s, 1H); 7.98 (d, 1H); 7.73 (m, 1H); 7.45 (s, 2H); 7.36 (d, 1H); 7.28 (dt, 1H). MS (M−H) 583.8.

Example 73

$^1$H NMR ($d_6$-acetone) δ 9.54 (bs, 1H); 8.56 (d, 1H); 8.12 (s, 1H); 7.78 (m, 2H); 7.61 (m, 2H); 7.41 (d, 1H); 7.36 (t, 1H); 7.30 (dd, 1H); 7.20 (s, 1H). MS (M−H) 482.0

Example 74

$^1$H NMR ($d_6$-acetone) δ 9.67 (br s, 1H); 9.07 (bs, 1H); 8.59 (d, 1H); 8.34 (d, 1H); 8.04 (s, 1H); 7.91 (d, 1H); 7.77 (d, 1H); 7.61 (d, 1H); 7.42 (d, 1H); 7.36 (t, 1H); 7.32 (dd, 1H); 7.20 (t, 1H). MS (M−H) 515.9

Example 75

$^1$H NMR ($d_6$-acetone) δ 9.47 (br s, 1H); 9.06 (br s, 1H); 8.55 (br s, 1H); 8.05 (br s, 1H); 7.8-7.6 (m, 3H); 7.5-7.10 (m, 4H); 2.24 (s, 3H). MS (M+H) 497.9

Example 76

$^1$H NMR (DMSO) δ 10.96 (1H, s), 10.11 (1H, s), 8.12-8.22 (1H, broad), 8.06 (1H, d, 8.6), 7.90 (1H, d, J=2.1 Hz), 7.65 (1H, dd, J=8.6, 2.1 Hz), 7.23 (1H, d, J=3.5 Hz), 7.10-7.20 (3H, m), 2.44 (3H, s). MS (M−H) 529.8.

Example 77

$^1$H NMR DMSO) δ 11.11 (1H, s), 10.11 (1H, s), 8.27 (1H, d, J=8.0 Hz), 8.16 (2H, s), 7.94 (1H, d, J=8.6 Hz), 7.10-7.26 (4H, m), 2.43 (3H, s). MS (M−H) 563.9. mp 192.6° C.

Example 78

$^1$H NMR (DMSO) δ 11.49 (s, 1H), 10.44 (s, 1H), 8.164 (d, J=8.4 Hz, 1H) 7.95 (d, J=2 Hz, 1H), 7.71 (dd, J=8.4, 2 Hz, 1H), 7.50 (br s, 1H), 7.35 (d, J=1.6 Hz, 1H), 7.25 (s, 2H). MS (M−H) 584.

Example 79

$^1$H NMR (DMSO) δ 11.59 (s, 1H), 10.40 (s, 1H), 8.368 (d, J=8.4 Hz, 1H), 8.20 (br s, 1H), 8.00 (br d, J=8.4 Hz, 1H), 7.48 (br s, 1H), 7.344 (t, J=1.6 Hz, 1H), 7.274 (d, J=1.6 Hz, 2H). MS (M−H) 618.

Example 80

$^1$H NMR (DMSO) δ 11.37 (s, 1H), 10.40 (s, 1H), 8.19 (br s, 1H), 7.90 (m, 1H), 7.53 (br s, 1H), 7.35 (br s, 1H), 7.25 (br s, 2H), 2.415 (s, 3H). MS (M−H) 598.

Example 81

$^1$H NMR ($d_6$-DMSO) δ 11.44 (1H, broad s); 9.96 (1H, broad s); 8.33 (1H, d); 8.19 (1H, s); 7.99 (1H, dd); 7.43 (1H, broad s); 7.26 (2H, s); 7.07 (1H, d); 6.97 (1H, t); 2.35 (3H, s). MS (M−H). 529.9

Example 82

$^1$H NMR ($d_6$-DMSO) δ 11.26 (1H, broad s); 9.96 (1H, broad s); 8.12 (1H, d); 7.93 (1H, d); 7.69 (1H, dd); 7.43 (1H, broad s); 7.23 (2H, s); 7.08 (1H, d); 6.97 (1H, t); 2.36 (3H, s). MS (M−H) 564.

Example 83

$^1$H NMR ($d_6$-DMSO) δ 11.23 (1H, broad s); 9.96 (1H, broad s); 8.14 (1H, s); 7.88 (1H, s); 7.43 (1H, broad s); 7.24 (2H, s); 7.08 (1H, d); 6.97 (1H, t); 2.40 (3H, s); 2.36 (3H, s). MS (M−H) 543.9.

Example 84

$^1$H NMR (d$_6$-DMSO) δ 11.02 (1H, broad s); 9.96 (1H, broad s); 8.16 (2H, d); 7.97 (2H, d); 7.43 (1H, broad s); 7.26 (1H, s); 7.07 (1H, d); 6.97 (1H, t); 2.62 (3H, s); 2.36 (3H, s).

Example 85

$^1$H NMR (d$_6$-DMSO) δ 11.28 (1H, broad s); 9.79 (1H, broad s); 8.13 (1H, d); 7.93 (2H, d); 7.70 (1H, dd); 7.44 (1H, broad s); 7.21 (3H, s); 7.05 (1H, d); 2.30 (3H, s). MS (M−H) 529.9.

Example 86

$^1$H NMR (d$_6$-DMSO) δ 11.43 (1H, broad s); 9.79 (1H, broad s); 8.34 (1H, d); 8.19 (1H, s); 7.99 (1H, d); 7.44 (1H, broad s); 7.24 (3H, s); 7.04 (1H, d); 2.30 (3H, s). MS (M−H) 564.

Example 87

$^1$H NMR (d$_6$-DMSO) δ 11.22 (1H, broad s); 9.79 (1H, broad s); 8.15 (1H, s); 7.89 (1H, s); 7.44 (1H, broad s); 7.23 (3H, s); 7.04 (1H, d); 2.41 (3H, s); 2.31 (3H, s). MS (M−H) 543.9.

Example 88

$^1$H NMR (d$_6$-acetone) δ 9.92 (s, 1H); 9.35 (bs, 1H); 8.23 (d, 1H); 7.78 (d, 1H); 7.67 (dd, 1H); 7.45 (s, 2H); 7.36-7.29 (m, 2H); 7.16 (dd, 1H). MS (M−H) 549.8.

Example 89

$^1$H NMR (d$_6$-acetone) δ 8.45 (d, 1H); 8.06 (s, 1H); 7.97 (d, 1H); 7.46 (s, 2H); 7.33-7.29 (m, 2H); 7.16 (dd, 1H). MS (M−H) 583.8.

Example 90

$^1$H NMR (DMSO) δ 11.43 (br s, 1H), 10.40 (br s, 1H), 8.33 (br s, 1H), 8.16 (d, J=8 Hz, 1H); 7.94 (d, J=2 Hz, 1H), 7.753 (dd, J=8.2, 2 Hz, 1H), 7.71 (dd, J=8.4, 2 Hz, 1H), 7.55 (br s, 1H), 7.265 (s, 2H), 3.22 (s, 3H). MS (M−H) 594.

Example 91

$^1$H NMR (DMSO) δ 11.55 (br s, 1H), 10.40 (br s, 1H), 8.38 (m, 2H), 8.22 (br s, 1H), 8.02 (br d, 1H), 7.77 (dd, J=8.4, 2 Hz, 1H), 7.55 (br s, 1H), 7.295 (s, 2H), 3.19 (s, 3H). MS (M−H) 628.

Example 92

3-Hydroxy-6-methylquinoline (92). A solution of 3-Amino-6-methylquinoline [(1.21 g, 7.65 mmol), prepared according to *J. Chem. Soc.* 2024-2027 (1948) Morley et al.] in 6N H$_2$SO$_4$ (25 mL) was cooled in an ice bath. To the solution NaNO$_2$ (560 mg, 8.10 mmol) in water (2 mL) was added and stirred for 30 min at 0° C. Separately 5% H$_2$SO$_4$ was refluxed and above Diazo reaction mixture was added to this refluxing solution. After 30 min the reaction mixture was cooled to room temperature, and was neutralized by 6N NaOH. The resulting insoluble material was collected by filtration. This solid was recrystallized by CHCl$_3$/AcOEt to afford compound (92) (348 mg, 29%). $^1$H NMR (300 MHz, DMSO-d$_6$) δ 7.34 (1H, dd, J=1.9, 8.6 Hz), 7.42 (1H, d, J=2.8 Hz), 7.55 (1H, s), 7.79 (1H, d, J=8.6 Hz), 8.50 (1H, d, J=2.8 Hz).

Example 93

3-(2,6-Dichloro-4-nitro-phenoxy)-6-methyl-quinoline (93). To a solution of 3-Hydroxy-6-methylquinoline (92) (348 mg, 2.19 mmol) in DMF (3.5 mL), was added NaH (60% oil suspension, 90 mg, 2.25 mmol) in one portion at room temperature. After 5 min 3,4,5-trichloronitrobenzene (509 mg, 2.25 mmol) in DMF (2 mL) was added and the reaction mixture was heated at 50° C. with stirring for 2 h. After cooling to room temperature. Ice/water was added to the reaction mixture, which was then acidified with 2N HCl and extracted twice with AcOEt. Organic layer was washed with brine, dried over anhydrous MgSO$_4$, and concentrated. Crude residue was purified by column chromatography (hexane/AcOEt=4/1, 80 g of silica gel) to afford compound 93 (510 mg, 67%). $^1$H NMR (300 MHz, DMSO-d$_6$) δ 7.52-7.57 (2H, m), 7.61 (1H, s), 7.94 (1H, d, J=8.6 Hz), 8.63 (2H, s), 8.86 (1H, d, J=2.9 Hz).

Example 94

3-(2,6-Dichloro-4-nitro-phenoxy)-quinoline-carboxylic acid (94). A solution of 3-(2,6-dichloro-4-nitro-phenoxy)-6-methyl-quinoline (93) (510 mg, 1.46 mmol) and chromium (VI) oxide (292 mg, 2.92 mmol) in CH$_2$SO$_4$/H$_2$O=2.4 mL/4.7 mL was heated at 100° C. while three 292 mg portions of chromic anhydride were added eight hour intervals. After 32 h heating was stopped and allowed to stand overnight. Insoluble material was collected by filtration, and this solid was washed with water twice to afford compound (94) (443 mg, 80%). $^1$H NMR (300 MHz, DMSO-d$_6$) δ 7.94 (1H, d, J=3.0 Hz), 8.14 (2H, s), 8.56 (1H, s), 8.65 (2H, s), 9.09 (1H, d, J=3.0 Hz).

Example 95

3-(2,6-Dichloro-4-nitro-phenoxy)-quinoline-6-carboxylic acid methyl ester (95). To a solution of 3-(2,6-Dichloro-4-nitro-phenoxy)-quinoline-6 carboxylic acid (94) (443 mg, 0.93 mmol) in dry THF (20 mL) was added CH$_2$N$_2$ in Et$_2$O solution [Prepared from nitrosomethylurea (1.65 g) and 50% KOH (5 mL)]. This mixture was stirred at room temperature for 1 h. AcOH (1 mL) was added to the reaction mixture, which was then concentrated. Sat NaHCO$_3$ was added to the residue, which was extracted twice with AcOEt. Organic layer was washed by brine, dried over anhydrous MgSO$_4$, and concentrated to afford compound 95 (415 mg). $^1$H NMR (300 MHz, DMSO-d$_6$) δ 3.89 (3H, s), 5.75 (2H, br s), 6.76 (2H, s), 7.73 (1H, d, J=2.9 Hz), 8.09 (2H, s), 8.67 (1H, s), 8.94 (1H, d, J=2.9 Hz).

Example 96

3-(4-Amino-2,6-dichloro-phenoxy)-quinoline-6-carboxylic acid methyl ester (96). To a solution of 3-(2,6-dichloro-4-nitro-phenoxy)-quinoline-6-carboxylic acid methyl ester (95) (0.93 mmol) and NH$_4$Cl (283 mg, 5.3 mmol) in EtOH/THF/water (8 mL/16 mL/1 mL) was added iron powder (296 mg, 5.3 mmol). The reaction mixture was refluxed for 4 h. Insoluble materials were removed by Celite pad, which was washed by THF, acetone and then EtOH. The filtrate was concentrated, and sat NaHCO$_3$ was added and extracted twice with AcOEt. Organic layer was washed by brine, dried over anhydrous MgSO$_4$, and concentrated to afford compound 96

(372 mg, over weight). $^1$H NMR (300 MHz, DMSO-$d_6$) δ 3.89 (3H, s), 5.75 (2H, s), 6.76 (2H, s), 7.73 (1H, d, J=2.9 Hz), 8.09 (2H, s), 8.67 (1H, s), 8.94 (1H, d, J=2.9 Hz).

Example 97

3-Hydroxy-8-quinolinecarboxylic acid methyl ester (97). To the mixture of 8-quinoline carboxylic acid (500 mg, 2.89 mmol) in THF (80 mL) was added CH$_2$N$_2$ in Et$_2$O sol. [Prepared from nitrosomethylurea (1.65 g) and 50% KOH (5 mL)] at room temperature. The reaction mixture was stirred for 12 h and then concentrated to give the intermediate ester. $^1$H NMR (300 MHz, DMSO-$d_6$) δ 3.92 (3H, s), 7.60-7.70 (2H, m), 7.93-7.96 (1H, m), 8.14-8.17 (1H, m), 8.44-8.48 (1H, m), 8.97-8.99 (1H, m). To a solution of the intermediate 8-Quinolinecarboxylic acid methyl ester (2.89 mmol) in AcOH (4 mL) was added 30% H$_2$O$_2$ (0.6 mL). The reaction mixture was heated at 85° C. for 7.5 h. The reaction mixture was treated with sat NaHCO$_3$, and extracted six times with CHCl$_3$. Organic layer was dried over anhydrous MgSO$_4$, and concentrated. Crude residue was triturated with CHCl$_3$/toluene to provide compound 97 (256 mg, 44%, in 2 steps). $^1$H NMR (300 MHz, DMSO-$d_6$) δ 3.89 (3H, s), 7.52 (1H, d, J=6.9 Hz), 7.57 (1H, d, J=1.5 Hz), 7.66 (1H, dd, J=1.5, 6.9 Hz), 7.95 (1H, dd, J=1.5, 8.1 Hz), 8.63 (1H, d, J=2.7 Hz), 10.5 (1H, br s).

Example 98

3-(2,6-Dichloro-4-nitro-phenoxy)-quinoline-8-carboxylic acid methyl ester (98). To a solution of 3-Hydroxy-8-quinolinecarboxylic acid methyl ester (97) (256 mg, 1.26 mmol) and 3,4,5-trichloronitrobenzene (294 mg, 1.30 mmol) in acetone (40 mL) was added K$_2$CO$_3$ (870 mg, 6.30 mmol). This mixture was refluxed for 3.5 h. The reaction mixture was cooled to room temperature and insoluble materials were removed by Celite filtration. The filtrate was concentrated and the residue was purified by column chromatography. (hexane/AcOEt=4/1, 80 g of silica gel) to afford compound 98. $^1$H NMR (300 MHz, DMSO-$d_6$) δ 3.92 (3H, s), 7.67 (1H, dd, J=7.3 Hz), 7.79 (1H, d, J=2.9 Hz), 7.88 (1H, dd, J=1.5, 7.3 Hz), 9.05 (1H, d, J=2.9 Hz).

Example 99

3-(4-Amino-2,6-dichloro-phenoxy)-quinoline-8-carboxylic acid methyl ester (99). To a solution of 3-(2,6-Dichloro-4-nitro-phenoxy)-quinoline-8-carboxylic acid methyl ester (98) (1.26 mmol) and NH4Cl (370 mg, 6.91 mmol) in EtOH/THF/H$_2$O=8 mL/4 mL/2 mL was added iron powder (386 mg, 6.91 mmol). The reaction mixture was refluxed for 3.5 h. After cooling to room temperature and insoluble materials were filtered by Celite filtration. The filtrate was concentrated and sat NaHCO$_3$ was added to the residue, which was extracted twice with AcOEt. Organic layer was washed by brine, dried over MgSO$_4$, and concentrated. Crude residue was purified by column chromatography (hexane/AcOEt=2/1, 80 g of silica gel) to afford compound 99 (543 mg). $^1$H NMR (300 MHz, DMSO-$d_6$) δ 3.91 (3H, s), 5.77 (2H, br s), 6.78 (2H, s), 7.50 (1H, d, J=3.0 Hz), 7.61 (1H, dd, J=8.1 Hz), 7.81 (1H, dd, J=1.4, 6.4 Hz), 8.08 (1H, dd, J=1.4 Hz, 6.4 Hz), 8.93 (1H, d, J=3.0 Hz).

Example 100

3,5-Dichloro-4-(6-methyl-quinolin-3-yloxy)-phenylamine (100). To a solution of 3-(2,6-Dichloro-4-nitro-phenoxy)-6-methyl-quinoline (93) (1.30 g, 3.71 mmol) and NH4Cl (992 mg, 18.55 mmol) in EtOH/THF/H$_2$O=12 mL/12 mL/3 mL, was added iron powder (1.04 g, 18.55 mmol). The mixture was refluxed for 4 h. Insoluble materials were removed by Celite filtration. The filtrate was concentrated and sat NaHCO$_3$ was added to the residue, which was then extracted twice with AcOEt. Organic layer was washed with brine, dried over anhydrous MgSO$_4$, and concentrated to afford compound 100 (1.18 g, 98%). $^1$H NMR (300 MHz, DMSO-$d_6$) δ 2.44 (3H, s), 5.75 (2H, br s), 6.77 (2H, s), 7.27 (1H, d, J=2.8 Hz), 7.48 (1H, d, J=8.6 Hz), 7.67 (1H, s), 7.89 (1H, d, J=8.6 Hz), 8.74 (1H, d, J=2.8 Hz).

Example 101

2,6-Dichloro-benzothiazole (101). 2-Amino-6-chlorobenzothiazole (15.7 g, 85 mmol) in H$_3$PO$_4$ (85%) (470 mL) was heated to 100° C. and dissolved. Then clear solution was cooled and vigorously stirred by mechanical stirrer. NaNO$_2$ (17.6 g, 255 mmol) in water (30 mL) was added slowly keeps the temperature below 0° C. Separately a solution of CuSO$_4$/5H$_2$O (85 g), NaCl (107 g) in water (350 mL) was cooled to −5° C. and stirred by mechanical stirrer. After potassium iodide starch paper's color was disappeared diazonium solution was keeping cold and added slowly to the copper chloride solution with vigorous stirring. The reaction mixture was allowed to warm to room temperature. After 1 h water (1 L) and ether (1 L) were added to the reaction mixture and extracted twice. Organic layer was washed by water and dried over anhydrous MgSO$_4$ and concentrated. Crude residue was purified by silica gel chromatography (H/A=4/1, 180 g of silica gel) to provide title compound 101 (7.46 g, 48%).

Example 102

3,5-dichloro-4-(6-chloro-benzothiazol-2-yloxy)-phenylamine (102). To the solution of 4-amino-2,6-dichloro phenol (6 g, 26.5 mmol) and 2,6-dichlorobenzothiazole (101) (6 g, 29.4 mmol, 1.1 equiv.) in DMSO (25 mL), was added K$_2$CO$_3$ (11 g, 80 mmol, 3.0 equiv.). The mixture was stirred and heated to 160° C. After 5.5 h water (20 mL) was added to the reaction mixture, which was neutralized with 2N HCl, and was extracted with AcOEt three times. And the organic layer was washed with brine and was dried over anhydrous MgSO$_4$, and then concentrated. Crude residue was purified by column chromatography (CHCl$_3$/acetone=9/1, 180 g of silica gel) to afford 3,5-dichloro-4-(6-chloro-benzothiazol-2-yloxy)-phenylamine (102) as a black solid (4.52 g, 49%). $^1$H NMR (300 MHz, DMSO-$d_6$) δ 5.86 (2H, br s), 6.74 (2H, s), 7.48 (1H, dd, J=2.1, 5.7 Hz), 7.70 (1H, d, 8.7 Hz), 8.10 (1H, d, 2.1 Hz).

Example 103

2-Chloro-N-[3,5-dichloro-4-(6-chloro-benzothiazol-2-yloxy)-phenyl]-4-trifluoromethyl-benzenesulfonamide (103). A solution of 3,5-dichloro-4-(6-chloro-benzothiazol-2-yloxy)-phenylamine (102) (2.0 g, 5.79 mmol) and 3-chloro-4-trifluoromethylbenzenesulfonylchloride (1.7 g, 6.08 mmol) in pyridine (10 mL) was stirred at room temperature. After 3 h water was added to the reaction mixture, which was then acidify by 2N HCl. Reaction mixture was extracted twice with AcOEt. Organic layer was washed by brine, dried over MgSO$_4$ and concentrated. Crude residue was purified by column chromatography (H/A=4/1, 80 g of silica gel) to afford title compound 103 (2.11 g, 65%) as a white solid. mp 82-84°. $^1$H NMR (400 MHz, DMSO-$d_6$) δ 7.32 (2H, s), 7.46 (1H, dd, J=2.2, 8.7 Hz), 7.67 (1H, d, J=8.7 Hz), 8.00 (1H, d, 8.0 Hz), 8.14 (1H, d, J=2.2 Hz), 8.20 (1H, s), 8.38 (1H, d, J=8.3 Hz), 11.6 (1H, br s). MS (M+H) 586

Example 104

2,4-Dichloro-N-[3,5-dichloro-4-(6-chloro-benzothiazol-2-yloxy)-phenyl]benzenesulfonamide (104). A solution of 3,5-dichloro-4-(6-chloro-benzothiazol-2-yloxy)-phenylamine (102) (2.0 g, 5.79 mmol) and 2,4-dichloro benzenesulfonylchloride (1.5 g, 6.08 mmol) in pyridine (10 mL) was stirred at room temperature for 12 h. Water was added to the reaction mixture, which was then acidified by 2N HCl. Reaction mixture was extracted twice with AcOEt. Organic layer was washed by brine, dried over $MgSO_4$ and concentrated. Crude residue was purified by column chromatography (H/A=4/1, 80 g of silica gel) to afford title compound (104) (1.49 g, 46%) as a white solid. Mp 73-75° C. $^1$H NMR (300 MHz, DMSO-$d_6$) δ 7.29 (2H, s), 7.46 (1H, dd, J=2.2, 8.8 Hz), 7.69 (1H, d, J=8.8 Hz), 7.71 (1H, dd, J=2.2, 8.4 Hz), 7.95 (1H, d, J=2.2 Hz), 8.14 (1H, d, J=2.2 Hz), 8.18 (1H, d, J=8.4 Hz), 11.5 (1H, br s). MS (M+H) 553.

Example 105

3,5-Dichloro-4-(6-methoxybenzothiazol-2-yloxy)phenylamine (105). To a solution of 2-chloro-6-methoxybenzothiazole (prepared as described by Weinstock et. al., J. Med. Chem. 30: p. 1166 (1987)) and 4-Amino-2,6-dichlorophenol 1.3 g (available from Tokyo Chemical Industry Co., Ltd.) in DMSO (9 mL), was added $K_2CO_3$ 3.12 g. The mixture was heated at 150° C. for 3 h. The reaction mixture was purified by column chromatography (silica gel, AcOEt:hexane=1:2) to provide the aniline 105 (1.43 g, 56%). mp 158-160° C. $^1$H NMR (300 MHz/CDCl$_3$) δ 3.84 (3H, s), 3.85 (2H, brs), 6.69 (2H, s) 6.97 (1H, dd, J=2.6 Hz, J=8.9 Hz), 7.18 (1H, d, J=2.6 Hz), 7.61 (1H, d, J=8.9 Hz).

Example 106

2-Chloro-N-[3,5-dichloro-4-(6-methoxybenzothiazol-2-yloxy)-phenyl]-4-trifluoromethyl-benzenesulfonamide (106).

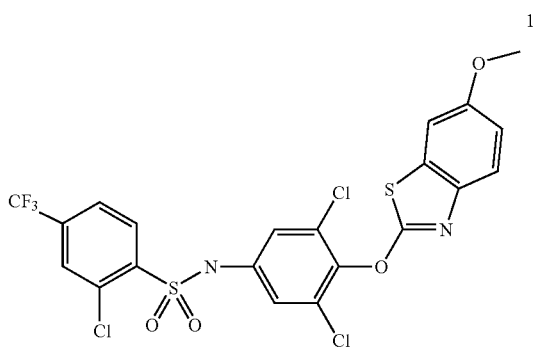

To a solution of 3,5-dichloro-4-(6-methoxybenzothiazol-2-yloxy)phenylamine (105) (1.40 g) in pyridine (5 mL), was added 2-chloro-4-trifluorobenzenesulfonamide 1.15 g. The mixture was stirred at room temperature for 2 h. The reaction mixture was purified directly by column chromatography (silica gel, AcOEt:hexane=1:3). The product was triturated by hexane to give the title compound 106 (1.97 g, 82%) as a colorless powder. mp 164-165° C. NMR (300 MHz/DMSO-d6) δ 3.79 (3H, s), 7.00 (1H, dd, J=2.9 Hz, J=8.8 Hz), 7.31 (2H, s), 7.55 (1H, d, J=8.8 Hz), 7.58 (1H, d, J=2.9 Hz), 8.00 (1H, dd, J=1.5 Hz, J=8.1 Hz), 8.20 (1H, d, J=1.5 Hz), 8.37 (1H, d, J=8.1 Hz), 11.59 (1H, brs). MS (M+H) 583.

Example 200

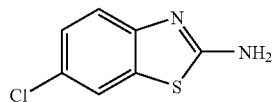

6-Chloro-benzothiazol-2-ylamine (200). Concentrated sulfuric acid (VWR, 5.4 mL, 100 mmol) was added over a 10-min period to a stirred solution of 4-chloroaniline (Aldrich, 25.52 g, 200 mmol) in 130 mL of chlorobenzene. A thick suspension was formed. To the above suspension was added KSCN (Aldrich, 25.3 g, 260 mmol) and the mixture was then heated to 110° C. for 6 h. The mixture was cooled to room temperature, diluted with 300 mL of hexanes and filtered. The precipitate was taken up in 500 mL of water, heated to 80° C. for 30 min. Filtration gave 32.0 g product.

To a stirred solution of the above product in 120 mL of CHCl$_3$ at 10° C. was added bromine (Aldrich, 68.8 g, 430 mmol) over a 20 min period. The mixture was stirred at ambient temperature for 30 min and was then refluxed for 30 min. Filtration followed by washing the solid with CHCl$_3$ and ether gave a yellow solid, which was suspended in acetone. This discharged the yellow color, and filtration followed by washing with acetone and with ether gave a white solid. The solid was dissolved in 800 mL of hot water and the cooled solution was brought to pH 9 with concentrated NH$_4$OH. Filtration followed by washing with water gave 17.8 g product. $^1$H NMR (400 MHz, DMSO-d$_6$) δ 7.76 (d, J=2.0 Hz, 1H), 7.59 (s, 2H), 7.29 (d, J=8.5 Hz, 1H), 7.21 (dd, J=8.5, 2.2 Hz, 1H). MS (EI): m/z 185 (M+H).

Example 201

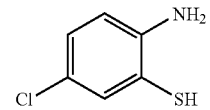

2-Amino-5-chloro-benzenethiol (201). A solution of 6-chloro-benzothiazol-2-ylamine (Example 200, 17.8 g, 96.7 mmol) and KOH (EM, 87 g, 1.55 mol) in 150 mL of water was refluxed for 2 d. The mixture was cooled to room temperature and was diluted with ice. The solution was brought to pH 5 with concentrated HCl. The mixture was extracted 3× with EtOAc (300 mL). The organic layers were combined and washed twice with a brine solution (300 mL), dried over Na$_2$SO$_4$. Removal of the solvent under reduced pressure gave 10.5 g product. $^1$H NMR (400 MHz, DMSO) δ 7.20 (d, J=2.5 Hz, 1H), 6.93 (dd, J=8.6, 2.5 Hz, 1H), 6.69 (d, J=8.6 Hz, 1H) 5.30 (s, 3H). MS (EI): m/z 160 (M+H).

Example 202

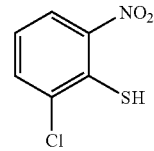

2-Chloro-6-nitro-benzenethiol (202). To a solution of 2,3-dichloronitrobenzene (Aldrich, 19.2 g, 100 mmol) in 300 mL of DMSO was added powdered Na$_2$S 9H$_2$O (Aldrich, 24.0 g, 100 mmol). The mixture was stirred at ambient temperature for 24 h, then was diluted with 2 L of water. The mixture was clarified by filtration and the filtrate was acidified to pH 4 with con. HCl. The mixture was extracted 3× with Et$_2$O (400 mL). The organic layers were combined and washed twice with a brine solution (400 mL), dried over Na$_2$SO$_4$. Removal of the solvent under reduced pressure gave 18.4 g product. $^1$H NMR (400 MHz, DMSO) δ 8.11 (dd, J=8.3, 1.3 Hz, 1H), 7.93 (dd, J=8.0, 1.3 Hz, 1H), 7.40 (td, J=8.2, 1.3 Hz, 1H) 5.06 (s, 1H). MS (EI): m/z 188 (M−H).

Example 203

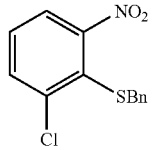

203

Benzyl 2-chloro-6-nitrobenzenethiol ether (203). To a solution of 2-chloro-6-nitro-benzenethiol (Example 202, 9.5 g, 50 mmol) in 200 mL of DMF was added NaH (Aldrich, 2.60 g, 60%, 65 mmol). The mixture was stirred for 20 min, then was added benzyl bromide (Aldrich, 6.2 mL, 52 mmol). After stirred for 3 h, the mixture was diluted with 2N HCl, extracted 3× with EtOAc (200 mL). The organic layers were combined and washed twice with a brine solution (200 mL), dried over Na$_2$SO$_4$, and concentrated under vacuum. The residue was chromatographed (40%-60% CH$_2$Cl$_2$/hexanes) to yield 12.82 g (92%) of product. $^1$H NMR (400 MHz, DMSO) δ 7.87 (dd, J=8.1, 1.3 Hz, 1H), 7.76 (dd, J=8.0, 1.3 Hz, 1H), 7.59 (t, J=8.1 Hz, 1H) 7.24-7.18 (m, 3H), 7.10-7.06 (m, 2H), 4.15 (s, 2H).

Example 204

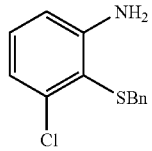

204

2-Benzylsulfanyl-3-chloro-phenylamine (204). 2-Benzylsulfanyl-3-chloro-phenylamine (204) was synthesized from benzyl 2-chloro-6-nitrobenzenethiol ether (203, 20.0 g, 71.6 mmol) in a similar manner as described in Examples 16-23 (Method A). $^1$H NMR (400 MHz, DMSO) δ 7.27-7.18 (m, 5H), 7.00 (t, J=8.0 Hz, 1H), 6.65 (dd, J=8.0, 1.1 Hz, 1H), 6.63 (dd, J=8.0, 1.1 Hz, 1H), 3.91 (s, 2H). The product was used directly for the next reaction as in Example 205.

Example 205

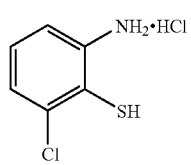

205

2-Amino-6-chlorobenzenethiol hydrochloride (205). To a solution of 2-benzylsulfanyl-3-chloro-phenylamine (204) in 140 mL of benzene at 0° C. was added AlCl$_3$ (Aldrich, 23.8 g, 179 mmol) in portion. The mixture turned to purple. After stirred at ambient temperature overnight, the mixture was poured to ice and EtOAc and stirred for 20 min. The mixture was extracted 3× with EtOAc (500 mL). The organic layers were washed twice with a brine solution (400 mL), dried over Na$_2$SO$_4$, and concentrated under vacuum. The crude product was treated with 145 mL of 1N HCl in ether. The product (13.6 g) was collected by filtration and washed with hexanes. $^1$H NMR (400 MHz, DMSO) δ 7.05 (t, J=8.2 Hz, 1H), 6.70 (d, J=8.2 Hz, 1H), 6.61 (d, J=7.8 Hz, 1H).

Example 206

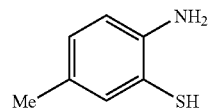

206

2-Amino-5-methyl-benzenethiol (206). 6-methyl-2-aminobenzothiazole (5 g) was suspended in a solution of KOH (25 g) in water (50 mL) and heated to reflux overnight. After cooling to ambient temperature, the solution as adjusted to pH 6 with acetic acid. The thick precipitate was collected by filtration and rinsed with water. The residue was dissolved in methylene chloride, dried over magnesium sulfate and concentrated to provide a yellow solid (4.08 g) containing the desired 2-amino-5-methyl-benzenethiol. (88% purity). 1H NMR (d6-DMSO) 6.982 (d, J=2 Hz, 1H); 6.744 (dd, J=8, 2 Hz, 1H); 6.605 (d, J=8.4 Hz, 1H); 4.885 (br s, 2H); 3.32 (s, 1H); 2.103 (s, 3H). MS (EI): m/z 138 (M−H)

TABLE 9

| Compound | X |
|---|---|
| 207 | 6-Cl |
| 208 | 7-Cl |
| 209 | 6-Me |

The compounds of Table 9 were prepared using the method of Example 8.

Example 207

6-Chloro-2-(2,6-dichloro-4-nitro-benzyl)-benzothiazole (207). $^1$H NMR (400 MHz, DMSO-d$_6$) δ 8.41 (s, 2H), 8.23 (d, J=2.1 Hz, 1H), 7.90 (d, J=8.7 Hz, 1H), 7.50 (dd, J=8.7, 2.1 Hz, 1H), 4.87 (s, 2H). MS (EI): m/z 373 (M+H).

Example 208

7-Chloro-2-(2,6-dichloro-4-nitro-benzyl)-benzothiazole (208). $^1$H NMR (400 MHz, DMSO-$d_6$) δ 8.41 (s, 2H), 7.91 (dd, J=7.8, 1.0 Hz, 1H), 7.56 (t, J=7.7 Hz, 1H), 7.53 (d, J=7.8 Hz, 1H), 4.92 (s, 2H). MS (EI): m/z 373 (M+H).

Example 209

2-(2,6-Dichloro-4-nitro-benzyl)-6-methyl-benzothiazole (209). 1H NMR (400 MHz, DMSO-$d_6$) δ 8.40 (s, 2H), 7.84 (br s, 1H), 7.76 (d, J=8.3 Hz, 1H), 7.28 (d, J=8.3 Hz, 1H), 4.84 (s, 2H). MS (EI): m/z 353 (M+H).

TABLE 10

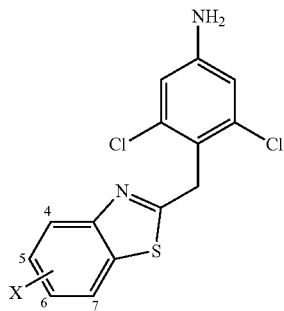

| Compound | X |
|---|---|
| 210 | 6-Cl |
| 211 | 7-Cl |
| 212 | 6-Me |

The compounds of Table 10 were prepared using Method A described in Examples 16-23.

Example 210

3,5-Dichloro-4-(6-chloro-benzothiazol-2-ylmethyl)-phenylamine (210). $^1$H NMR (400 MHz, DMSO-$d_6$) δ 8.16 (t, J=1.8 Hz, 1H), 7.92 (dd, J=8.7, 1.4 Hz, 1H), 7.50 (dt, J=8.7, 2.0 Hz, 1H), 6.69 (s, 2H), 5.79 (s, 2H), 4.50 (s, 2H). MS (EI): m/z 343 (M+H).

Example 211

3,5-Dichloro-4-(7-chloro-benzothiazol-2-ylmethyl)-phenylamine (211). $^1$H NMR (400 MHz, DMSO-$d_6$) δ 7.94 (t, J=6.8 Hz, 1H), 7.92 (m, 2H), 6.70 (s, 2H), 5.82 (s, 2H), 4.54 (s, 2H). MS (EI): m/z 343 (M+H).

Example 212

3,5-Dichloro-4-(6-methyl-benzothiazol-2-ylmethyl)-phenylamine (212). $^1$H NMR (400 MHz, DMSO-$d_6$) δ 7.82-7.75 (m, 2H), 7.28 (dd, J=8.3, 1.5 Hz, 1H), 6.68 (s, 2H), 5.76 (s, 2H), 4.48 (s, 2H), 2.40 (s, 3H). MS (EI): m/z 323 (M+H).

Examples 213-220

The compounds of Table 11 were prepared from compounds in Table 10 and the corresponding arylsulfonyl chloride using Method D described in Examples 70-91.

TABLE 11

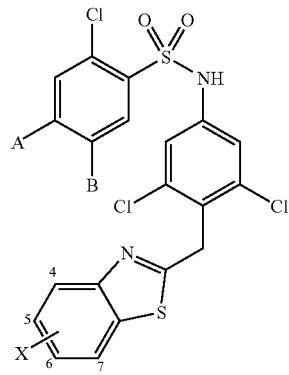

| Compound | X | A | B |
|---|---|---|---|
| 213 | 6-Cl | CF$_3$ | H |
| 214 | 6-Cl | Cl | H |
| 215 | 6-Cl | Cl | Me |
| 216 | 7-Cl | CF$_3$ | H |
| 217 | 7-Cl | Cl | H |
| 218 | 6-Me | CF$_3$ | H |
| 219 | 6-Me | Cl | H |
| 220 | 6-Me | Cl | Me |

Example 213

2-Chloro-N-[3,5-dichloro-4-(6-chloro-benzothiazol-2-ylmethyl)-phenyl]-4-trifluoromethyl-benzenesulfonamide (213). $^1$H NMR (400 MHz, DMSO-$d_6$) δ 11.55 (br s, 1H), 8.35 (d, J=8.2 Hz, 1H), 8.19 (s, 1H), 8.15 (t, J=1.9 Hz, 1H), 7.99 (d, J=8.4 Hz, 1H), 7.89 (d, J=8.7 Hz, 1H), 7.49 (dt, 8.7, 1.9 Hz, 1H), 7.23 (s, 2H), 4.60 (s, 2H). MS (EI): m/z 583 (M−H).

Example 214

2,4-Dichloro-N-[3,5-dichloro-4-(6-chloro-benzothiazol-2-ylmethyl)-phenyl]-benzenesulfonamide (214). $^1$H NMR (400 MHz, DMSO-$d_6$) δ 11.40 (br s, 1H), 8.18-8.12 (m, 2H), 7.93 (t, J=1.7 Hz, 1H), 7.90 (dd, J=8.7, 1.1 Hz, 1H), 7.69 (dt, J=8.6, 1.7 Hz, 1H), 7.49 (dt, J=8.7, 1.7 Hz, 1H), 7.20 (s, 2H), 4.60 (s, 2H). MS (EI): m/z 549 (M−H).

Example 215

2,4-Dichloro-N-[3,5-dichloro-4-(6-chloro-benzothiazol-2-ylmethyl)-phenyl]-5-methyl-benzenesulfonamide (215). $^1$H NMR (400 MHz, DMSO-$d_6$) δ 11.33 (br s, 1H), 8.18-8.15 (m, 2H), 7.90 (dd, J=8.7, 1.7 Hz, 1H), 7.87 (d, J=1.7 Hz, 1H), 7.49 (dt, J=8.7, 2.0 Hz, 1H), 7.21 (s, 2H), 4.60 (s, 2H), 2.39 (s, 3H). MS (EI): m/z 563 (M−H).

Example 216

2-Chloro-N-[3,5-dichloro-4-(7-chloro-benzothiazol-2-ylmethyl)-phenyl]-4-trifluoromethyl-benzenesulfonamide (216). $^1$H NMR (400 MHz, DMSO-$d_6$) δ 11.56 (br s, 1H), 8.35 (d, J=8.3 Hz, 1H), 8.19 (s, 1H), 7.99 (d, J=8.2 Hz, 1H), 7.90 (dd, J=7.2, 1.5 Hz, 1H), 7.58-7.50 (m, 2H), 7.23 (s, 2H), 4.64 (s, 2H). MS (EI): m/z 583 (M−H).

Example 217

2,4-Dichloro-N-[3,5-dichloro-4-(7-chloro-benzothiazol-2-ylmethyl)-phenyl]-benzenesulfonamide (217). $^1$H NMR (400 MHz, DMSO-d$_6$) δ 11.40 (br s, 1H), 8.14 (d, J=8.6 Hz, 1H), 7.95-7.90 (m, 2H), 7.69 (dd, J=8.6, 2.0 Hz, 1H), 7.58-7.48 (m, 2H), 7.20 (s, 2H), 4.64 (s, 2H). MS (EI): m/z 549 (M–H).

Example 218

2-Chloro-N-[3,5-dichloro-4-(6-methyl-benzothiazol-2-ylmethyl)-phenyl]-4-trifluoromethyl-benzenesulfonamide (218). $^1$H NMR (400 MHz, DMSO-d$_6$) δ 11.53 (br s, 1H), 8.35 (d, J=8.3 Hz, 1H), 8.18 (s, 1H), 7.99 (d, J=8.3 Hz, 1H), 7.78-7.70 (m, 2H), 7.26 (d, J=8.8.4 Hz, 1H), 7.22 (s, 2H), 4.56 (s, 2H), 2.39 (s, 3H). MS (EI): m/z 563 (M–H).

Example 219

2,4-Dichloro-N-[3,5-dichloro-4-(6-methyl-benzothiazol-2-ylmethyl)-phenyl]-benzenesulfonamide (219). $^1$H NMR (400 MHz, DMSO-d$_6$) δ 11.37 (br s, 1H), 8.14 (d, J=8.6 Hz, 1H), 7.93 (d, J=2.1 Hz, 1H), 7.79-7.74 (m, 2H), 7.69 (dd, J=8.6, 2.1 Hz, 1H), 7.32 (dd, J=8.5, 2.0 Hz, 1H), 7.20 (s, 2H), 4.56 (s, 2H), 2.40 (s, 3H). MS (EI): m/z 529 (M–H).

Example 220

2,4-Dichloro-N-[3,5-dichloro-4-(6-methyl-benzothiazol-2-ylmethyl)-phenyl]-5-methyl-benzenesulfonamide (220). $^1$H NMR (400 MHz, DMSO-d$_6$) δ 11.30 (br s, 1H), 8.16 (s, 1H), 7.87 (s, 1H), 7.80-7.74 (m, 2H), 7.26 (d, J=8.5 Hz, 1H), 7.21 (s, 2H), 4.56 (s, 2H), 2.40 (s, 3H), 2.38 (s, 3H). MS (EI): m/z 543 (M–H).

Example 221

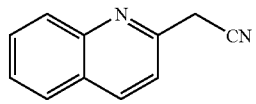

221

Quinolin-2-yl-acetonitrile (221). To a suspension of 2-Chloromethyl-quinoline hydrochloride (TCI, 4.28 g, 20 mmol) in 50 mL of EtOH was added a solution of NaHCO$_3$ (EM, 3.36 g, 40 mmol) in 30 mL of H$_2$O. The mixture was stirred for 15 min, then was added KI (Aldrich, 4.5 g, 30 mmol) and KCN (Acros, 1.95 g, 30 mmol) and the resulting mixture was refluxed for 4 h. after cooled to room temperature, EtOH was removed under reduced pressure. The residue was extracted 3× with EtOAc (200 mL). The organic layers were combined and washed twice with a brine solution (200 mL), dried over Na$_2$SO$_4$, and concentrated under vacuum. The residue was chromatographed (30% EtOAc/hexanes) to yield 2.76 g (82%) of product. $^1$H NMR (400 MHz, DMSO-d$_6$) δ 8.42 (d, J=8.4 Hz, 1H), 8.05-7.97 (m, 2H), 7.85-7.76 (m, 1H), 7.67-7.60 (m, 1H), 7.54 (d, J=8.5 Hz, 1H), 4.45 (s, 2H). MS (EI): m/z 169 (M+H).

Example 222

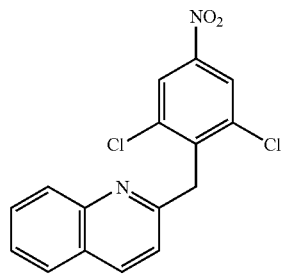

222

2-(2,6-Dichloro-4-nitro-benzyl)-quinoline (222). To a solution of quinolin-2-yl-acetonitrile (Example 221, 2.76 g, 16.4 mmol) in 30 mL of DMF, was added NaH (Aldrich, 1.44 g, 60%, 36.1 mmol) and the mixture was stirred for 15 min. To the above mixture was added 3,4,5-trichloronitrobenzene (Acros, 3.71 g, 16.4 mmol), and the resulting mixture was stirred overnight (16 h). Poured to 2N HCl, the crude product (5.50 g) was collected by filtration followed by washing with water. $^1$H NMR (400 MHz, DMSO-d$_6$) δ 10.58 (s, 1H), 7.75 (d, J=9.6 Hz, 1H), 7.60 (d, J=7.7 Hz, 1H), 7.50-7.42 (m, 1H), 7.35 (d, J=8.2 Hz, 1H), 7.22-7.14 (m, 2H).

The above crude product (3.6 g) was suspended in a mixture of 50 mL con. HCl and 20 mL of AcOH and the resulting mixture was refluxed overnight (18 h). After cooled to room temperature, the mixture was brought to pH 8 with con. NH$_4$OH, and then extracted 3× with EtOAc (200 mL). The organic layers were combined and washed twice with a brine solution (200 mL), dried over Na$_2$SO$_4$, and concentrated under vacuum. The residue was chromatographed (10%-15% EtOAc/hexanes) to yield 2.66 g of product. $^1$H NMR (400 MHz, DMSO-d$_6$) δ 8.39 (s, 2H), 8.33 (d, J=8.5 Hz, 1H), 7.95 (d, J=7.8 Hz, 1H), 7.78 (d, J=8.4 Hz, 1H), 7.69 (td, J=8.1, 1.3 Hz, 1H), 7.56 (td, J=8.0, 1.0 Hz, 1H), 7.45 (d, J=8.5 Hz, 1H), 4.74 (s, 2H). MS (EI): m/z 333 (M+H).

Example 223

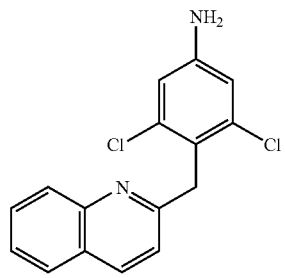

223

3,5-Dichloro-4-quinolin-2-ylmethyl-phenylamine (223). 3,5-Dichloro-4-quinolin-2-ylmethyl-phenylamine (223) was synthesized (84%) from 2-(2,6-Dichloro-4-nitro-benzyl)-quinoline (222) in a similar manner as described in Examples 16-23 (Method A). $^1$H NMR (400 MHz, DMSO-d$_6$) δ 8.24 (d, J=8.5 Hz, 1H), 7.91 (m, 2H), 7.72 (td, J=7.8, 1.4 Hz, 1H), 7.54 (td, J=7.8, 1.0 Hz, 1H), 7.13 (d, J=8.5 Hz, 1H), 6.69 (s, 2H), 5.67 (s, 2H), 4.41 (s, 2H). MS (EI): m/z 303 (M+H).

Example 224

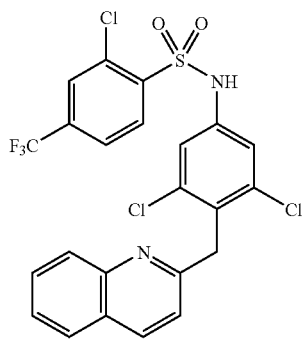

2-Chloro-N-(3,5-dichloro-4-quinolin-2-ylmethyl-phenyl)-4-trifluoromethyl-benzenesulfonamide (224). 2-Chloro-N-(3,5-dichloro-4-quinolin-2-ylmethyl-phenyl)-4-trifluoromethyl-benzenesulfonamide was synthesized (84%) from 3,5-dichloro-4-quinolin-2-ylmethyl-phenylamine (223), 2-chloro-4-trifluoromethylbenzenesulfonyl chloride (Maybridge) and pyridine (EM) in a similar manner as described in Examples 70-91. $^1$H NMR (400 MHz, DMSO-$d_6$) δ 11.45 (br s, 1H), 8.34 (d, J=8.3 Hz, 1H), 8.24 (d, J=8.5 Hz, 1H), 8.19 (s, 1H), 8.00 (d, J=8.3 Hz, 1H), 7.91 (d, J=8.0 Hz, 1H), 7.76 (d, J=8.3 Hz, 1H), 7.67 (td, J=7.8, 1.3 Hz, 1H), 7.54 (td, J=7.8, 1.0 Hz, 1H), 7.23 (d, J=8.5 Hz, 1H), 7.22 (s, 2H), 4.48 (s, 2H). MS (EI): m/z 543 (M–H).

Example 225

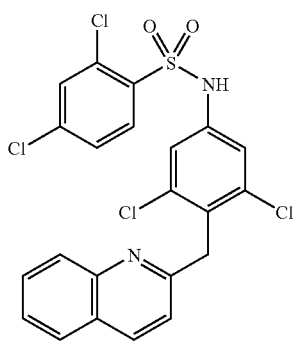

2,4-Dichloro-N-(3,5-dichloro-4-quinolin-2-ylmethyl-phenyl)-benzenesulfonamide (225). 2,4-Dichloro-N-(3,5-dichloro-4-quinolin-2-ylmethyl-phenyl)-benzenesulfonamide was synthesized (76%) from 3,5-dichloro-4-quinolin-2-ylmethyl-phenylamine (223), 2,4-dichlorobenzenesulfonyl chloride (Maybridge) and pyridine (EM) in a similar manner as described in Examples 70-91. $^1$H NMR (400 MHz, DMSO-$d_6$) δ 11.29 (br s, 1H), 8.25 (d, J=8.5 Hz, 1H), 8.13 (d, J=8.6 Hz, 1H), 7.94 (d, J=2.0 Hz, 1H), 7.91 (d, J=8.0 Hz, 1H), 7.75 (d, J=8.3 Hz, 1H), 7.70-7.65 (m, 2H), 7.54 (t, J=7.5 Hz, 1H), 7.22 (d, J=8.5 Hz, 1H), 7.20 (s, 2H), 4.48 (s, 2H). MS (EI): m/z 509 (M–H).

Example 226

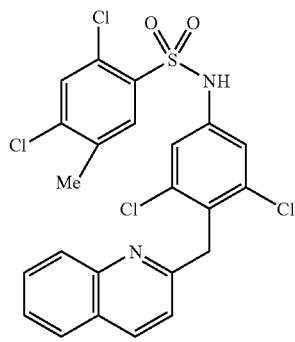

2,4-Dichloro-N-(3,5-dichloro-4-quinolin-2-ylmethyl-phenyl)-5-methyl-benzenesulfonamide (226). 2,4-Dichloro-N-(3,5-dichloro-4-quinolin-2-ylmethyl-phenyl)-5-methyl-benzenesulfonamide was synthesized (76%) from 3,5-dichloro-4-quinolin-2-ylmethyl-phenylamine (223), 2,4-dichloro-5-methylbenzenesulfonyl chloride (Maybridge) and pyridine (EM) in a similar manner as described in Examples 70-91. $^1$H NMR (400 MHz, DMSO-$d_6$) δ 11.22 (br s, 1H), 8.25 (d, J=8.5 Hz, 1H), 8.15 (s, 1H), 7.91 (d, J=8.0 Hz, 1H), 7.88 (s, 1H), 7.78 (d, J=8.3 Hz, 1H), 7.69 (t, J=7.1 Hz, 1H), 7.54 (t, J=7.5 Hz, 1H), 7.22 (d, J=8.5 Hz, 1H), 7.21 (s, 2H), 4.48 (s, 2H), 2.39 (s, 3H). MS (EI): m/z 523 (M–H).

Example 227

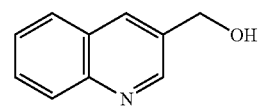

Quinolin-3-yl-methanol (227). To a suspension of quinoline-3-carboxylic acid (Aldrich, 4.85 g, 28.0 mmol) in 60 mL of 10% MeOH/THF, was added dropwise a solution of 2M (trimethylsilyl)diazomethane (Aldrich, 21 mL, 42 mmol) in hexanes. The mixture was stirred at ambient temperature for 4 h. Removal of the solvent under reduced pressure gave 5.03 g of crude product, which was used directly for the next reaction.

To a solution of the above product in 100 mL of THF at −78° C. was added a solution of 1M LiAlH$_4$ (Aldrich, 40.3 mL, 40.3 mmol) in THF. The mixture was stirred at −78° C. for 30 min, then was allowed to slowly warm up to 0° C. Cooled to −78° C., to the mixture was added 1 mL of EtOAc, 1 mL of H$_2$O, 1 mL of 2N NaOH and 1 mL of H$_2$O. The mixture was warmed up to room temperature, diluted with EtOAc, dried over Na$_2$SO$_4$, and concentrated under vacuum. The residue was chromatographed (3% MeOH/CH$_2$Cl$_2$) to yield 2.12 g (48%) of product. $^1$H NMR (400 MHz, DMSO-$d_6$) δ 8.87 (d, J=2.1 Hz, 1H), 8.24 (s, 1H), 8.03-7.97 (m, 2H), 7.75-7.70 (m, 1H), 7.62-7.58 (m, 1H), 5.48 (t, J=5.5 Hz, 1H), 4.73 (d, J=5.2 Hz, 2H). MS (EI): m/z 160 (M+H).

Example 228

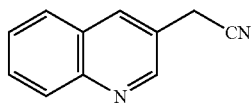

228

Quinolin-3-yl-acetonitrile (228). A solution of quinolin-3-yl-methanol (227, 3.1 g, 19.5 mmol) and thionyl chloride (Aldrich, 16.5 mL, 195 mmol) in 50 mL of benzene was refluxed for 3 h. After cooled to room temperature, the solvent was removed under reduced pressure to dryness. This crude product was used directly in the next reaction. $^1$H NMR (400 MHz, DMSO-$d_6$) δ 9.20 (s, 1H), 8.82 (s, 1H), 8.21 (d, J=7.9 Hz, 1H), 8.19 (d, J=8.1 Hz, 1H), 7.97 (t, J=7.4 Hz, 1H), 7.81 (t, J=7.5 Hz, 1H), 5.09 (s, 2H). MS (EI): m/z 178 (M+H). Quinolin-3-yl-acetonitrile was synthesized from the above crude product, KCN, NaHCO$_3$ and KI in similar manner as described in Example 221. $^1$H NMR (400 MHz, DMSO-$d_6$) δ 8.87 (d, J=2.0 Hz, 1H), 8.36 (s, 1H), 8.05 (d, J=8.3 Hz, 1H), 8.03 (d, J=7.8 Hz, 1H), 7.79 (t, J=7.3 Hz, 1H), 7.65 (t, J=7.8 Hz, 1H), 4.31 (s, 2H). MS (EI): m/z 169 (M+H).

Example 229

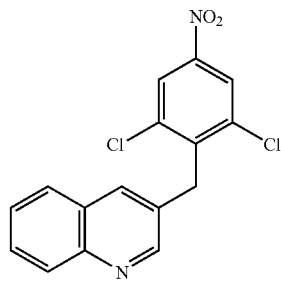

229

3-(2,6-Dichloro-4-nitro-benzyl)-quinoline (229). 3-(2,6-Dichloro-4-nitro-benzyl)-quinoline was synthesized (71%) from quinolin-3-yl-acetonitrile (228, 1.41 g, 8.4 mmol), 3,4,5-trichloronitrobenzene (Acros, 1.90 g, 8.4 mmol) and NaH (Aldrich, 740 mg, 60%, 18.5 mmol) in a similar manner in two steps as described in Example 222. $^1$H NMR (400 MHz, DMSO-$d_6$) δ 8.88 (s, 1H), 8.42 (d, J=0.9 Hz, 1H), 8.00 (d, J=8.4 Hz, 1H), 7.92-7.86 (m, 2H), 7.72 (td, J=7.0, 1.3 Hz, 1H), 7.58 (td, J=8.0, 1.0 Hz, 1H), 4.59 (s, 2H). MS (EI): m/z 333 (M+H).

Example 230

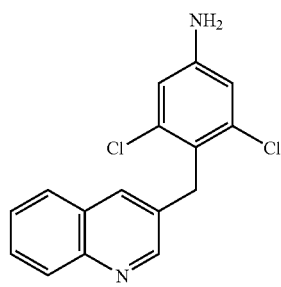

230

3,5-Dichloro-4-quinolin-3-ylmethyl-phenylamine (230). 3,5-Dichloro-4-quinolin-3-ylmethyl-phenylamine (230) was synthesized (84%) from 3-(2,6-dichloro-4-nitro-benzyl)-quinoline (229) in a similar manner as described in Examples 16-23 (Method A). $^1$H NMR (400 MHz, DMSO-$d_6$) δ 8.80 (d, J=2.2 Hz, 1H), 7.98 (d, J=8.4 Hz, 1H), 7.91 (d, J=8.0 Hz, 1H), 7.86 (s, 1H), 7.70 (td, J=7.8, 1.0 Hz, 1H), 7.13 (t, J=7.5 Hz, 1H), 6.70 (s, 2H), 5.68 (s, 2H), 4.27 (s, 2H). MS (EI): m/z 303 (M+H).

Example 231

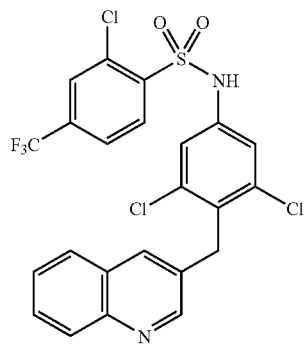

231

2-Chloro-N-(3,5-dichloro-4-quinolin-3-ylmethyl-phenyl)-4-trifluoromethyl-benzenesulfonamide (231). 2-Chloro-N-(3,5-dichloro-4-quinolin-3-ylmethyl-phenyl)-4-trifluoromethyl-benzenesulfonamide was synthesized (80%) from 3,5-dichloro-4-quinolin-3-ylmethyl-phenylamine (230), 2-chloro-4-trifluoromethylbenzenesulfonyl chloride (Maybridge) and pyridine (EM) in a similar manner as described in Examples 70-91. $^1$H NMR (400 MHz, DMSO-$d_6$) δ 11.49 (br s, 1H), 8.78 (d, J=1.9 Hz, 1H), 8.34 (d, J=8.3 Hz, 1H), 8.19 (s, 1H), 7.98 (d, J=7.0 Hz, 1H), 7.96 (d, J=7.7 Hz, 1H), 7.86 (d, J=8.0 Hz, 1H), 781 (s, 1H), 7.70 (t, J=7.6 Hz, 1H), 7.23 (t, J=7.5 Hz, 1H), 7.24 (s, 2H), 4.34 (s, 2H). MS (EI): m/z 543 (M−H).

Example 232

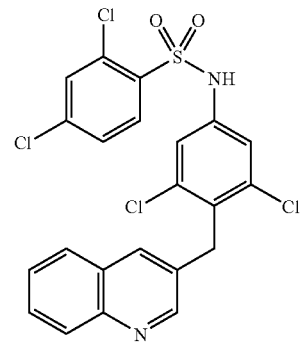

232

2,4-Dichloro-N-(3,5-dichloro-4-quinolin-3-ylmethyl-phenyl)-benzenesulfonamide (232). 2,4-Dichloro-N-(3,5-dichloro-4-quinolin-3-ylmethyl-phenyl)-benzenesulfonamide was synthesized (63%) from 3,5-dichloro-4-quinolin-3-ylmethyl-phenylamine (230), 2,4-dichlorobenzenesulfonyl chloride (Maybridge) and pyridine (EM) in a similar manner as described in Examples 70-91. $^1$H NMR (400 MHz, DMSO-$d_6$) δ 11.34 (br s, 1H), 8.78 (d, J=2.0 Hz, 1H), 8.13 (d, J=8.6 Hz, 1H), 7.97 (d, J=8.6 Hz, 1H), 7.93 (d, J=1.8 Hz, 1H), 7.88 (d, J=7.9 Hz, 1H), 7.80 (s, 1H), 7.73-7.68 (m, 2H), 7.58 (t, J=7.5 Hz, 1H), 7.21 (s, 2H), 4.34 (s, 2H). MS (EI): m/z 509 (M−H).

Example 233

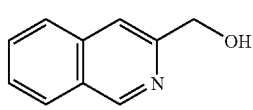

Isoquinolin-3-yl-methanol (233). Isoquinolin-3-yl-methanol was synthesized (32%) from isoquinoline-3-carboxylic acid (TCI, 5.0 g, 28.9 mmol) in a similar manner as described in Example 227. $^1$H NMR (400 MHz, DMSO-$d_6$) δ 9.24 (s, 1H), 8.10 (d, J=8.2 Hz, 1H), 7.96 (d, J=8.3 Hz, 1H), 7.83 (s, 1H), 7.75 (t, J=7.5 Hz, 1H), 7.62 (d, J=7.5 Hz, 1H), 5.50 (td, J=5.7, 0.7 Hz, 1H), 4.73 (d, J=5.7 Hz, 2H). MS (EI): m/z 160 (M+H).

Example 234

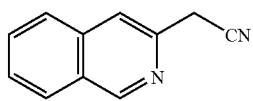

Isoquinolin-3-yl-acetonitrile (234). Isoquinolin-3-yl-acetonitrile was synthesized (80%) from isoquinolin-3-yl-methanol (233) in a similar manner as described in Example 228. $^1$H NMR (400 MHz, DMSO-$d_6$) δ 9.33 (s, 1H), 8.25 (d, J=8.1 Hz, 1H), 7.98 (d, J=8.2 Hz, 1H), 7.86 (s, 1H), 7.81 (td, J=7.6, 1.0 Hz, 1H), 7.70 (td, J=7.8, 0.6 Hz, 1H), 4.32 (s, 2H). MS (EI): m/z 169 (M+H).

Example 235

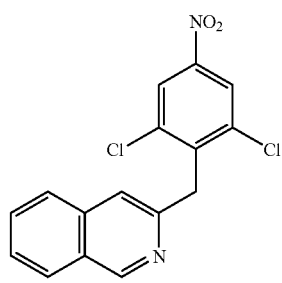

3-(2,6-Dichloro-4-nitro-benzyl)-isoquinoline (235). 3-(2,6-Dichloro-4-nitro-benzyl)-isoquinoline was synthesized (79%) from isoquinolin-3-yl-acetonitrile (234, 1.22 g, 7.26 mmol), 3,4,5-trichloronitrobenzene (Acros, 1.64 g, 7.26 mmol) and NaH (Aldrich, 640 mg, 60%, 16.0 mmol) in a similar manner in two steps as described in Example 222. $^1$H NMR (400 MHz, DMSO-$d_6$) δ 9.21 (s, 1H), 8.38 (s, 2H), 8.07 (d, J=8.2 Hz, 1H), 7.89 (d, J=8.2 Hz, 1H), 7.75 (t, J=7.5 Hz, 1H), 7.64 (t, J=7.5 Hz, 1H), 7.57 (s, 1H), 4.68 (s, 2H). MS (EI): m/z 333 (M+H).

Example 236

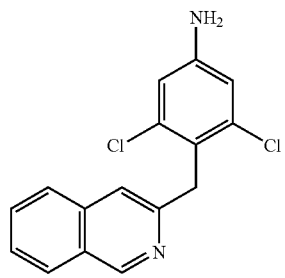

3,5-Dichloro-4-isoquinolin-3-ylmethyl-phenylamine (236). 3,5-Dichloro-4-isoquinolin-3-ylmethyl-phenylamine (236) was synthesized (84%) from 3-(2,6-dichloro-4-nitro-benzyl)-isoquinoline (235) in a similar manner as described in Examples 16-23 (Method A). $^1$H NMR (400 MHz, DMSO-$d_6$) δ 9.24 (s, 1H), 8.07 (d, J=8.2 Hz, 1H), 7.85 (d, J=8.2 Hz, 1H), 7.70 (t, J=7.5 Hz, 1H), 7.60 (t, J=7.5 Hz, 1H), 7.22 (s, 1H), 6.70 (s, 2H), 5.65 (s, 2H), 4.37 (s, 2H). MS (EI): m/z 303 (M+H).

Example 237

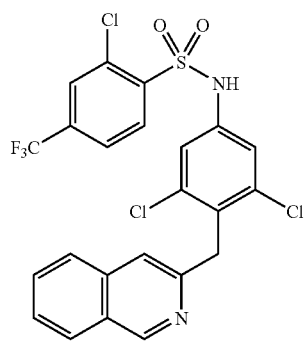

2-Chloro-N-(3,5-dichloro-4-isoquinolin-3-ylmethyl-phenyl)-4-trifluoromethyl-benzenesulfonamide (237). 2-Chloro-N-(3,5-dichloro-4-isoquinolin-3-ylmethyl-phenyl)-4-trifluoromethyl-benzenesulfonamide was synthesized (65%) from 3,5-dichloro-4-isoquinolin-3-ylmethyl-phenylamine (236), 2-chloro-4-trifluoromethylbenzenesulfonyl chloride (Maybridge) and pyridine (EM) in a similar manner as described in Examples 70-91. $^1$H NMR (400 MHz, DMSO-$d_6$) δ 11.46 (br s, 1H), 9.19 (s, 1H), 8.35 (d, J=8.2 Hz, 1H), 8.19 (d, J=1.1 Hz, 1H), 8.04 (d, J=8.0 Hz, 1H), 7.99 (dd, J=8.3, 1.2 Hz, 1H), 7.83 (d, J=8.2 Hz, 1H), 7.71 (td, J=7.5, 1.0 Hz, 1H), 7.60 (td, J=7.5, 0.8 Hz, 1H), 7.22 (s, 2H), 4.42 (s, 2H). MS (EI): m/z 543 (M−H).

Example 238

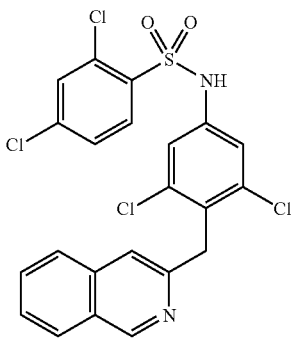

2,4-Dichloro-N-(3,5-dichloro-4-isoquinolin-3-ylmethyl-phenyl)-benzenesulfonamide (238). 2,4-Dichloro-N-(3,5-dichloro-4-isoquinolin-3-ylmethyl-phenyl)-benzenesulfonamide was synthesized (63%) from 3,5-dichloro-4-isoquinolin-3-ylmethyl-phenylamine (236), 2,4-dichlorobenzenesulfonyl chloride (Maybridge) and pyridine (EM) in a similar manner as described in Examples 70-91. $^1$H NMR (400 MHz, DMSO-$d_6$) δ 11.30 (br s, 1H), 9.19 (s, 1H), 8.14 (d, J=8.6 Hz, 1H), 8.04 (d, J=8.1 Hz, 1H), 7.93 (d, J=2.1 Hz, 1H), 7.83 (d, J=8.2 Hz, 1H), 7.74-7.68 (m, 2H), 7.60 (td, J=7.5, 1.0 Hz, 1H), 7.31 (s, 1H), 7.20 (s, 2H), 4.42 (s, 2H). MS (EI): m/z 509 (M–H).

Example 250

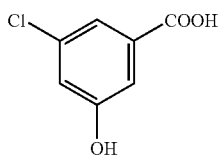

3-Chloro-5-hydroxy-benzoic acid (250). To a solution of 3,5-dichlorobenzoic acid (Aldrich, 19.2 g, 100 mmol) in HMPA was added NaOMe (Aldrich, 27.0 g, 500 mmol). The mixture was heated at 150° C. for 2 d. After cooled to room temperature, the reaction mixture was poured to ice/water, acidified to pH 1 with con. HCl, extracted 3× with EtOAc (400 mL). The organic layers were washed twice with a brine solution (300 mL), dried over Na$_2$SO$_4$. Removal of the solvent under reduced pressure gave a crude product.

To a stirred solution of the above product in 100 mL of AcOH at 50° C. was added 140 mL of 48% HBr (Aldrich). The mixture was then refluxed overnight. After cooled to room temperature, the reaction mixture was poured to ice/water. The desired product was collected by filtration followed by washing with water. $^1$H NMR (400 MHz, DMSO-$d_6$) δ 13.3 (br s, 1H), 10.31 (s, 1H), 7.33 (t, J=1.6 Hz, 1H), 7.29 (dd, J=2.2, 1.5 Hz, 1H), 7.04 (t, J=2.1 Hz, 1H).

Example 251

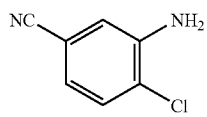

3-Amino-4-chloro-benzonitrile (251). 3-Amino-4-chloro-benzonitrile was synthesized (98%) from 4-chloro-3-nitro-benzonitrile (Fluka) in a similar manner as described in Examples 16-23 (Method A). $^1$H NMR (400 MHz, DMSO-$d_6$) δ 7.39 (d, J=8.1 Hz, 1H), 7.10 (d, J=2.0 Hz, 1H), 6.93 (dd, J=8.2, 2.0 Hz, 1H), 5.89 (s, 2H).

Example 252

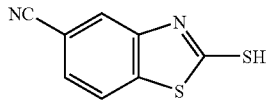

2-Mercapto-benzothiazole-5-carbonitrile (252). To a solution of 3-amino-4-chloro-benzonitrile (Example 251, 9.0 g, 59 mmol) in 90 mL of DMF was added O-ethylxanthic acid potassium salt (Aldrich, 21.23 g, 133 mmol). The mixture was heated to 115° C. for 4 h. After cooled to room temperature, the mixture was diluted with ice/water and was acidified to pH 2 with 2N HCl. Filtration followed by washing with water gave a crude product, which was recrystallized from EtOH/water to give 5.6 g (49%) of product. $^1$H NMR (400 MHz, DMSO-$d_6$) δ 14.10 (br s, 1H), 7.90 (d, J=8.3 Hz, 1H), 7.69 (dd, J=8.3, 1.1 Hz, 1H), 7.60 (s, 1H). MS (EI): m/z 191 (M–H).

Examples 253-262

The compounds in Table 12 were prepared using the method described in Example 253 (Method A in Table 12) or Example 255 (Method B in Table 12) below, as indicated.

TABLE 12

| Compound | X | Method |
|---|---|---|
| 253 | 5-Cl | A |
| 254 | 5-CN | A |
| 255 | 4-Cl | B |
| 256 | 4-Me | B |
| 257 | 4-OMe | B |
| 258 | 6-Me | B |
| 259 | 6-Cl | B |
| 260 | 6-F | B |
| 261 | 6-OMe | B |
| 262 | 6-COOEt | B |

Example 253

2,5-Dichloro-benzothiazole (253). To 5-chloro-benzothiazole-2-thiol (Aldrich, 10.09 g, 50 mmol) was added SO$_2$Cl$_2$, and the mixture was stirred at ambient temperature for 1 h then heated at 60° C. for 30 min. After cooled to room temperature, the mixture was poured to ice/water and stirred for 30 min. The desired product was collected by filtration followed by washing with water. $^1$H NMR (400 MHz, DMSO-$d_6$) δ 8.16 (d, J=8.7 Hz, 1H), 8.09 (d, J=2.1 Hz, 1H), 7.58 (dd, J=8.7, 2.1 Hz, 1H).

Example 254

2-Chloro-benzothiazole-5-carbonitrile (254). 2-Chloro-benzothiazole-5-carbonitrile was synthesized from 2-mercapto-benzothiazole-5-carbonitrile (252) in a similar manner as described in Example 253. ¹H NMR (400 MHz, DMSO-d₆) δ 8.55 (d, J=1.5 Hz, 1H), 8.35 (d, J=8.4 Hz, 1H), 7.92 (dd, J=8.4, 1.5 Hz, 1H).

Example 255

2,4-Dichloro-benzothiazole (255). Anhydrous CuCl₂ (Aldrich, 4.37 g, 32.5 mmol), t-butyl nitrite (Aldrich, 4.83 mL, 40.6 mmol) and anhydrous acetonitrile (EM, 50 mL) were added to a 3-necked round-bottomed flask equipped with a reflux condenser, an additional funnel and a gas outlet tube. The mixture was warmed to 65° C. and a suspension of 2-amino-4-chlorobenzothiazole in 50 mL of acetonitrile. During the addition, the reaction mixture tuned to black and gas evolved. After gas evolution is complete, the reaction was allowed to reach room temperature. The reaction mixture was poured to 300 mL of 20% aqueous HCl, extracted 3× with EtOAc (400 mL). The organic layers were washed twice with a brine solution (300 mL), dried over Na₂SO₄ and concentrated. The residue was purified by chromatography with 60% CH₂Cl₂/hexanes to give 4.8 g of product. ¹H NMR (400 MHz, DMSO-d₆) δ 8.10 (dd, J=8.1, 1.0 Hz, 1H), 7.68 (dd, J=7.9, 1.0 Hz, 1H), 7.51 (t, J=8.0 Hz, 1H).

Example 256

2-Chloro-4-methyl-benzothiazole (256). 2-Chloro-4-methyl-benzothiazole was synthesized from 2-amino-4-methyl-benzothiazole (Aldrich) in a similar manner as described in Example 255. ¹H NMR (400 MHz, DMSO-d₆) δ 7.91 (dd, J=7.7, 1.5 Hz, 1H), 7.42-7.38 (m, 2H), 2.60 (s, 3H).

Example 257

2-Chloro-4-methoxy-benzothiazole (257). 2-Chloro-4-methoxy-benzothiazole was synthesized from 2-amino-4-methoxy-benzothiazole (Aldrich) in a similar manner as described in Example 255. ¹H NMR (400 MHz, DMSO-d₆) δ 7.62 (dd, J=8.2, 0.7 Hz, 1H), 7.44 (t, J=8.1 Hz, 1H), 7.10 (d, J=8.1 Hz, 1H), 3.94 (s, 3H).

Example 258

2-Chloro-6-methyl-benzothiazole (258). 2-Chloro-6-methyl-benzothiazole was synthesized from 2-amino-6-methyl-benzothiazole (Aldrich) in a similar manner as described in Example 255. ¹H NMR (400 MHz, DMSO-d₆) δ 7.89 (d, J=0.7 Hz, 1H), 7.84 (t, J=8.3 Hz, 1H), 7.38 (dd, J=8.3, 1.3 Hz, 1H), 2.73 (s, 3H).

Example 259

2,6-Dichloro-benzothiazole (259). 2,6-Dichloro-benzothiazole was synthesized from 2-amino-6-chloro-benzothiazole (Aldrich) in a similar manner as described in Example 255. ¹H NMR (400 MHz, DMSO-d₆) δ 7.03 (d, J=2.2 Hz, 1H), 7.98 (d, J=8.7 Hz, 1H), 7.60 (dd, J=8.7, 2.2 Hz, 1H).

Example 260

2-Chloro-6-fluoro-benzothiazole (260). 2-Chloro-6-fluoro-benzothiazole was synthesized from 2-amino-6-fluoro-benzothiazole (Aldrich) in a similar manner as described in Example 255. ¹H NMR (400 MHz, DMSO-d₆) δ 8.04 (dd, J=8.9, 2.1 Hz, 1H), 8.01 (dd, J=8.7, 5.0 Hz, 1H), 7.45 (td, J=8.1, 2.7 Hz, 1H).

Example 261

2-Chloro-6-methoxy-benzothiazole (261). 2-Chloro-6-methoxy-benzothiazole was synthesized from 2-amino-6-methoxy-benzothiazole (Aldrich) in a similar manner as described in Example 255. ¹H NMR (400 MHz, DMSO-d₆) δ 7.85 (d, J=8.6 Hz, 1H), 7.69 (s, 1H), 7.14 (d, J=8.1 Hz, 1H), 3.82 (s, 3H).

Example 262

2-Chloro-benzothiazole-6-carboxylic acid ethyl ester (262). 2-Chloro-benzothiazole-6-carboxylic acid ethyl ester was synthesized from 2-amino-benzothiazole-6-carboxylic acid ethyl ester (Astatech) in a similar manner as described in Example 255. ¹H NMR (400 MHz, DMSO-d₆) δ 8.80 (d, J=1.0 Hz, 1H), 8.09 (dd, J=8.6, 1.6 Hz, 1H), 8.06 (d, J=8.5 Hz, 1H), 4.35 (q, J=7.1 Hz, 2H), 1.35 (t, J=7.1 Hz, 3H).

Example 263

[3-Chloro-5-(5-chloro-benzothiazol-2-yloxy)-phenyl]-carbamic acid tert-butyl ester (263). To a solution of 3-Chloro-5-hydroxy-benzoic acid (Example 250, 1.73 g, 10 mmol) in DMF was added NaH (Aldrich, 840 mg, 60%, 21 mmol). The mixture was stirred for 10 min, then 2,5-dichlorobenzothiazole (Example 253, 2.03 g, 10 mmol) was added. The mixture was heated at 60° C. till there is no starting material remained by TLC. After cooled to room temperature, the mixture was poured to ice/1N HCl, extracted 3× with EtOAc (100 mL). The organic layers were washed twice with a brine solution (100 mL), dried over Na₂SO₄ and concentrated. The resulting material was used directly in the next reaction.

To a solution of the above product in 20 mL of tert-butanol was added diphenylphosphoryl azide (Aldrich, 2.16 mL, 10 mmol) and triethylamine (Aldrich, 1.4 mL, 10 mmol). The mixture was refluxed overnight, cooled to room temperature and concentrated to dryness under reduced pressure. The residue was purified by chromatography with 50%-70% CH₂Cl₂/hexanes to give 2.10 g of product. ¹H NMR (400 MHz, DMSO-d₆) δ 9.85 (br s, 1H), 8.01 (d, J=8.6 Hz, 1H), 7.84 (d, J=2.0 Hz, 1H), 7.53 (b s, 1H), 7.50 (t, J=2.0 Hz, 1H), 7.42 (dd, J=8.6, 2.1 Hz, 1H), 7.26 (t, J=2.0 Hz, 1H), 1.47 (s, 9H). MS (EI): m/z 411 (M+H).

TABLE 13

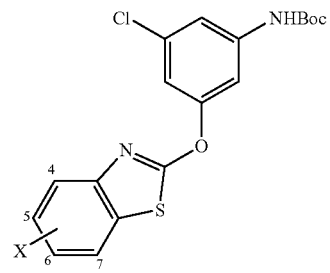

| Compound | X |
|---|---|
| 263 | 5-Cl |
| 264 | 5-CN |
| 265 | 4-Cl |
| 266 | 4-Me |
| 267 | 4-OMe |
| 268 | 6-Me |
| 269 | 6-Cl |

TABLE 13-continued

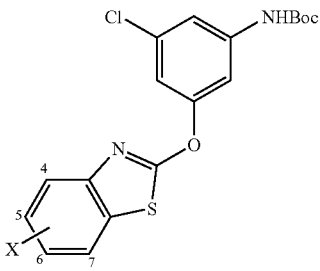

| Compound | X |
|---|---|
| 270 | 6-F |
| 271 | 6-OMe |
| 272 | 6-COOEt |

The compounds of Table 13 were prepared in a similar manner as described in Example 263.

Example 264

[3-Chloro-5-(5-cyano-benzothiazol-2-yloxy)-phenyl]-carbamic acid tert-butyl ester (264). $^1$H NMR (400 MHz, DMSO-$d_6$) δ 9.87 (br s, 1H), 8.26 (d, J=1.5 Hz, 1H), 8.22 (d, J=8.3 Hz, 1H), 7.77 (dd, J=8.3, 1.6 Hz, 1H), 7.53 (t, J=1.8 Hz, 1H), 7.51 (t, J=1.9 Hz, 1H), 7.29 (t, J=2.0 Hz, 1H), 1.47 (s, 9H). MS (EI): m/z 400 (M–H).

Example 265

[3-Chloro-5-(4-chloro-benzothiazol-2-yloxy)-phenyl]-carbamic acid tert-butyl ester (265). $^1$H NMR (400 MHz, DMSO-$d_6$) δ 9.89 (br s, 1H), 7.95 (dd, J=8.0, 1.0 Hz, 1H), 7.56 (d, J=8.0, 1.0 Hz, 1H), 7.52 (t, J=2.0 Hz, 1H), 7.36 (t, J=8.0 Hz, 1H), 7.35-7.31 (m, 2H), 1.47 (s, 9H). MS (EI): m/z 355 ($M^+$–$C_4H_8$).

Example 266

[3-Chloro-5-(4-methyl-benzothiazol-2-yloxy)-phenyl]-carbamic acid tert-butyl ester (266). $^1$H NMR (400 MHz, DMSO-$d_6$) δ 9.85 (br s, 1H), 7.76 (dd, J=7.2, 1.6 Hz, 1H), 7.56 (t, J=1.8 Hz, 1H), 7.53 (t, J=1.7 Hz, 1H), 7.30-7.22 (m, 3H), 2.49 (s, 3H), 1.47 (s, 9H). MS (EI): m/z 389 (M–H).

Example 267

[3-Chloro-5-(4-methoxy-benzothiazol-2-yloxy)-phenyl]-carbamic acid tert-butyl ester (267). $^1$H NMR (400 MHz, DMSO-$d_6$) δ 9.86 (br s, 1H), 7.52-7.50 (m, 2H), 7.45 (t, J=1.9 Hz, 1H), 7.31 (t, J=8.1 Hz, 1H), 7.21 (t, J=2.0 Hz, 1H), 7.03 (d, J=8.1 Hz, 1H), 3.86 (s, 3H), 1.47 (s, 9H). MS (EI): m/z 407 (M+H).

Example 268

[3-Chloro-5-(6-methyl-benzothiazol-2-yloxy)-phenyl]-carbamic acid tert-butyl ester (268). $^1$H NMR (400 MHz, DMSO-$d_6$) δ 9.85 (br s, 1H), 7.76 (s, 1H), 7.60 (d, J=8.2 Hz, 1H), 7.52 (br s, 1H), 7.47 (t, J=1.9 Hz, 1H), 7.26 (dd, J=8.2, 1.2 Hz, 1H), 7.22 (t, J=2.0 Hz 1H), 2.40 (s, 3H), 1.47 (s, 9H). MS (EI): m/z 389 (M–H).

Example 269

[3-Chlor-5-(6-chloro-benzothiazol-2-yloxy)-phenyl]-carbamic acid tert-butyl ester (269). $^1$H NMR (400 MHz, DMSO-$d_6$) δ 9.85 (br s, 1H), 8.14 (d, J=2.1 Hz, 1H), 7.73 (d, J=8.6 Hz, 1H), 7.53-7.45 (m, 3H), 7.26 (t, J=2.0 Hz, 1H), 1.47 (s, 9H). MS (EI): m/z 355 ($M^+$–$C_4H_8$).

Example 270

[3-Chloro-5-(6-fluoro-benzothiazol-2-yloxy)-phenyl]-carbamic acid tert-butyl ester (270). $^1$H NMR (400 MHz, DMSO-$d_6$) δ 9.85 (br s, 1H), 7.92 (dd, J=8.7, 2.7 Hz, 1H), 7.75 (dd, J=8.9, 4.8 Hz, 1H), 7.52 (br s, 1H), 7.49 (br s, 1H), 7.31 (td, J=9.0, 2.7 Hz, 1H), 7.25 (t, J=2.0 Hz, 1H), 1.47 (s, 9H). MS (EI): m/z 355 ($M^+$–$C_4H_8$).

Example 271

[3-Chloro-5-(6-methoxy-benzothiazol-2-yloxy)-phenyl]-carbamic acid tert-butyl ester (271). $^1$H NMR (400 MHz, DMSO-$d_6$) δ 9.84 (br s, 1H), 7.62 (d, J=8.8 Hz, 1H), 7.58 (d, J=2.5 Hz, 1H), 7.51 (br s, 1H), 7.45 (br s, 1H), 7.21 (t, J=2.0 Hz, 1H), 7.03 (dd, J=8.9, 2.6 Hz, 1H), 3.79 (s, 3H), 1.47 (s, 9H). MS (EI): m/z 407 (M+H).

Example 272

2-(3-tert-Butoxycarbonylamino-5-chloro-phenoxy)-benzothiazole-6-carboxylic acid ethyl ester (272). $^1$H NMR (400 MHz, DMSO-$d_6$) δ 9.98 (br s, 1H), 8.66 (d, J=1.6 Hz, 1H), 8.01 (dd, J=8.5, 1.6 Hz, 1H), 7.81 (d, J=8.5 Hz, 1H), 7.54 (br s, 1H), 7.52 (br s, 1H), 7.30 (t, J=1.8 Hz, 1H), 4.34 (q, J=7.1 Hz, 1H), 1.47 (s, 9H), 1.34 (t, J=7.1 Hz, 3H). MS (EI): m/z 393 ($M^+$–$C_4H_8$).

Example 273

3-Chloro-5-(5-chloro-benzothiazol-2-yloxy)-phenylamine (273). To [3-chloro-5-(5-chloro-benzothiazol-2-yloxy)-phenyl]-carbamic acid tert-butyl ester (263, 1.17 g, 2.85 mmol) was added trifluoroacetic acid. The mixture was stirred at ambient temperature for 5 h, at which time TLC showed there was no starting material remained. The mixture was concentrated to dryness under reduced pressure, dissolved in EtOAc. The organic solution was washed with 1N NaOH, washed twice with a brine solution, dried over $Na_2SO_4$ and concentrated. The residue was purified by chromatography with $CH_2Cl_2$ to give 785 mg of product. $^1$H NMR (400 MHz, DMSO-$d_6$) δ 7.98 (d, J=8.6 Hz, 1H), 7.82 (d, J=2.0 Hz, 1H), 7.40 (dd, J=8.6, 2.0 Hz, 1H), 6.62 (t, J=1.9 Hz, 1H), 6.58 (t, J=1.8 Hz, 1H), 6.50 (t, J=1.9 Hz, 1H), 5.81 (s, 2H). MS (EI): m/z 311 (M+H).

Examples 274-282

The compounds in Table 14 were prepared from compounds in Table 13 in a similar manner as described in Example 273 above.

TABLE 14

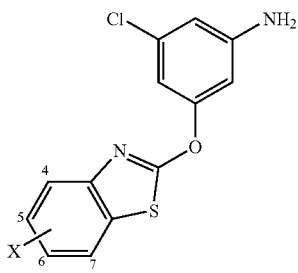

| Compound | X |
|---|---|
| 273 | 5-Cl |
| 274 | 5-CN |
| 275 | 4-Cl |
| 276 | 4-Me |
| 277 | 4-OMe |
| 278 | 6-Me |
| 279 | 6-Cl |
| 280 | 6-F |
| 281 | 6-OMe |
| 282 | 6-COOEt |

Example 274

2-(3-Amino-5-chloro-phenoxy)-benzothiazole-5-carbonitrile (274). $^1$H NMR (400 MHz, DMSO-d$_6$) δ 8.25 (d, J=1.2 Hz, 1H), 7.82 (d, J=2.0 Hz, 1H), 7.76 (dd, J=8.3, 1.6 Hz, 1H), 6.65 (t, J=2.0 Hz, 1H), 6.59 (t, J=1.9 Hz, 1H), 6.52 (t, J=2.0 Hz, 1H), 5.81 (s, 2H). MS (EI): m/z 302 (M+H).

Example 275

3-Chloro-5-(4-chloro-benzothiazol-2-yloxy)-phenylamine (275). $^1$H NMR (400 MHz, DMSO-d$_6$) δ 7.92 (dd, J=8.0, 1.0 Hz, 1H), 7.54 (dd, J=7.9, 1.0 Hz, 1H), 7.33 (t, J=8.0 Hz, 1H), 6.66 (t, J=2.0 Hz, 1H), 6.60 (t, J=1.9 Hz, 1H), 6.52 (t, J=2.0 Hz, 1H), 5.76 (s, 2H). MS (EI): m/z 311 (M+H).

Example 276

3-Chloro-5-(4-methyl-benzothiazol-2-yloxy)-phenylamine (276). $^1$H NMR (400 MHz, DMSO-d$_6$) δ 7.74 (dd, J=7.5, 1.0 Hz, 1H), 7.27 (dd, J=7.3, 1.3 Hz, 1H), 7.23 (t, J=7.5 Hz, 1H), 6.62 (t, J=2.0 Hz, 1H), 6.57 (t, J=1.9 Hz, 1H), 6.51 (t, J=2.0 Hz, 1H), 5.82 (s, 2H), 2.50 (s, 3H). MS (EI): m/z 291 (M+H).

Example 277

3-Chloro-5-(4-methoxy-benzothiazol-2-yloxy)-phenylamine (277). $^1$H NMR (400 MHz, DMSO-d$_6$) δ 7.49 (dd, J=8.0, 0.9 Hz, 1H), 7.29 (t, J=8.1 Hz, 1H), 7.02 (d, J=8.1 Hz, 1H), 6.57 (t, J=2.0 Hz, 1H), 6.56 (t, J=1.9 Hz, 1H), 6.46 (t, J=2.0 Hz, 1H), 5.80 (s, 2H), 3.87 (s, 3H). MS (EI): m/z 307 (M+H).

Example 278

3-Chloro-5-(6-methyl-benzothiazol-2-yloxy)-phenylamine (278). $^1$H NMR (400 MHz, DMSO-d$_6$) δ 7.73 (d, J=0.4 Hz, 1H), 7.60 (d, J=8.2 Hz, 1H), 7.25 (dd, J=8.3, 1.6 Hz, 1H), 6.58 (t, J=2.0 Hz, 1H), 6.56 (t, J=1.9 Hz, 1H), 6.49 (t, J=2.0 Hz, 1H), 5.76 (s, 2H), 2.39 (s, 3H). MS (EI): m/z 291 (M+H).

Example 279

3-Chloro-5-(6-chloro-benzothiazol-2-yloxy)-phenylamine (279). $^1$H NMR (400 MHz, DMSO-d$_6$) δ 8.11 (d, J=2.2 Hz, 1H), 7.72 (d, J=8.6 Hz, 1H), 7.47 (dd, J=8.7, 2.2 Hz, 1H), 6.62 (t, J=2.0 Hz, 1H), 6.57 (t, J=1.8 Hz, 1H), 6.50 (t, J=2.0 Hz, 1H), 5.82 (s, 2H). MS (EI): m/z 311 (M+H).

Example 280

3-Chloro-5-(6-fluoro-benzothiazol-2-yloxy)-phenylamine (280). $^1$H NMR (400 MHz, DMSO-d$_6$) δ 7.88 (dd, J=8.7, 2.7 Hz, 1H), 7.74 (dd, J=8.9, 4.9 Hz, 1H), 7.30 (td, J=9.0, 2.7 Hz, 1H), 6.60 (t, J=2.0 Hz, 1H), 6.56 (t, J=1.9 Hz, 1H), 6.50 (t, J=2.0 Hz, 1H), 5.81 (s, 2H). MS (EI): m/z 295 (M+H).

Example 281

3-Chloro-5-(6-methoxy-benzothiazol-2-yloxy)-phenylamine (281). $^1$H NMR (400 MHz, DMSO-d$_6$) δ 7.62 (d, J=8.9 Hz, 1H), 7.56 (dd, J=2.7 Hz, 1H), 7.03 (dd, J=8.8, 2.6 Hz, 1H), 6.56 (t, J=2.0 Hz, 1H), 6.54 (t, J=1.8 Hz, 1H), 6.47 (t, J=2.0 Hz, 1H), 5.78 (s, 2H). MS (EI): m/z 307 (M+H).

Example 282

2-(3-Amino-5-chloro-phenoxy)-benzothiazole-6-carboxylic acid ethyl ester (282). $^1$H NMR (400 MHz, DMSO-d$_6$) δ 8.62 (d, J=1.6 Hz, 1H), 8.00 (dd, J=8.5, 1.8 Hz, 1H), 7.80 (d, J=8.5 Hz, 1H), 6.65 (t, J=2.0 Hz, 1H), 6.59 (t, J=1.9 Hz, 1H), 6.52 (t, J=2.0 Hz, 1H), 5.84 (s, 2H), 4.33 (q, J=7.1 Hz, 2H), 1.33 (t, J=7.1 Hz, 3H). MS (EI): m/z 349 (M+H).

Example 282

The compounds in Table 15 were prepared from compounds in Table 14 and corresponding arylsulfonyl chloride using the one of the methods of Examples 70-91.

TABLE 15

| Compound | X | A | B |
|---|---|---|---|
| 283 | 5-Cl | CF$_3$ | H |
| 284 | 5-Cl | Cl | H |
| 285 | 5-Cl | Cl | Me |
| 286 | 5-CN | CF$_3$ | H |
| 287 | 5-CN | Cl | H |
| 288 | 5-CN | Cl | Me |
| 290 | 4-Cl | CF$_3$ | H |
| 291 | 4-Cl | Cl | H |
| 292 | 4-Cl | Cl | Me |
| 293 | 4-Me | CF$_3$ | H |
| 294 | 4-Me | Cl | H |
| 295 | 4-Me | Cl | Me |

TABLE 15-continued

[Structure: benzothiazole linked via O to a phenyl ring (with Cl substituent) bearing an NH-SO2 group connected to another phenyl ring with substituents A and B and Cl; benzothiazole positions 4,5,6,7 labeled with X at position 6]

| Compound | X | A | B |
|---|---|---|---|
| 296 | 4-OMe | CF₃ | H |
| 297 | 4-OMe | Cl | H |
| 298 | 4-OMe | Cl | Me |
| 299 | 6-Me | CF₃ | H |
| 300 | 6-Me | Cl | H |
| 301 | 6-Me | Cl | Me |
| 302 | 6-Cl | CF₃ | H |
| 303 | 6-Cl | Cl | H |
| 304 | 6-F | CF₃ | H |
| 305 | 6-F | Cl | H |
| 306 | 6-F | Cl | Me |
| 307 | 6-OMe | CF₃ | H |
| 308 | 6-OMe | Cl | H |
| 309 | 6-OMe | Cl | Me |
| 310 | 6-COOEt | CF₃ | H |
| 311 | 6-COOEt | Cl | H |

Example 283

2-Chloro-N-[3-chloro-5-(5-chloro-benzothiazol-2-yloxy)-phenyl]-4-trifluoromethyl-benzenesulfonamide (283). $^1$H NMR (400 MHz, DMSO-d$_6$) δ 11.53 (s, 1H), 8.31 (d, J=8.5 Hz, 1H), 8.18 (s, 1H), 8.00 (d, J=8.6 Hz, 1H), 7.91 (d, J=8.5 Hz, 1H), 7.76 (d, J=2.1 Hz, 1H), 7.43 (dd, J=8.6, 2.1 Hz, 1H), 7.38 (t, J=1.9 Hz, 1H), 7.12-7.10 (m, 2H). MS (EI): m/z 551 (M–H).

Example 284

2,4-Dichloro-N-[3-chloro-5-(5-chloro-benzothiazol-2-yloxy)-phenyl]-benzenesulfonamide (284). $^1$H NMR (400 MHz, DMSO-d$_6$) δ 11.38 (s, 1H), 8.10 (d, J=8.6 Hz, 1H), 8.01 (d, J=8.6 Hz, 1H), 7.93 (d, J=2.1 Hz, 1H), 7.78 (d, J=2.0 Hz, 1H), 7.59 (dd, J=8.6, 2.1 Hz, 1H), 7.43 (dd, J=8.6, 2.1 Hz, 1H), 7.36 (t, J=2.0 Hz, 1H), 7.10-7.06 (m, 2H). MS (EI): m/z 517 (M–H).

Example 285

2,4-Dichloro-N-[3-chloro-5-(5-chloro-benzothiazol-2-yloxy)-phenyl]-5-methyl-benzenesulfonamide (285). $^1$H NMR (400 MHz, DMSO-d$_6$) δ 11.35 (s, 1H), 8.11 (s, 1H), 8.00 (d, J=8.6 Hz, 1H), 7.86 (s, 1H), 7.73 (d, J=2.1 Hz, 1H), 7.43 (dd, J=8.6, 2.1 Hz, 1H), 7.34 (t, J=2.0 Hz, 1H), 7.11-7.06 (m, 2H), 2.19 (s, 3H). MS (EI): m/z 531 (M–H).

Example 286

2-Chloro-N-[3-chloro-5-(5-cyano-benzothiazol-2-yloxy)-phenyl]-4-trifluoromethyl-benzenesulfonamide (286). $^1$H NMR (400 MHz, DMSO-d$_6$) δ 11.56 (s, 1H), 8.32 (d, J=8.2 Hz, 1H), 8.24-8.16 (m, 3H), 7.91 (dd, J=8.3, 1.2 Hz, 1H), 7.78 (dd, J=8.3, 1.6 Hz, 1H), 7.41 (t, J=2.0 Hz, 1H), 7.15-7.11 (m, 2H). MS (EI): m/z 542 (M–H).

Example 287

2,4-Dichloro-N-[3-chloro-5-(5-cyano-benzothiazol-2-yloxy)-phenyl]-benzenesulfonamide (287). $^1$H NMR (400 MHz, DMSO-d$_6$) δ 11.40 (s, 1H), 8.22 (d, J=8.3 Hz, 1H), 8.19 (d, J=1.5 Hz, 1H), 8.10 (d, J=8.6 Hz, 1H), 7.93 (d, J=2.0 Hz, 1H), 7.79 (dd, J=8.3, 1.6 Hz, 1H), 7.59 (dd, J=8.6, 2.1 Hz, 1H), 7.39 (t, J=1.9 Hz, 1H), 7.12-7.08 (m, 2H). MS (EI): m/z 508 (M–H).

Example 288

2,4-Dichloro-N-[3-chloro-5-(5-cyano-benzothiazol-2-yloxy)-phenyl]-5-methyl-benzenesulfonamide (288). $^1$H NMR (400 MHz, DMSO-d$_6$) δ 11.37 (s, 1H), 8.21 (d, J=8.3 Hz, 1H), 8.14 (d, J=1.5 Hz, 1H), 8.12 (s, 1H), 7.87 (s, 1H), 7.79 (dd, J=8.3, 1.5 Hz, 1H), 7.36 (t, J=1.9 Hz, 1H), 7.11-7.06 (m, 2H), 2.16 (s, 3H). MS (EI): m/z 522 (M–H).

Example 289

[Structure: 2-chloro-4-trifluoromethyl benzenesulfonamide linked to a 3-chloro-5-(benzothiazol-2-yloxy)phenyl with a tetrazole substituent on the benzothiazole]

2-Chloro-N-{3-chloro-5-[5-(1H-tetrazol-5-yl)-benzothiazol-2-yloxy]-phenyl}-4-trifluoromethyl-benzenesulfonamide (289). To a solution of 2-Chloro-N-[3-chloro-5-(5-cyano-benzothiazol-2-yloxy)-phenyl]-4-trifluoromethyl-benzenesulfonamide (Example 286, 55 mg, 0.1 mmol) in 5 mL of toluene was added azidotrimethylsilane (Aldrich, 26 uL, 0.2 mmol) and dibutyltin oxide (Aldrich, 3 mg, 0.01 mmol). The mixture was heated at 90° C. overnight till there was no starting material remained by TLC. Cooled to room temperature, 1N HCl and EtOAc was added. The mixture was extracted 3× with EtOAc (30 mL). The organic layers were washed twice with a brine solution (300 mL), dried over Na$_2$SO$_4$ and concentrated. The residue was purified by chromatography, eluted with 10% EtOAc/CH$_2$Cl$_2$ then 10% MeOH/CH$_2$Cl$_2$ to give 50 mg (85%) of product. $^1$H NMR (400 MHz, DMSO-d$_6$) δ 8.33 (d, J=8.2 Hz, 1H), 8.30 (d, J=1.6 Hz, 1H), 8.21 (d, J=8.5 Hz, 1H), 8.19 (s, 1H), 8.03 (dd, J=8.4, 1.6 Hz, 1H), 7.93 (d, J=8.4 Hz, 1H), 7.44 (t, J=2.0 Hz, 1H), 7.18 (t, J=2.0 Hz, 1H), 7.12 (t, J=1.9 Hz, 1H). MS (EI): m/z 585 (M–H).

Example 290

2-Chloro-N-[3-chloro-5-(4-chloro-benzothiazol-2-yloxy)-phenyl]-4-trifluoromethyl-benzenesulfonamide (290). $^1$H NMR (400 MHz, DMSO-d$_6$) δ 11.56 (s, 1H), 8.32 (d, J=8.3 Hz, 1H), 8.18 (d, J=1.2 Hz, 1H), 7.93 (dd, J=8.1, 1.0

Hz, 1H), 7.90 (dd, J=8.3, 2.1 Hz, 1H), 7.56 (dd, J=7.9, 1.0 Hz, 1H), 7.44 (t, J=2.0 Hz, 1H), 7.36 (t, J=8.0 Hz, 1H), 7.17 (t, J=2.0 Hz, 1H), 7.13 (t, J=1.9 Hz, 1H). MS (EI): m/z 551 (M–H).

Example 291

2,4-Dichloro-N-[3-chloro-5-(4-chloro-benzothiazol-2-yloxy)-phenyl]-benzenesulfonamide (291). $^1$H NMR (400 MHz, DMSO-$d_6$) δ 11.41 (s, 1H), 8.10 (d, J=8.5 Hz, 1H), 7.95 (dd, J=8.0, 1.0 Hz, 1H), 7.91 (d, J=2.1 Hz, 1H), 7.58 (dd, J=8.5, 2.0 Hz, 1H), 7.56 (dd, J=8.0, 1.0 Hz, 1H), 7.41 (t, J=2.0 Hz, 1H), 7.37 (t, J=8.0 Hz, 1H), 7.13 (t, J=2.0 Hz, 1H), 7.10 (t, J=1.9 Hz, 1H). MS (EI): m/z 517 (M–H).

Example 292

2,4-Dichloro-N-[3-chloro-5-(4-chloro-benzothiazol-2-yloxy)-phenyl]-5-methyl-benzenesulfonamide (292). $^1$H NMR (400 MHz, DMSO-$d_6$) δ 11.36 (s, 1H), 8.12 (s, 1H), 7.93 (dd, J=8.0, 1.0 Hz, 1H), 7.84 (s, 1H), 7.56 (dd, J=8.0, 1.0 Hz, 1H), 7.38 (t, J=2.0 Hz, 1H), 7.36 (t, J=8.0 Hz, 1H), 7.14 (t, J=2.0 Hz, 1H), 7.11 (t, J=1.9 Hz, 1H), 2.19 (s, 3H). MS (EI): m/z 531 (M–H).

Example 293

2-Chloro-N-[3-chloro-5-(4-methyl-benzothiazol-2-yloxy)-phenyl]-4-trifluoromethyl-benzenesulfonamide (293). $^1$H NMR (400 MHz, DMSO-$d_6$) δ 11.53 (s, 1H), 8.29 (d, J=8.3 Hz, 1H), 8.18 (d, J=1.0 Hz, 1H), 7.89 (dd, J=8.3, 1.2 Hz, 1H), 7.74 (dd, J=7.0, 2.3 Hz, 1H), 7.37 (t, J=2.0 Hz, 1H), 7.30-7.24 (m, 2H), 7.21 (t, J=2.0 Hz, 1H), 7.11 (t, J=1.9 Hz, 1H), 2.44 (s, 3H). MS (EI): m/z 531 (M–H).

Example 294

2,4-Dichloro-N-[3-chloro-5-(4-methyl-benzothiazol-2-yloxy)-phenyl]-benzenesulfonamide (294). $^1$H NMR (400 MHz, DMSO-$d_6$) δ 11.37 (s, 1H), 8.07 (d, J=8.6 Hz, 1H), 7.92 (d, J=2.0 Hz, 1H), 7.76 (dd, J=7.0, 2.2 Hz, 1H), 7.57 (dd, J=8.6, 2.0 Hz, 1H), 7.35 (t, J=2.0 Hz, 1H), 7.31-7.24 (m, 2H), 7.16 (t, J=2.0 Hz, 1H), 7.08 (t, J=1.9 Hz, 1H), 2.46 (s, 3H). MS (EI): m/z 497 (M–H).

Example 295

2,4-Dichloro-N-[3-chloro-5-(4-methyl-benzothiazol-2-yloxy)-phenyl]-5-methyl-benzenesulfonamide (295). $^1$H NMR (400 MHz, DMSO-$d_6$) δ 11.34 (s, 1H), 8.08 (s, 1H), 7.84 (s, 1H), 7.74 (dd, J=7.1, 2.1 Hz, 1H), 7.32 (t, J=2.0 Hz, 1H), 7.30-7.24 (m, 2H), 7.16 (t, J=2.0 Hz, 1H), 7.09 (t, J=1.9 Hz, 1H), 2.44 (s, 3H), 2.17 (s, 3H). MS (EI): m/z 511 (M–H).

Example 296

2-Chloro-N-[3-chloro-5-(4-methoxy-benzothiazol-2-yloxy)-phenyl]-4-trifluoromethyl-benzenesulfonamide (296). $^1$H NMR (400 MHz, DMSO-$d_6$) δ 11.53 (s, 1H), 8.33 (d, J=8.2 Hz, 1H), 8.18 (s, 1H), 7.89 (d, J=8.2 Hz, 1H), 7.50 (d, J=8.1 Hz, 1H), 7.35-7.30 (m, 2H), 7.11 (t, J=2.0 Hz, 1H), 7.08 (t, J=1.8 Hz, 1H), 7.04 (d, J=8.0 Hz, 1H), 3.86 (s, 3H). MS (EI): m/z 547 (M–H).

Example 297

2,4-Dichloro-N-[3-chloro-5-(4-methoxy-benzothiazol-2-yloxy)-phenyl]-benzenesulfonamide (297). $^1$H NMR (400 MHz, DMSO-$d_6$) δ 11.38 (s, 1H), 8.11 (d, J=8.6 Hz, 1H), 7.92 (d, J=2.0 Hz, 1H), 7.57 (dd, J=8.6, 2.0 Hz, 1H), 7.52 (d, J=8.0 Hz, 1H), 7.33 (t, J=8.0 Hz, 1H), 7.31 (t, J=2.0 Hz, 1H), 7.08 (t, J=1.9 Hz, 1H), 7.08-7.03 (m, 2H), 3.87 (s, 3H). MS (EI): m/z 513 (M–H).

Example 298

2,4-Dichloro-N-[3-chloro-5-(4-methoxy-benzothiazol-2-yloxy)-phenyl]-5-methyl-benzenesulfonamide (298). $^1$H NMR (400 MHz, DMSO-$d_6$) δ 11.33 (s, 1H), 8.12 (s, 1H), 7.85 (s, 1H), 7.50 (dd, J=8.0 Hz, 1H), 7.32 (t, J=8.1 Hz, 1H), 7.30 (t, J=2.0 Hz, 1H), 7.10 (t, J=2.0 Hz, 1H), 7.07 (t, J=1.8 Hz, 1H), 7.04 (t, J=8.0 Hz, 1H), 3.86 (s, 3H), 2.21 (s, 3H). MS (EI): m/z 527 (M–H).

Example 299

2-Chloro-N-[3-chloro-5-(6-methyl-benzothiazol-2-yloxy)-phenyl]-4-trifluoromethyl-benzenesulfonamide (299). 1H NMR (400 MHz, DMSO-$d_6$) δ 11.53 (s, 1H), 8.30 (d, J=8.2 Hz, 1H), 8.19 (d, J=1.2 Hz, 1H), 7.90 (dd, J=8.4, 1.4 Hz, 1H), 7.74 (br s, 1H), 7.56 (d, J=8.2 Hz, 1H), 7.34 (t, J=2.0 Hz, 1H), 7.27 (dd, J=8.3, 1.5 Hz, 1H), 7.11 (t, J=2.0 Hz, 1H), 7.09 (t, J=1.9 Hz, 1H), 2.40 (s, 3H). MS (EI): m/z 531 (M–H).

Example 300

2,4-Dichloro-N-[3-chloro-5-(6-methyl-benzothiazol-2-yloxy)-phenyl]-benzenesulfonamide (300). $^1$H NMR (400 MHz, DMSO 6) δ 11.37 (s, 1H), 8.08 (d, J=8.6 Hz, 1H), 7.93 (d, J=2.0 Hz, 1H), 7.76 (br s, 1H), 7.58 (dd, J=8.6, 2.1 Hz, 1H), 7.57 (d, J=8.3 Hz, 1H), 7.32 (t, J=1.9 Hz, 1H), 7.28 (dd, J=8.3, 1.5 Hz, 1H), 7.09-7.05 (m, 2H), 2.40 (s, 3H). MS (EI): m/z 497 (M–H).

Example 301

2,4-Dichloro-N-[3-chloro-5-(6-methyl-benzothiazol-2-yloxy)-phenyl]-5-methyl-benzenesulfonamide (301). $^1$H NMR (400 MHz, DMSO-$d_6$) δ 11.33 (s, 1H), 8.09 (s, 1H), 7.86 (s, 1H), 7.74 (br s, Hz, 1H), 7.54 (d, J=8.2 Hz, 1H), 7.31 (t, J=2.0 Hz, 1H), 7.26 (dd, J=8.4, 1.3 Hz, 1H), 7.09-7.05 (m, 2H), 2.40 (s, 3H), 2.20 (s, 3H). MS (EI): m/z 511 (M–H).

Example 302

2-Chloro-N-[3-chloro-5-(6-chloro-benzothiazol-2-yloxy)-phenyl]-4-trifluoromethyl-benzenesulfonamide (302). $^1$H NMR (400 MHz, DMSO-$d_6$) δ 11.56 (s, 1H), 8.31 (d, J=8.2 Hz, 1H), 8.18 (d, J=1.1 Hz, 1H), 8.12 (d, J=2.2 Hz, 1H), 7.91 (dd, J=8.3, 1.2 Hz, 1H), 7.68 (d, J=8.6 Hz, 1H), 7.48 (dd, J=8.6, 2.2 Hz, 1H), 7.38 (t, J=1.9 Hz, 1H), 7.13 (t, J=2.0 Hz, 1H), 7.10 (t, J=1.9 Hz, 1H). MS (EI): m/z 551 (M–H).

Example 303

2,4-Dichloro-N-[3-chloro-5-(6-chloro-benzothiazol-2-yloxy)-phenyl]-benzenesulfonamide (303). $^1$H NMR (400 MHz, DMSO-$d_6$) δ 11.39 (s, 1H), 8.13 (d, J=2.1 Hz, 1H), 8.10 (d, J=8.6 Hz, 1H), 7.93 (d, J=2.0 Hz, 1H), 7.69 (d, J=8.7 Hz, 1H), 7.60 (dd, J=8.5, 2.0 Hz, 1H), 7.49 (dd, J=8.6, 2.2 Hz, 1H), 7.36 (t, J=1.6 Hz, 1H), 7.10-7.06 (m, 2H). MS (EI): m/z 517 (M–H).

Example 304

2-Chloro-N-[3-chloro-5-(6-fluoro-benzothiazol-2-yloxy)-phenyl]-4-trifluoromethyl-benzenesulfonamide (304). $^1$H NMR (400 MHz, DMSO-$d_6$) δ 11.54 (s, 1H), 8.31 (d, J=8.3 Hz, 1H), 8.19 (br s, 1H), 7.93-7.88 (m, 2H), 7.70 (dd, J=8.9, 4.9 Hz, 1H), 7.37 (br s, 1H), 7.31 (td, J=9.1, 2.7 Hz, 1H), 7.11 (t, J=2.0 Hz, 1H), 7.09 (t, J=1.9 Hz, 1H). MS (EI): m/z 535 (M−H).

Example 305

2,4-Dichloro-N-[3-chloro-5-(6-fluoro-benzothiazol-2-yloxy)-phenyl]-benzenesulfonamide (305). $^1$H NMR (400 MHz, DMSO-$d_6$) δ 11.38 (s, 1H), 8.09 (d, J=8.6 Hz, 1H), 7.93 (d, J=1.9 Hz, 1H), 7.91 (dd, J=8.8, 2.7 Hz, 1H), 7.71 (dd, J=8.9, 4.9 Hz, 1H), 7.59 (dd, J=8.6, 2.1 Hz, 1H), 7.35 (t, J=2.0 Hz, 1H), 7.32 (td, J=9.2, 2.7 Hz, 1H), 7.10-7.06 (m, 2H). MS (EI): m/z 501 (M−H).

Example 306

2,4-Dichloro-N-[3-chloro-5-(6-fluoro-benzothiazol-2-yloxy)-phenyl]-5-methyl-benzenesulfonamide (306). $^1$H NMR (400 MHz, DMSO-$d_6$) δ 11.34 (s, 1H), 8.10 (s, 1H), 7.90 (dd, J=8.7, 2.7 Hz, 1H), 7.86 (s, 1H), 7.68 (dd, J=8.9, 4.9 Hz, 1H), 7.35-7.29 (m, 2H), 7.09-7.07 (m, 2H), 2.21 (s, 3H). MS (EI): m/z 515 (M−H).

Example 307

2-Chloro-N-[3-chloro-5-(6-methoxy-benzothiazol-2-yloxy)-phenyl]-4-trifluoromethyl-benzenesulfonamide (307). $^1$H NMR (400 MHz, DMSO-$d_6$) δ 11.52 (s, 1H), 8.29 (d, J=8.2 Hz, 1H), 8.18 (br s, 1H), 7.90 (dd, J=8.4, 1.3 Hz, 1H), 7.58 (d, J=8.9 Hz, 1H), 7.57 (d, J=2.7 Hz, 1H), 7.33 (t, J=1.9 Hz, 1H), 7.10 (t, J=2.0 Hz, 1H), 7.08 (t, J=1.9 Hz, 1H), 7.04 (dd, J=8.9, 2.7 Hz, 1H), 3.80 (s, 3H). MS (EI): m/z 547 (M−H).

Example 308

2,4-Dichloro-N-[3-chloro-5-(6-methoxy-benzothiazol-2-yloxy)-phenyl]-benzenesulfonamide (308). $^1$H NMR (400 MHz, DMSO-$d_6$) δ 11.36 (s, 1H), 8.08 (d, J=58.6 Hz, 1H), 7.93 (d, J=2.0 Hz, 1H), 7.62-7.57 (m, 3H), 7.30 (t, J=2.0 Hz, 1H), 7.07-7.03 (m, 3H), 3.80 (s, 3H). MS (EI): m/z 513 (M−H).

Example 309

2,4-Dichloro-N-[3-chloro-5-(6-methoxy-benzothiazol-2-yloxy)-phenyl]-5-methyl-benzenesulfonamide (309). $^1$H NMR (400 MHz, DMSO-$d_6$) δ 11.32 (s, 1H), 8.09 (s, 1H), 7.86 (s, 1H), 7.58-7.55 (m, 2H), 7.29 (t, J=2.0 Hz, 1H), 7.08-7.03 (m, 3H), 3.80 (s, 3H), 2.21 (s, 3H). MS (EI): m/z 529 (M+H).

Example 310

2-[3-Chloro-5-(2-chloro-4-trifluoromethyl-benzenesulfonylamino)-phenoxy]-benzothiazole-6-carboxylic acid ethyl ester (310). $^1$H NMR (400 MHz, DMSO-$d_6$) δ 11.56 (s, 1H), 8.63 (d, J=1.5 Hz, 1H), 8.32 (d, J=8.2 Hz, 1H), 8.18 (s, 1H), 8.00 (dd, J=8.5, 1.7 Hz, 1H), 7.91 (d, J=8.3 Hz, 1H), 7.75 (d, J=8.5 Hz, 1H), 7.40 (t, J=1.9 Hz, 1H), 7.16 (t, J=1.9 Hz, 1H), 7.12 (t, J=1.8 Hz, 1H), 4.33 (q, J=7.1 Hz, 1H), 1.34 (t, J=7.1 Hz, 1H). MS (EI): m/z 589 (M−H).

Example 311

2-[3-Chloro-5-(2-chloro-4-trifluoromethyl-benzenesulfonylamino)-phenoxy]-benzothiazole-6-carboxylic acid ethyl ester (311). $^1$H NMR (400 MHz, DMSO-$d_6$) δ 11.41 (s, 1H), 8.65 (d, J=1.2 Hz, 1H), 8.11 (d, J=8.5 Hz, 1H), 8.01 (dd, J=8.5, 1.5 Hz, 1H), 7.93 (d, J=2.0 Hz, 1H), 7.76 (d, J=8.5 Hz, 1H), 7.59 (dd, J=8.5, 2.0 Hz, 1H), 7.39 (br s, 1H), 7.12 (br s, 1H), 7.10 (br s, 1H), 4.34 (q, J=7.1 Hz, 1H), 1.34 (t, J=7.1 Hz, 1H). MS (EI): m/z 555 (M−H).

Example 312

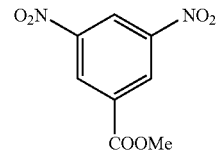

3,5-Dinitro-benzoic acid methyl ester (312). To 3,5-Dinitro-benzoic acid (Aldrich, 21.2 g, 100 mmol) was added $SOCl_2$. The mixture was refluxed overnight. The excess $SOCl_2$ was removed under reduced pressure. The residue was dissolved in 100 mL of MeOH, cooled in ice bath, and triethylamine (Aldrich, 21 mL, 150 mmol) was added slowly added. After the mixture was stirred at ambient temperature for 3 h, solvent was removed under reduced pressure. The residue was diluted with EtOAc and 1N HCl. The mixture was extracted 3× with EtOAc (100 mL). The organic layers were washed twice with a brine solution (100 mL), dried over $Na_2SO_4$. Removal of the solvent gave 22.0 g (97%) of product, which was pure enough for the next reaction. $^1$H NMR (400 MHz, DMSO-$d_6$) δ 9.05 (t, J=2.1 Hz, 1H), 8.92 (d, J=2.1 Hz, 2H), 3.99 (s, 3H).

Example 313

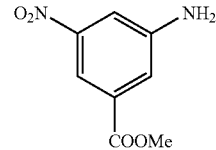

3-Amino-5-nitro-benzoic acid methyl ester (313). 3,5-Dinitro-benzoic acid methyl ester (Example 312, 13.7 g, 60.6 mmol), Pd/C (Aldrich, 1.34 g, 10%, 0.61 mmol), triethylamine (Aldrich, 36.4 mL, 273 mmol) was dissolved in 30 mL of $CH_3CN$. To the above solution was added a solution of HCOOH (Aldrich, 9.7 mL, 261 mmol) in 30 mL of $CH_3CN$ dropwise. The mixture was then refluxed for 2 h. After cooled to room temperature, the mixture was filtered through a Celite pad, washed with EtOAc, and the filtrate was concentrated. The residue was purified by chromatography (5%-10% EtOAc/$CH_2Cl_2$) to give 7.0 g (59%) of product. $^1$H NMR (400 MHz, DMSO-$d_6$) δ 7.74 (t, J=2.0 Hz, 1H), 7.59 (t, J=2.2 Hz, 1H), 7.55 (t, J=2.0 Hz, 1H), 6.16 (s, 2H), 3.87 (s, 3H).

Example 314

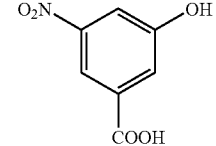

3-Hydroxy-5-nitro-benzoic acid (314). To a solution of 3-amino-5-nitro-benzoic acid methyl ester (Example 313, 1.96 g, 10 mmol) in 23 mL of H$_2$O and 5 mL of con. H$_2$SO$_4$ at 0° C., was added a solution of NaNO$_2$ (Aldrich, 900 mg, 13 mmol) in 9 mL of H$_2$O. After 50 min stirring, the resulting diazonium salt was added to a solution of 17 mL of H$_2$O and 17 mL of con. H$_2$SO$_4$ at 90° C. After stirred at 90° C. for 90 min, the mixture was cooled to room temperature and brought to pH 3 with con. NH$_4$OH. The mixture was extracted 3× with EtOAc (100 mL). The organic layers were washed twice with a brine solution (100 mL), dried over Na$_2$SO$_4$ and concentrated. The residue was purified by chromatography (5%-10% MeOH/CH$_2$Cl$_2$) to give 705 mg (39%) of product. $^1$H NMR (400 MHz, DMSO-d$_6$) δ 13.64 (br s, 1H), 10.84 (s, 1H), 8.08 (t, J=1.8 Hz, 1H), 7.75 (t, J=2.2 Hz, 1H), 7.70 (dd, J=2.2, 1.3 Hz, 1H), 6.16 (s, 2H), 3.87 (s, 3H). MS (EI): m/z 184 (M+H).

Example 315

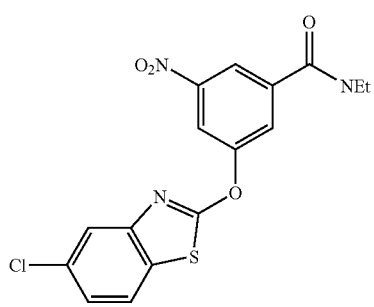

3-(5-Chloro-benzothiazol-2-yloxy)-N-ethyl-5-nitro-benzamide (315). To a solution of 3-hydroxy-5-nitro-benzoic acid (Example 314, 705 mg, 3.85 mmol) in DMF was added NaH (Aldrich, 340 mg, 60%, 8.5 mmol). The mixture was stirred for 10 min, then 2,5-dichlorobenzothiazole (Example 253, 782 mg, 3.85 mmol) was added. The mixture was heated at 60° C. till there is no starting material remained by TLC. After cooled to room temperature, the mixture was poured to ice/1N HCl, and filtered. The precipitate was triturated with CH$_2$Cl$_2$/hexanes to give 990 mg (74%) of product. $^1$H NMR (400 MHz, DMSO-d$_6$) δ 8.67 (t, J=1.8 Hz, 1H), 8.57 (t, J=2.0 Hz, 1H), 8.41 (dd, J=2.2, 1.4 Hz, 1H), 8.06 (d, J=8.6 Hz, 1H), 7.82 (d, J=2.1 Hz, 1H), 7.44 (dd, J=8.6, 2.1 Hz, 1H). MS (EI): m/z 351 (M+H). To a solution of the above product in THF was added HOAT (385 mg, 2.83 mmol), HBTU (1.07 g, 2.83 mmol), N-methylmorpholine (Aldrich, 0.8 mL, 7.1 mmol) followed by ethylamine (Aldrich, 1.7 mL, 2M solution in THF, 3.4 mmol). The mixture was stirred overnight. THF was removed under reduced pressure and the residue was diluted with EtOAc and 1N HCl. The mixture was extracted 3× with EtOAc (500 mL). The organic layers were washed twice with a brine solution (50 mL), dried over Na$_2$SO$_4$ and concentrated. The residue was purified by chromatography (15% EtOAc/CH$_2$Cl$_2$) to give 625 mg (56%) of product. $^1$H NMR (400 MHz, DMSO-d$_6$) δ 8.93 (br t, J=5.3 Hz, 1H), 8.68 (t, J=1.8 Hz, 1H), 8.59 (t, J=2.0 Hz, 1H), 8.38 (t, J=1.9 Hz, 1H), 8.06 (d, J=8.6 Hz, 1H), 7.84 (d, J=2.1 Hz, 1H), 7.44 (dd, J=8.6, 2.1 Hz, 1H), 3.33 (m, 2H), 1.15 (t, J=7.2 Hz, 1H). MS (EI): m/z 378 (M+H).

Example 316

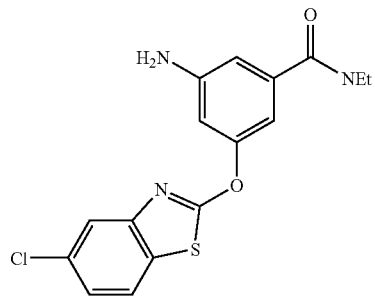

3-Amino-5-(5-chloro-benzothiazol-2-yloxy)-N-ethyl-benzamide (316). 3-Amino-5-(5-chloro-benzothiazol-2-yloxy)-N-ethyl-benzamide (316) was synthesized from 3-(5-chloro-benzothiazol-2-yloxy)-N-ethyl-5-nitro-benzamide (315, 620 mg, 1.64 mmol) in a similar manner as described in Examples 16-23 (Method A). $^1$H NMR (400 MHz, DMSO-d$_6$) δ 8.33 (br t, J=5.5 Hz, 1H), 7.98 (d, J=8.6 Hz, 1H), 7.82 (d, J=2.1 Hz, 1H), 7.39 (dd, J=8.6, 2.1 Hz, 1H), 7.05 (t, J=1.8 Hz, 1H), 6.95 (t, J=1.8 Hz, 1H), 6.66 (t, J=1.9 Hz, 1H), 3.23 (m, 2H), 1.08 (t, J=7.2 Hz, 1H). MS (EI): m/z 378 (M+H).

Example 317

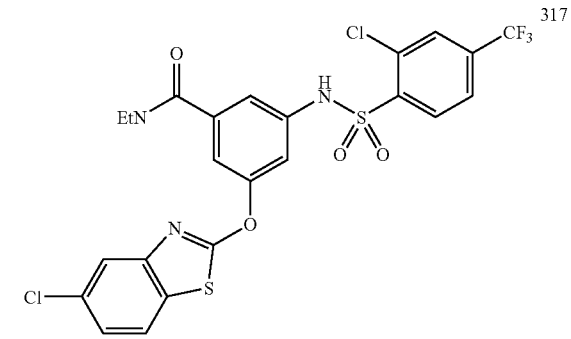

3-(5-Chloro-benzothiazol-2-yloxy)-5-(2-chloro-4-trifluoromethylbenzenesulfonylamino)-N-ethyl-benzamide (317). 3-(5-Chloro-benzothiazol-2-yloxy)-5-(2-chloro-4-trifluoromethylbenzenesulfonylamino)-N-ethyl-benzamide (317) was synthesized (71%) from 3-amino-5-(5-chloro-benzothiazol-2-yloxy)-N-ethyl-benzamide (316) in a similar manner as described in Examples 70-91. $^1$H NMR (400 MHz, DMSO-d$_6$) δ 11.41 (s, 1H), 8.51 (br t, J=5.4 Hz, 1H), 8.28 (d, J=8.3 Hz, 1H), 8.17 (s, 1H), 7.99 (d, J=8.6 Hz, 1H), 7.91 (d, J=8.3 Hz, 1H), 7.76 (d, J=2.1 Hz, 1H), 7.60 (m, 2H), 7.42 (dd, J=8.6, 2.1 Hz, 1H), 7.29 (t, J=1.9 Hz, 1H), 3.23 (m, 2H), 1.07 (t, J=7.2 Hz, 1H). MS (EI): m/z 590 (M+H).

Example 318

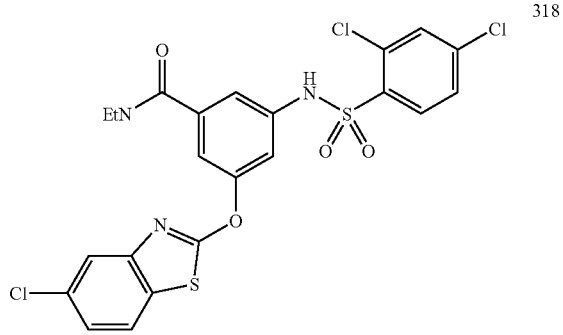

3-(5-Chloro-benzothiazol-2-yloxy)-5-(2,4-dichloro-benzenesulfonylamino)-N-ethyl-benzamide (318). 3-(5-Chloro-benzothiazol-2-yloxy)-5-(2,4-dichloro-benzenesulfonylamino)-N-ethyl-benzamide (318) was synthesized (83%) from 3-amino-5-(5-chloro-benzothiazol-2-yloxy)-N-ethyl-benzamide (316) in a similar manner as described in Examples 70-91. $^1$H NMR (400 MHz, DMSO-$d_6$) δ 11.26 (s, 1H), 8.51 (br t, J=5.5 Hz, 1H), 8.06 (d, J=8.6 Hz, 1H), 8.01 (d, J=8.6 Hz, 1H), 7.91 (d, J=2.1 Hz, 1H), 7.77 (d, J=2.0 Hz, 1H), 7.60-7.56 (m, 3H), 7.43 (dd, J=8.6, 2.1 Hz, 1H), 7.25 (t, J=2.1 Hz, 1H), 3.23 (m, 2H), 1.07 (t, J=7.2 Hz, 1H). MS (EI): m/z 554 (M−H).

Example 319

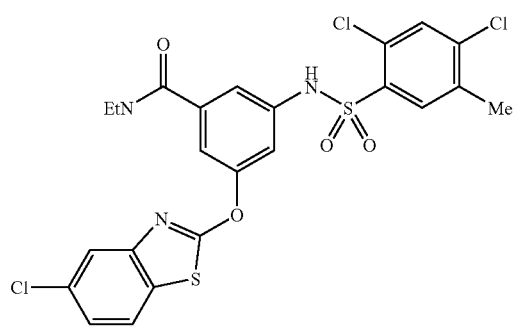

319

3-(5-Chloro-benzothiazol-2-yloxy)-5-(2,4-dichloro-5-methyl-benzenesulfonylamino)-N-ethyl-benzamide (319). 3-(5-Chloro-benzothiazol-2-yloxy)-5-(2,4-dichloro-5-methyl-benzenesulfonylamino)-N-ethyl-benzamide (319) was synthesized (81%) from 3-amino-5-(5-chloro-benzothiazol-2-yloxy)-N-ethyl-benzamide (316) in a similar manner as described in Examples 70-91. $^1$H NMR (400 MHz, DMSO-$d_6$) δ 11.24 (s, 1H), 8.50 (br t, J=5.3 Hz, 1H), 8.08 (s, 1H), 7.99 (d, J=8.6 Hz, 1H), 7.85 (s, 1H), 7.73 (d, J=2.1 Hz, 1H), 7.58-7.55 (m, 2H), 7.43 (dd, J=8.6, 2.1 Hz, 1H), 7.26 (t, J=2.1 Hz, 1H), 3.23 (m, 2H), 2.19 (s, 3H), 1.07 (t, J=7.2 Hz, 1H). MS (EI): m/z 570 (M+H).

Example 320

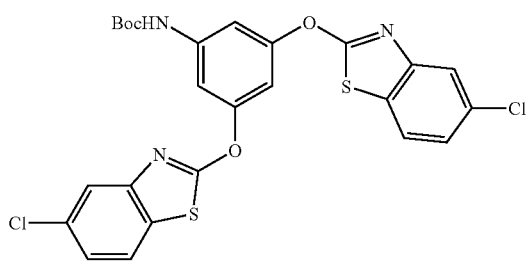

320

[3,5-Bis-(5-chloro-benzothiazol-2-yloxy)-phenyl]-carbamic acid tert-butyl ester (320). [3,5-Bis-(5-chloro-benzothiazol-2-yloxy)-phenyl]-carbamic acid tert-butyl ester (320) was synthesized (57%) from 3,5-dihydroxy-benzoic acid (Aldrich, 770 mg, 5 mmol) and 2,5-dichlorobenzothiazole (253, 2.03 g, 10 mmol) in a similar manner as described in Example 263. $^1$H NMR (400 MHz, DMSO-$d_6$) δ 9.91 (br s, 1H), 8.02 (d, J=8.6 Hz, 2H), 7.84 (d, J=2.1 Hz, 2H), 7.54-7.51 (m, 2H), 7.42 (dd, J=8.6, 2.1 Hz, 2H), 7.34 (t, J=2.2 Hz, 1H), 1.47 (s, 9H). MS (EI): m/z 560 (M+H).

Example 321

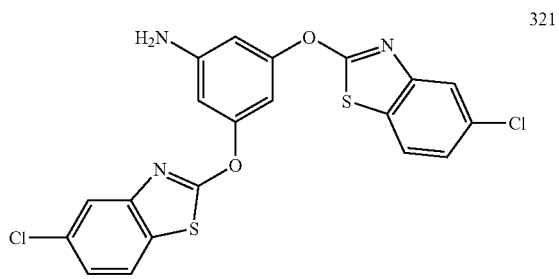

321

3,5-Bis-(5-chloro-benzothiazol-2-yloxy)-phenylamine (321). 3,5-Bis-(5-chloro-benzothiazol-2-yloxy)-phenylamine (321) was synthesized (94%) from [3,5-Bis-(5-chloro-benzothiazol-2-yloxy)-phenyl]-carbamic acid tert-butyl ester (320) in a similar manner as described in Example 273. $^1$H NMR (400 MHz, DMSO-$d_6$) δ 7.99 (d, J=8.6 Hz, 2H), 7.83 (d, J=2.0 Hz, 2H), 7.40 (dd, J=8.6, 2.1 Hz, 2H), 6.70 (t, J=2.2 Hz, 1H), 6.58-6.55 (m, 2H), 5.89 (s, 2H). MS (EI): m/z 460 (M+H).

Example 322

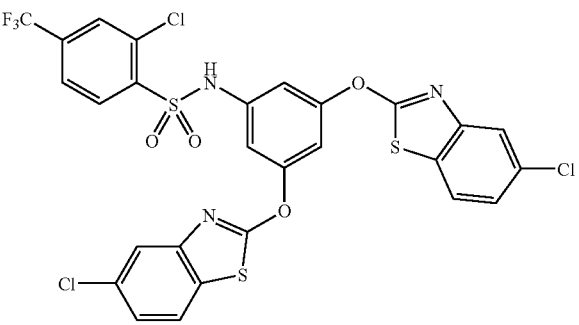

322

N-[3,5-Bis-(5-chloro-benzothiazol-2-yloxy)-phenyl]-2-chloro-4-trifluoromethyl-benzenesulfonamide (322). N-[3,5-Bis-(5-chloro-benzothiazol-2-yloxy)-phenyl]-2-chloro-4-trifluoromethyl-benzenesulfonamide (322) was synthesized (58%) from 3,5-bis-(5-chloro-benzothiazol-2-yloxy)-phenylamine (321) in a similar manner as described in Examples 70-91. $^1$H NMR (400 MHz, DMSO-$d_6$) δ 11.57 (br s, 1H), 8.32 (d, J=8.2 Hz, 1H), 8.20 (s, 1H), 8.01 (d, J=8.6 Hz, 2H), 7.87 (d, J=8.3 Hz, 1H), 7.78 (d, J=2.0 Hz, 2H), 7.45-7.41 (m, 3H), 7.15-7.14 (m, 2H). MS (EI): m/z 700 (M−H).

Example 323

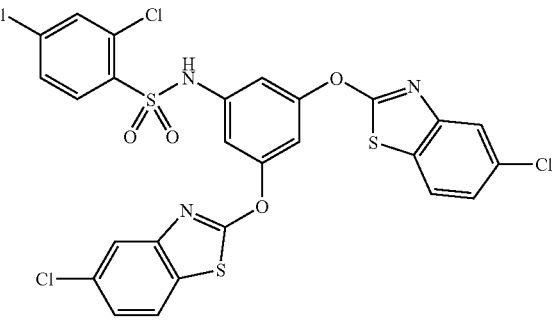

323

N-[3,5-Bis-(5-chloro-benzothiazol-2-yloxy)-phenyl]-2,4-dichloro-benzenesulfonamide (323). N-[3,5-Bis-(5-chloro-benzothiazol-2-yloxy)-phenyl]-2,4-dichloro-benzenesulfonamide (323) was synthesized (57%) from 3,5-bis-(5-chloro-benzothiazol-2-yloxy)-phenylamine (321) in a similar manner as described in Examples 70-91. $^{1}$H NMR (400 MHz, DMSO-$d_6$) δ 11.42 (br s, 1H), 8.11 (d, J=8.6 Hz, 1H), 8.02 (d, J=8.6 Hz, 2H), 7.95 (d, J=2.0 Hz, 1H), 7.79 (d, J=2.0 Hz, 2H), 7.53 (d, J=8.6, 1.9 Hz, 1H), 7.45-7.41 (m, 3H), 7.12-7.09 (m, 2H). MS (EI): m/z 666 (M–H).

Example 324

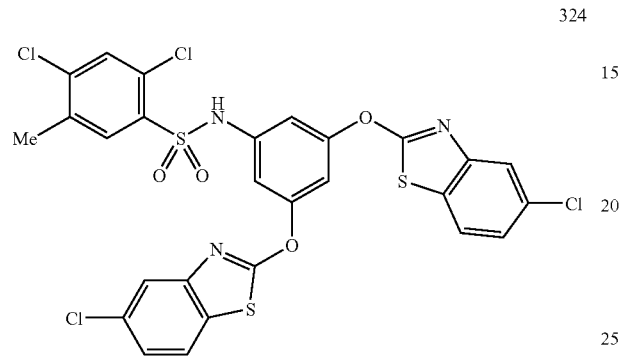

N-[3,5-Bis-(5-chloro-benzothiazol-2-yloxy)-phenyl]-2,4-dichloro-5-methyl-benzenesulfonamide (324). N-[3,5-Bis-(5-chloro-benzothiazol-2-yloxy)-phenyl]-2,4-dichloro-5-methyl-benzenesulfonamide (324) was synthesized (70%) from 3,5-bis-(5-chloro-benzothiazol-2-yloxy)-phenylamine (321) in a similar manner as described in Examples 70-91. $^{1}$H NMR (400 MHz, DMSO-$d_6$) δ 11.40 (br s, 1H), 8.11 (s, 1H), 8.01 (d, J=8.6 Hz, 2H), 7.88 (s, 1H), 7.76 (d, J=2.0 Hz, 2H), 7.43 (dd, J=8.6, 1.9 Hz, 1H), 7.39 (t, J=1.8 Hz, 2H), 7.12-7.09 (m, 2H), 2.09 (s, 3H). MS (EI): m/z 680 (M–H).

Example 325

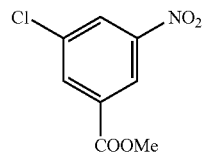

3-Chloro-5-nitro-benzoic acid methyl ester (325). 3-Chloro-5-nitro-benzoic acid methyl ester (325) was synthesized (85%) from 3-amino-5-nitro-benzoic acid methyl ester (313) in a similar manner as described in Example 255. $^{1}$H NMR (400 MHz, DMSO-$d_6$) δ 8.57 (t, J=2.1 Hz, 1H), 8.53 (dd, J=2.1, 1.4 Hz, 1H), 8.33 (dd, J=1.8, 1.6 Hz, 1H), 3.94 (s, 3H).

Example 326

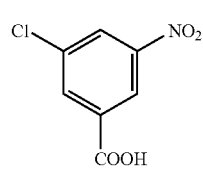

3-Chloro-5-nitro-benzoic acid (326). To a solution of 3-chloro-5-nitro-benzoic acid methyl ester (325, 2.75 g, 12.76 mmol) in 60 mL of MeOH was added a solution of NaOH (EM, 5.10 g, 127.6 mmol) in 35 mL of H$_2$O. The mixture was stirred for 2 h. MeOH was removed under reduced pressure, and the mixture was diluted with water, brought to pH 2 with con. HCl. Filtration followed by washing with water gave 2.35 g (92%) desired product. $^{1}$H NMR (400 MHz, DMSO-$d_6$) δ 14.02 (s, 1H), 8.57-8.52 (m, 2H), 8.31 (dd, J=1.9, 1.2 Hz, 1H), 3.94 (s, 3H). MS (EI): m/z 200 (M–H).

Example 327

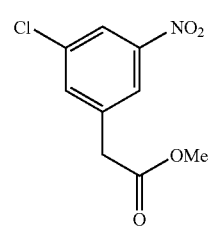

(3-Chloro-5-nitro-phenyl)-acetic acid methyl ester (327). To 3-Chloro-5-nitro-benzoic acid (326, 2.35 g, 11.7 mmol) was added SOCl$_2$. The mixture was refluxed overnight. The excess SOCl$_2$ was removed under reduced pressure to give the corresponding acid chloride. The above acid chloride was dissolved in 15 mL of CH$_3$CN, cooled to 0° C. A mixture of TMSCHN$_2$ (Aldrich, 11.7 mL, 2M, 23.4 mmol) and Et$_3$N, which was also cooled to 0° C., was added. The resulting mixture was stirred for 4 h. The solvent was removed under reduced pressure and the residue was diluted with EtOAc and 1N HCl. The mixture was extracted 3× with EtOAc (100 mL). The organic layers were washed twice with a brine solution (100 mL), dried over Na$_2$SO$_4$ and concentrated. The residue was purified by chromatography (20% EtOAc/hexanes) to give 2.1 g (79%) of product. $^{1}$H NMR (400 MHz, DMSO-$d_6$) δ 8.53-8.50 (m, 2H), 8.35 (t, J=1.7 Hz, 1H), 7.35 (s, 1H).

To a solution of the above product (2.1 g, 9.29 mmol) in 45 mL of MeOH at –25° C. was added a mixture of AgOBz (Aldrich, 213 mg, 0.93 mmol) and Et$_3$N (Aldrich, 3.9 mL, 27.9 mmol) dropwise. The resulting mixture was stirred till ambient temperature was reached. The solvent was removed under reduced pressure and the residue was diluted with EtOAc and 1N HCl. The mixture was extracted 3× with EtOAc (50 mL). The organic layers were washed twice with a brine solution (50 mL), dried over Na$_2$SO$_4$ and concentrated. The residue was purified by chromatography (20% EtOAc/hexanes) to give 925 mg (43%) of product. $^{1}$H NMR (400 MHz, CDCl$_3$) δ 8.15 (t, J=2.0 Hz, 1H), 8.07 (t, J=1.5 Hz, 1H), 7.63 (t, J=1.5 Hz, 1H), 3.74 (s, 2H), 3.73 (s, 3H).

Example 328

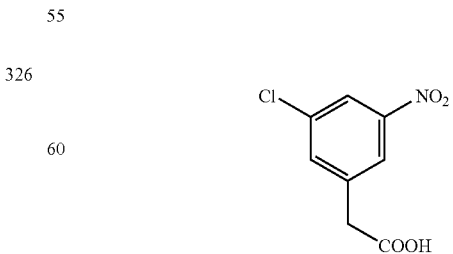

(3-Chloro-5-nitro-phenyl)-acetic acid (328). To a solution of (3-Chloro-5-nitro-phenyl)-acetic acid methyl ester (327, 920 mg, 4.0 mmol) in 20 mL of MeOH was added a solution of NaOH (EM, 1.6 g, 40 mmol) in 10 mL of H$_2$O. The mixture was stirred for 2 h. MeOH was removed under reduced pressure, and the mixture was diluted with water, brought to pH 2 with con. HCl. The mixture was extracted 3× with EtOAc (50 mL). The organic layers were washed twice with a brine solution (50 mL), dried over Na$_2$SO$_4$. Removal of the solvent gave 810 mg (94%) of product. $^1$H NMR (400 MHz, DMSO-d$_6$) δ 8.17-8.14 (m, 2H), 7.84 (br s, 1H), 3.77 (s, 3H).

Example 329

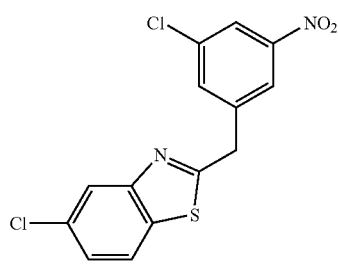

5-Chloro-2-(3-chloro-5-nitro-benzyl)-benzothiazole (329). 5-Chloro-2-(3-chloro-5-nitro-benzyl)-benzothiazole (329) was synthesized (92%) from (3-chloro-5-nitro-phenyl)-acetic acid (328, 430 mg, 2.0 mmol) and 2-amino-4-chloro-benzothiazole hydrochloride (6, 392 mg, 2.0 mmol) in a similar manner as described in Example 8. $^1$H NMR (400 MHz, DMSO-d$_6$) δ 8.30 (br s, 1H), 8.22 (t, J=2.0 Hz, 1H), 8.10 (d, J=8.6 Hz, 1H), 8.06 (d, J=2.0 Hz, 1H), 8.03 (br s, 1H), 7.47 (dd, J=8.6, 2.0 Hz, 1H), 4.72 (s, 2H). MS (EI): m/z 339 (M+H).

Example 330

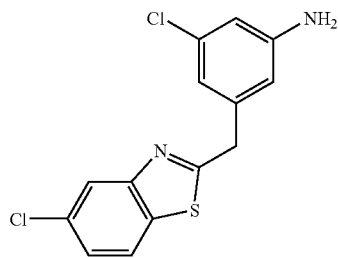

3-Chloro-5-(5-chloro-benzothiazol-2-ylmethyl)-phenylamine (330). 3-Chloro-5-(5-chloro-benzothiazol-2-ylmethyl)-phenylamine (330) was synthesized (95%) from 5-chloro-2-(3-chloro-5-nitro-benzyl)-benzothiazole (329) in a similar manner as described in Examples 16-23 (Method A). $^1$H NMR (400 MHz, DMSO-d$_6$) δ 8.07 (d, J=8.6 Hz, 1H), 8.046 (d, J=2.0 Hz, 1H), 7.46 (dd, J=8.6, 2.1 Hz, 1H), 6.53 (br s, 1H), 6.49 (t, J=1.9 Hz, 1H), 6.46 (br s, 1H), 4.30 (s, 2H). MS (EI): m/z 309 (M+H).

Example 331

2-Chloro-N-[3-chloro-5-(5-chloro-benzothiazol-2-ylmethyl)-phenyl]-4-trifluoromethyl-benzenesulfonamide (331). 2-Chloro-N-[3-chloro-5-(5-chloro-benzothiazol-2-ylmethyl)-phenyl]-4-trifluoromethyl-benzenesulfonamide (331) was synthesized (83%) from 3-Chloro-5-(5-chlorobenzothiazol-2-ylmethyl)-phenylamine (330) in a similar manner as described in Examples 70-91. $^1$H NMR (400 MHz, DMSO-d$_6$) δ 11.26 (br s, 1H), 8.19 (d, J=8.2 Hz, 1H), 8.08-8.03 (m, 3H), 7.69 (dd, J=8.3, 1.3 Hz, 1H), 7.49 (dd, J=8.6, 2.1 Hz, 1H), 7.19 (t, J=1.4 Hz, 1H), 7.09 (br s, 1H), 7.04 (t, J=1.9 Hz, 1H), 4.42 (s, 2H). MS (EI): m/z 549 (M−H).

Example 332

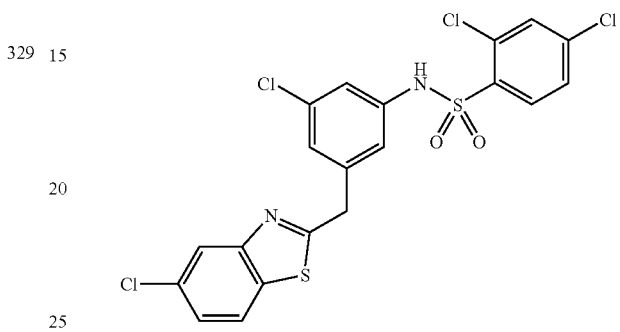

2,4-Dichloro-N-[3-chloro-5-(5-chloro-benzothiazol-2-ylmethyl)-phenyl]-benzenesulfonamide (332). 2,4-Dichloro-N-[3-chloro-5-(5-chloro-benzothiazol-2-ylmethyl)-phenyl]-benzenesulfonamide (332) was synthesized (78%) from 3-chloro-5-(5-chloro-benzothiazol-2-ylmethyl)-phenylamine (330) in a similar manner as described in Examples 70-91. $^1$H NMR (400 MHz, DMSO-d$_6$) δ 11.09 (br s, 1H), 8.09 (d, J=8.6 Hz, 1H), 8.05 (d, J=2.0 Hz, 1H), 7.95 (d, J=8.6 Hz, 1H), 7.79 (d, J=2.0 Hz, 1H), 7.50 (dd, J=8.6, 2.0 Hz, 1H), 7.34 (dd, J=8.6, 2.1 Hz, 1H), 7.17 (br s, 1H), 7.04-7.01 (m, 2H), 4.41 (s, 2H). MS (EI): m/z 515 (M−H).

Example 333

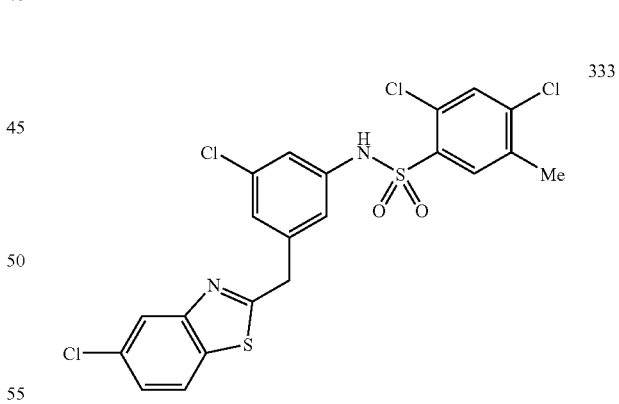

2,4-Dichloro-N-[3-chloro-5-(5-chloro-benzothiazol-2-ylmethyl)-phenyl]-5-methyl-benzenesulfonamide (333). 2,4-Dichloro-N-[3-chloro-5-(5-chloro-benzothiazol-2-ylmethyl)-phenyl]-5-methyl-benzenesulfonamide (333) was synthesized (83%) from 3-chloro-5-(5-chloro-benzothiazol-2-ylmethyl)-phenylamine (330) in a similar manner as described in Examples 70-91. $^1$H NMR (400 MHz, DMSO-d$_6$) δ 11.03 (br s, 1H), 8.05 (d, J=8.6 Hz, 1H), 8.02 (d, J=2.0 Hz, 1H), 8.01 (s, 1H), 7.76 (s, 1H), 7.48 (dd, J=8.6, 2.1 Hz, 1H), 7.17 (br s, 1H), 7.07 (br s, 1H), 7.04 (d, J=1.9 Hz, 1H), 4.42 (s, 2H), 2.19 (s, 3H). MS (EI): m/z 529 (M−H).

Example 334

Library compounds. To a solution of 3-chloro-5-(5-chloro-benzothiazol-2-yloxy)-phenylamine (273, 31 mg, 0.1 mmol) in 1 mL of pyridine was added the corresponding sulfonyl chloride. The mixture was stirred at 40° C. overnight. The pyridine was removed using Genevac vacuum system. The residue was purified by chromatography using a silica cartage (Varian, 2 g) and Vacmaster system, eluted with suitable solvent system (50%-80% CH$_2$Cl$_2$/hexanes or 5%-25% EtOAc/hexanes). The purity of the products was checked by HPLC and LCMS.

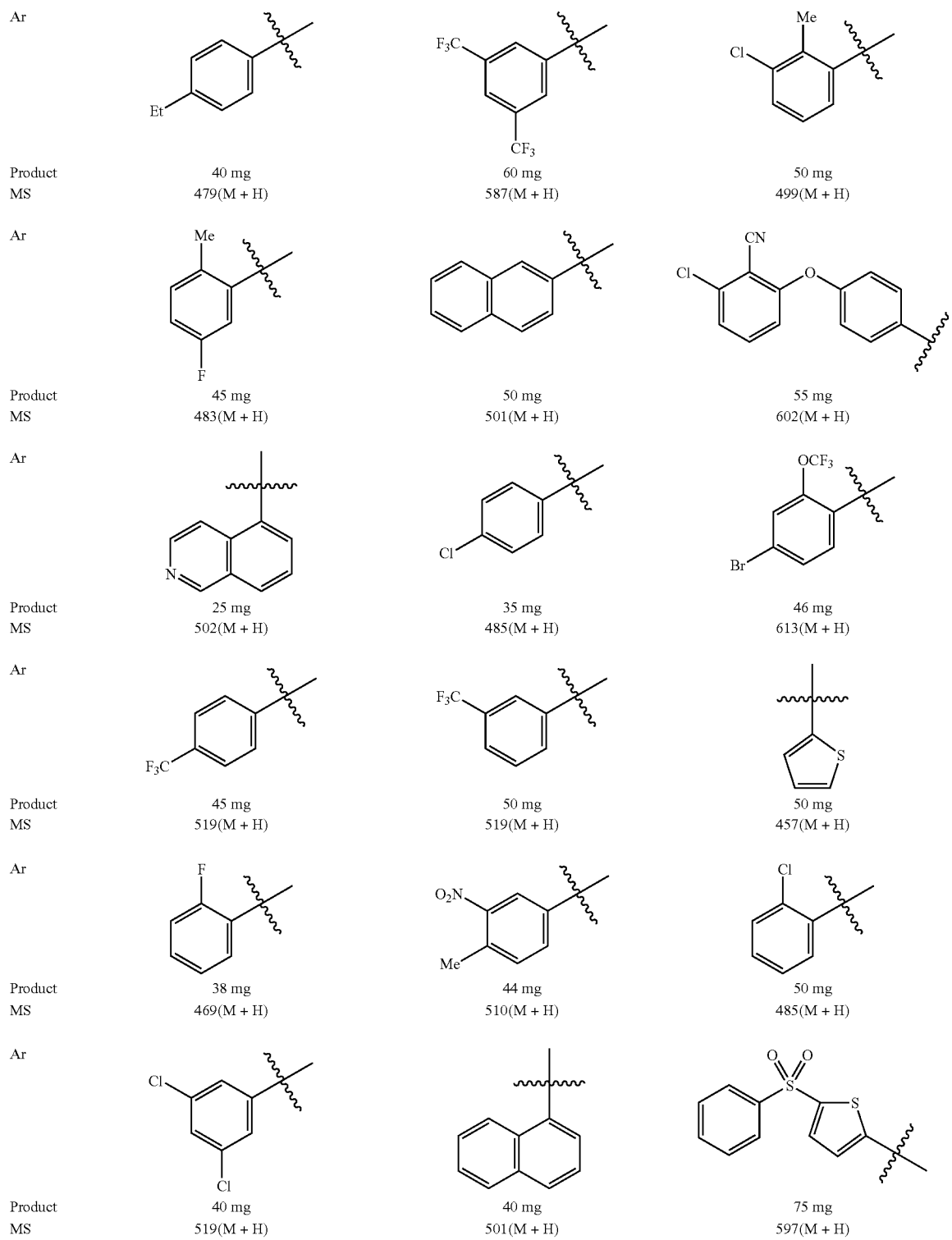

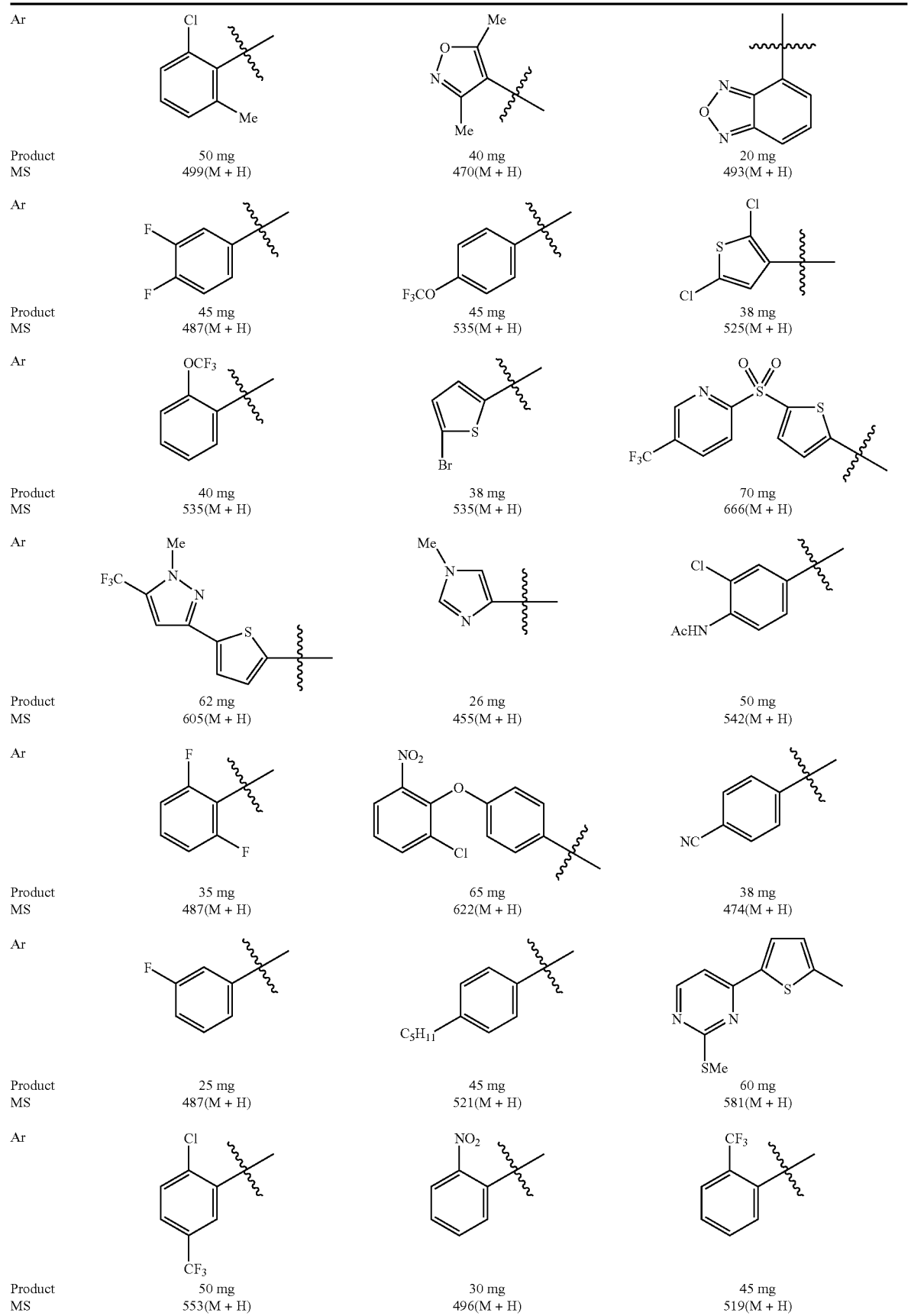

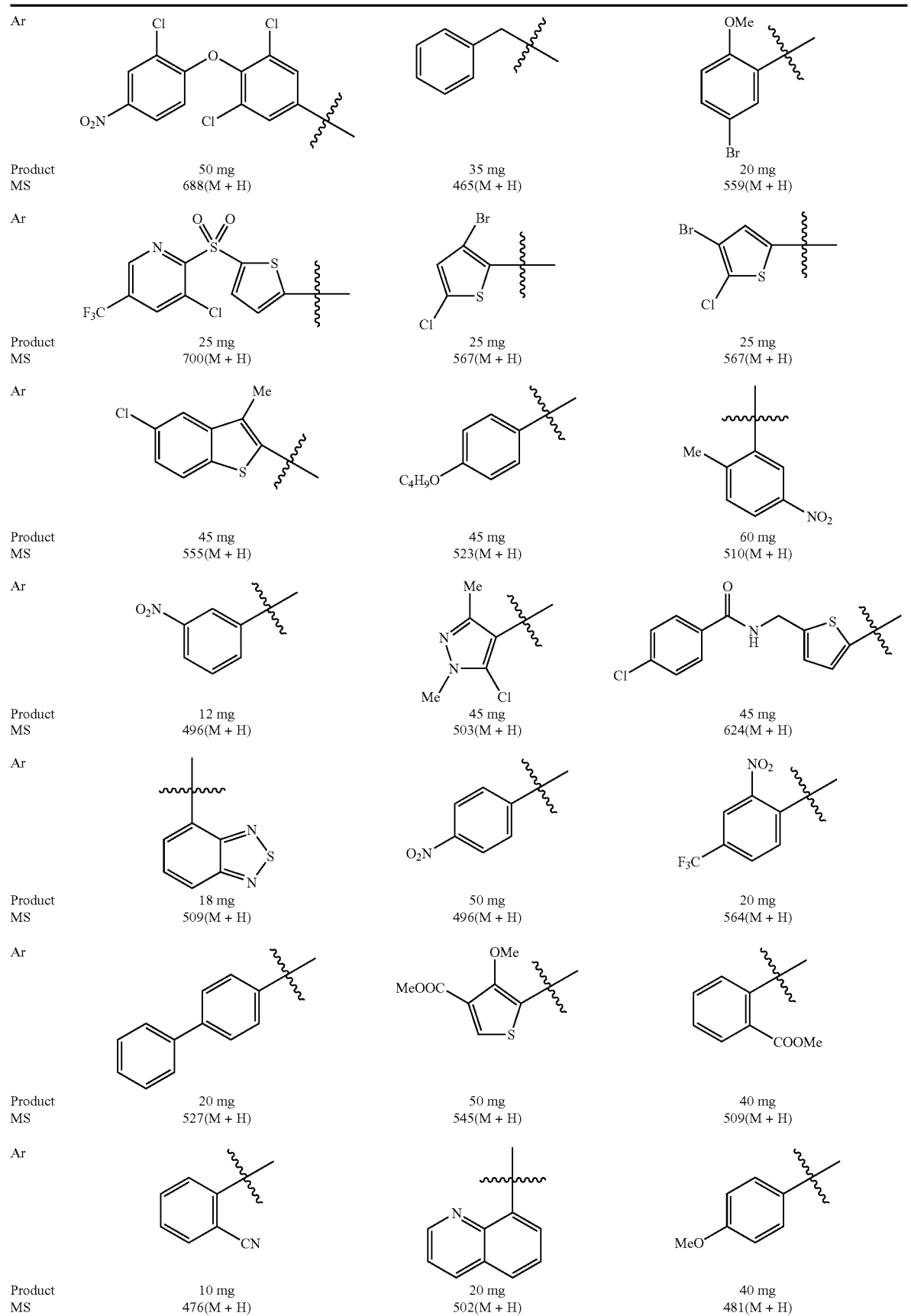

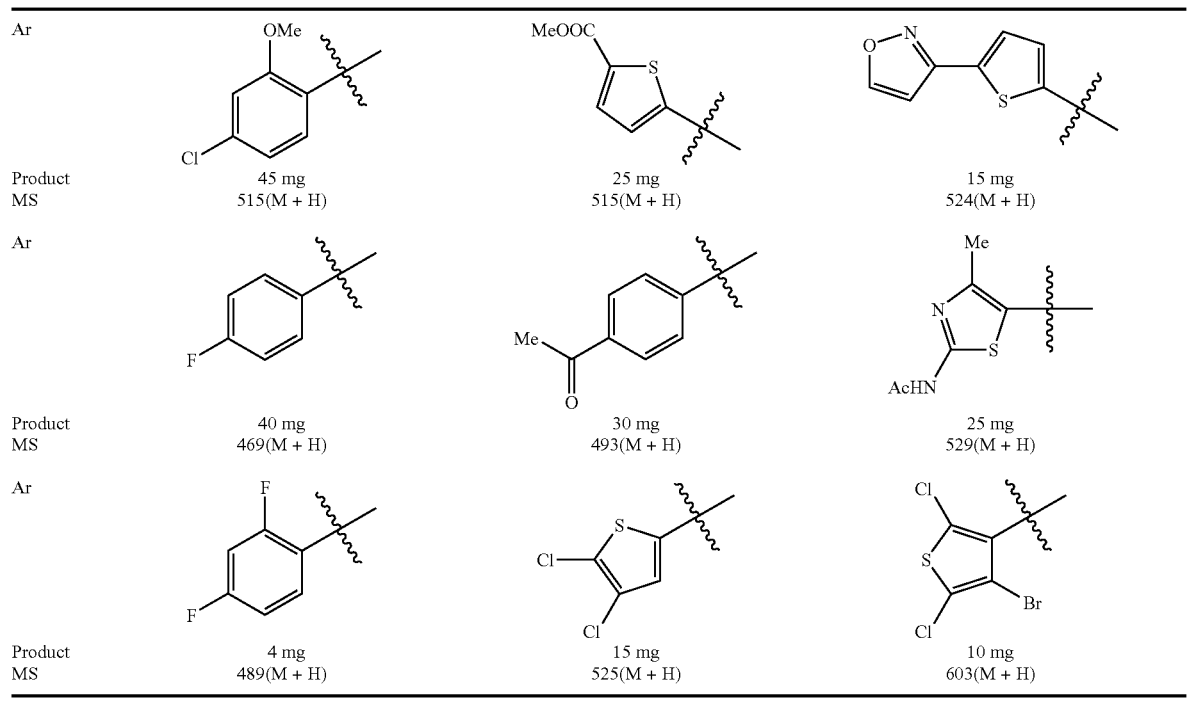

| Ar | | | |
|---|---|---|---|
| Product | 45 mg | 25 mg | 15 mg |
| MS | 515(M + H) | 515(M + H) | 524(M + H) |
| Ar | | | |
| Product | 40 mg | 30 mg | 25 mg |
| MS | 469(M + H) | 493(M + H) | 529(M + H) |
| Ar | | | |
| Product | 4 mg | 15 mg | 10 mg |
| MS | 489(M + H) | 525(M + H) | 603(M + H) |

Example 400

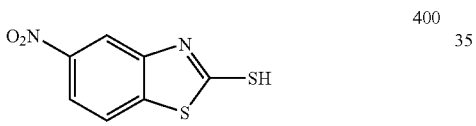

5-Nitro-benzothiazole-2-thiol (400). 5-Nitro-benzothiazole-2-thiol was synthesized from 2-chloro-5-nitro-aniline (Lancaster) in a similar manner as described in Example 252. This product without further purification was used directly in Example 409. $^1$H NMR (400 MHz, DMSO-$d_6$) δ 13.95 (br s, 1H), 8.14 (dd, J=8.8, 2.3 Hz, 1H), 7.97 (d, J=8.5 Hz, 1H), 7.96 (d, J=1.8 Hz, 1H).

Example 401

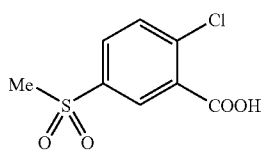

2-Chloro-5-methanesulfonyl-benzoic acid (401). To a solution of 2-chloro-5-methylsulfanyl-benzoic acid (Aldrich, 10.15 g, 50 mmol) in 100 mL of 3:1 CH$_2$Cl$_2$/MeOH, was added m-CPBA (Aldrich, 37.83 g, 57-87%, 125 mmol) in portions. The mixture was stirred overnight. After removal of the solvent under reduced pressure, the residue was purified by chromatography, eluting with 50% EtOAc/Hexanes then 10% MeOH/CH$_2$Cl$_2$, to give 8.5 g (70%) of product. $^1$H NMR (400 MHz, DMSO-$d_6$) δ 8.26 (d, J=2.3 Hz, 1H), 8.04 (dd, J=8.4, 2.3 Hz, 1H), 7.84 (d, J=8.4 Hz, 1H), 3.29 (s, 3H).

Example 402

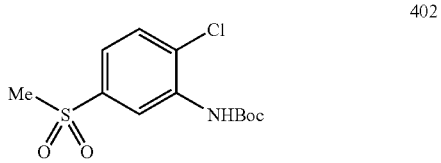

(2-Chloro-5-methanesulfonyl-phenyl)-carbamic acid tert-butyl ester (402). (2-Chloro-5-methanesulfonyl-phenyl)-carbamic acid tert-butyl ester was synthesized (79%) from 2-chloro-5-methanesulfonyl-benzoic acid (401) in a similar manner as described in Example 263. $^1$H NMR (400 MHz, DMSO-$d_6$) δ 9.02 (S, 1H), 8.21 (d, J=2.1 Hz, 1H), 7.75 (d, J=8.4 Hz, 1H), 7.65 (dd, J=8.4, 2.2 Hz, 1H), 3.23 (s, 3H), 1.48 (s, 9H). MS (EI): m/z 304 (M−H).

Example 403

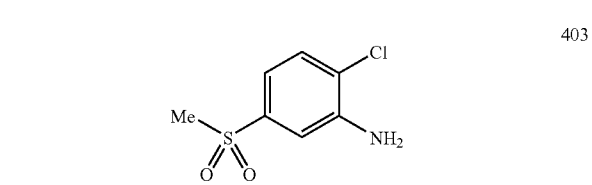

2-Chloro-5-methanesulfonyl-phenylamine (403). 2-Chloro-5-methanesulfonyl-phenylamine was synthesized from (2-chloro-5-methanesulfonyl-phenyl)-carbamic acid tert-butyl ester (402) in a similar manner as described in Example 273. This product without further purification was used directly in Example 404. NMR (400 MHz, DMSO-d$_6$) δ 7.45 (d, J=8.3 Hz, 1H), 7.30 (d, J=2.2 Hz, 1H), 7.01 (dd, J=8.3, 2.2 Hz, 1H), 5.94 (s, 2H), 3.14 (s, 3H).

Example 404

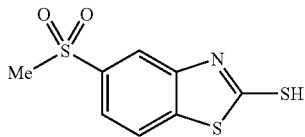

404

5-Methanesulfonyl-benzothiazole-2-thiol (404). 5-Methanesulfonyl-benzothiazole-2-thiol was synthesized from 2-chloro-5-methanesulfonyl-phenylamine (403) in a similar manner as described in Example 252. This product without further purification was used directly in Example 410. $^1$H NMR (400 MHz, DMSO-d$_6$) δ 14.25 (br s, 1H), 7.98 (d, J=8.4 Hz, 1H), 7.81 (dd, J=8.4, 1.8 Hz, 1H), 7.72 (d, J=1.7 Hz, 1H), 3.26 (s, 3H).

Example 405

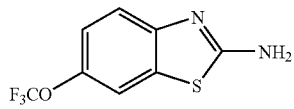

405

6-Trifluoromethoxy-benzothiazol-2-ylamine (405). To a solution of 4-trifluoromethoxyaniline (Aldrich, 4.83 g, 30 mmol) in 50 mL of AcOH, was added KSCN (Aldrich, 11.64 g, 120 mmol). After the mixture was stirred for 30 min, a solution of bromine (Aldrich, 1.55 mL, 30 mmol) in 20 mL of AcOH was added over 30 min period, and the resulting reaction mixture was stirred overnight. The mixture was diluted with ice/water, brought to pH 8 with conc. NH$_4$OH. The mixture extracted 3× with EtOAc (300 mL). The organic layers were washed twice with a brine solution (300 mL), dried over Na$_2$SO$_4$ and concentrated. The residue was purified by chromatography (40%-45% EtOAc/Hexanes) to give 6.0 g (85%) of product. $^1$H NMR (400 MHz, DMSO-d$_6$) δ 7.76 (d, J=2.2 Hz, 1H), 7.63 (s, 2H), 7.36 (d, J=8.7 Hz, 1H), 7.17 (dd, J=8.7, 2.4 Hz, 1H), 3.23 (s, 3H). MS (EI): m/z 235 (M+H).

Example 406

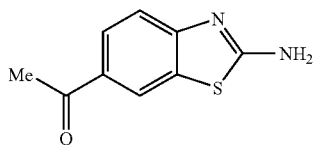

406

1-(2-Amino-benzothiazol-6-yl)ethanone (406). 1-(2-Amino-benzothiazol-6-yl)-ethanone was synthesized from 4'-aminoacetophenone (Aldrich) in a similar manner as described in Example 405 except the workup. After the mixture was brought to pH 8, precipitate was formed. Filtration followed by washing with water gave a yellow solid, which was triturated with CH$_2$Cl$_2$/hexanes. This product without further purification was used directly in Example 415. $^1$H NMR (400 MHz, DMSO-d$_6$) δ 8.32 (d, J=1.7 Hz, 1H), 7.91 (s, 2H), 7.83 (dd, J=8.4, 1.7 Hz, 1H), 7.37 (dd, J=8.4 Hz, 1H), 2.57 (s, 3H). MS (EI): m/z 193 (M+H).

Example 407

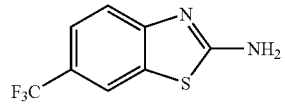

407

6-Trifluoromethyl-benzothiazol-2-ylamine (407). 6-Trifluoromethyl-benzothiazol-2-ylamine was synthesized from 4-trifluoromethylaniline (Aldrich) in a similar manner as described in Example 405. $^1$H NMR (400 MHz, DMSO-d$_6$) δ 8.70 (s, 1H), 8.16 (d, J=8.2 HZ, 1H), 7.99 (d, J=8.1 Hz, 1H).

Example 408

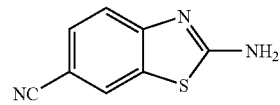

408

2-Amino-benzothiazole-6-carbonitrile (408). 2-Amino-benzothiazole-6-carbonitrile was synthesized from 4-aminobenzonitrile (Aldrich) in a similar manner as described in Example 406. $^1$H NMR (400 MHz, DMSO-d$_6$) δ 8.28 (d, J=1.7 Hz, 1H), 8.08 (s, 2H), 7.62 (dd, J=8.4, 1.7 Hz, 1H), 7.41 (d, J=8.4 Hz, 1H). MS (EI): m/z 176 (M+H).

TABLE 17

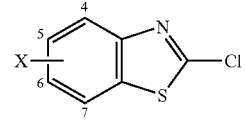

| Compound | X | Method |
|---|---|---|
| 409 | 5-NO$_2$ | A |
| 410 | 5-SO$_2$Me | A |
| 411 | 6-NO$_2$ | B |
| 412 | 6-SO$_2$Me | B |
| 413 | 6-OCF$_3$ | B |
| 414 | 6-CF$_3$ | B |
| 415 | 6-COMe | B |
| 416 | 6-CN | B |

The compounds of Table 17 were prepared using the method A as described in Example 253 or method B as described in Example 255.

Example 409

2-Chloro-5-nitro-benzothiazole (409). $^1$H NMR (400 MHz, DMSO-d$_6$) δ 8.79 (d, J=2.2 Hz, 1H), 8.42 (d, J=8.9 Hz, 1H), 8.36 (dd, J=8.9, 2.2 Hz, 1H).

Example 410

2-Chloro-5-methanesulfonyl-benzothiazole (410). $^1$H NMR (400 MHz, DMSO-d$_6$) δ 8.47 (d, J=1.6 Hz, 1H), 8.42 (d, J=8.6 Hz, 1H), 8.03 (dd, J=8.5, 1.8 Hz, 1H), 3.31 (s, 3H).

Example 411

2-Chloro-6-nitro-benzothiazole (411). $^1$H NMR (400 MHz, DMSO-d$_6$) δ 9.18 (d, J=2.4 Hz, 1H), 8.37 (dd, J=9.0, 2.5 Hz, 1H), 8.17 (d, J=9.0 Hz, 1H).

Example 412

2-Chloro-6-methanesulfonyl-benzothiazole (412). $^1$H NMR (400 MHz, DMSO-d$_6$) δ 8.82 (d, J=1.8 Hz, 1H), 8.22 (d, J=8.5 Hz, 1H), 8.08 (dd, J=8.5, 1.8 Hz, 1H), 3.28 (s, 3H).

Example 413

2-Chloro-6-trifluoromethoxybenzothiazole (413). $^1$H NMR (400 MHz, DMSO-d$_6$) δ 8.28 (d, J=1.5 Hz, 1H), 8.08 (d, J=8.9 HZ, 1H), 7.57 (dd, J=8.9, 1.5 Hz, 1H).

Example 414

2-Chloro-6-trifluoromethylbenzothiazole (414). $^1$H NMR (400 MHz, DMSO-d$_6$) δ 8.64 (s, 1H), 8.16 (d, J=8.4 HZ, 1H), 7.87 (dd, J=8.4, 1.6 Hz, 1H).

Example 415

1-(2-Chloro-benzothiazol-6-yl)-ethanone (415). $^1$H NMR (400 MHz, DMSO-d$_6$) δ 8.81 (d, J=1.6 Hz, 1H), 8.11 (dd, J=8.6, 1.7 HZ, 1H), 8.07 (d, J=8.6 Hz, 1H), 2.66 (s, 3H).

Example 416

2-Chloro-6-cyanobenzothiazole (416). $^1$H NMR (400 MHz, DMSO-d$_6$) δ 8.70 (s, 1H), 8.16 (d, J=8.2 HZ, 1H), 7.99 (d, J=8.1 Hz, 1H).

Example 417

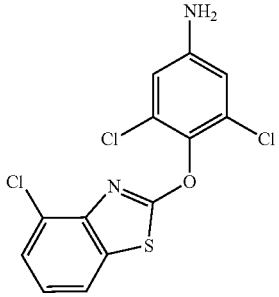

3,5-Dichloro-4-(4-chloro-benzothiazol-2-yloxy)-phenylamine (417). To solution of 2,4-dichlorobenzothiazole (255, 2.23 g, 11 mmol) and 4-amino-2,6-dichlorophenol (Aldrich, 1.78 g, 10 mmol) in 10 mL of DMSO was add K$_2$CO$_3$ (Aldrich, 4.14 g, 30 mmol). The mixture was heated at 145° C. for 4 h. After cooled to room temperature, the reaction mixture was diluted with EtOAc (300 mL) and filtered through a pad of silica gel and activated carbon followed by washing with EtOAc (500 mL). The filtrate was concentrated and the residue was purified by chromatography (20%-30% EtOAc/Hexanes) to give 1.15 g (33%) of product. $^1$H NMR (400 MHz, DMSO-d$_6$) δ 7.92 (d, J=8.0 Hz, 1H), 7.55 (d, J=7.9 Hz, 1H), 7.34 (t, J=8.0 Hz, 1H), 6.75 (s, 2H), 5.93 (s, 2H). MS (EI): m/z 345 (M+H).

Example 418

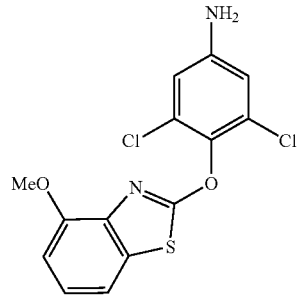

3,5-Dichloro-4-(4-methoxy-benzothiazol-2-yloxy)-phenylamine (418). 3,5-Dichloro-4-(4-methoxy-benzothiazol-2-yloxy)-phenylamine was synthesized (21%) from 2-chloro-4-methoxybenzothiazole (257) and 4-amino-2,6-dichlorophenol (Aldrich) in a similar manner as described in Example 417. $^1$H NMR (400 MHz, DMSO-d$_6$) δ 7.48 (d, J=8.0 Hz, 1H), 7.28 (t, J=8.1 Hz, 1H), 7.01 (d, J=8.1 Hz, 1H), 6.73 (s, 2H), 5.86 (s, 2H), 3.85 (s, 3H). MS (EI): m/z 341 (M+H).

Example 419

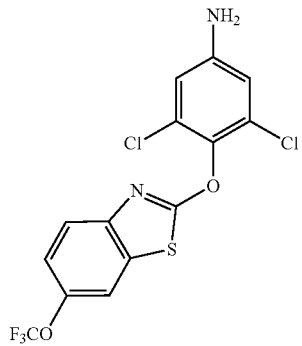

3,5-Dichloro-4-(6-trifluoromethoxy-benzothiazol-2-yloxy)-phenylamine (419). 3,5-Dichloro-4-(6-trifluoromethoxy-benzothiazol-2-yloxy)-phenylamine was synthesized (76%) from 2-chloro-6-trifluoromethoxybenzothiazole (413) and 4-amino-2,6-dichlorophenol (Aldrich) in a similar manner as described in Example 417. $^1$H NMR (400 MHz, DMSO-d$_6$) δ 8.10 (d, J=1.6 Hz, 1H), 7.80 (d, J=8.8 Hz, 1H), 7.44 (ddd, J=8.8, 1.6, 0.8 Hz, 1H), 6.74 (s, 2H), 5.87 (s, 2H). MS (EI): m/z 395 (M+H).

Example 420

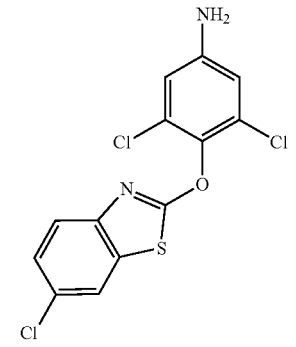

3,5-Dichloro-4-(6-chloro-benzothiazol-2-yloxy)-phenylamine (420). 3,5-Dichloro-4-(6-chloro-benzothiazol-2-yloxy)-phenylamine was synthesized (65%) from 2,6-dichlorobenzothiazole (259) and 4-amino-2,6-dichlorophenol (Aldrich) in a similar manner as described in Example 417. $^1$H NMR (400 MHz, DMSO-d$_6$) δ 8.10 (d, J=2.2 Hz, 1H), 7.78 (d, J=8.7 Hz, 1H), 7.47 (dd, J=8.7, 2.2 Hz, 1H), 6.73 (s, 2H), 5.88 (s, 2H). MS (EI): m/z 345 (M+H).

Example 421

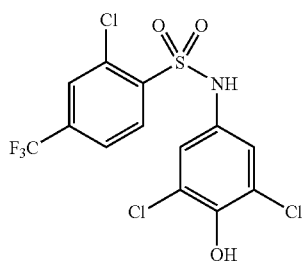

421

2-Chloro-N-(3,5-dichloro-4-hydroxy-phenyl)-4-trifluoromethylbenzenesulfonamide (421). To a solution of 4-amino-2,6-dichlorophenol (Aldrich, 5.9 g, 33 mmol) in 30 mL of THF was added 2-chloro-4-trifluoromethylbenzenesulfonyl chloride (4.19 g, 15 mmol). The mixture was stirred overnight. The reaction mixture was filtered and washed with EtOAc. The filtrate was washed with 2N HCl, twice with a brine solution, dried over Na$_2$SO$_4$ and concentrated. The residue was purified by chromatography (20%-25% EtOAc/hexanes) to give 5.7 g (90%) of product. $^1$H NMR (400 MHz, DMSO-d$_6$) δ 10.89 (s, 1H), 10.15 (s, 10H), 8.19 (d, J=8.3 Hz, 1H), 8.16 (d, J=1.1 Hz, 1H), 7.92 (dd, J=8.3, 2.2 Hz, 1H), 7.06 (s, 2H). MS (EI): m/z 418 (M+H).

Example 422

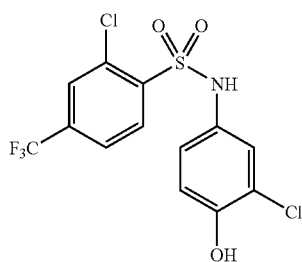

422

2-Chloro-N-(3-chloro-4-hydroxy-phenyl)-4-trifluoromethylbenzenesulfonamide (422). 2-Chloro-N-(3-chloro-4-hydroxy-phenyl)-4-trifluoromethylbenzenesulfonamide was synthesized (92%) from 4-amino-2-chlorophenol (Aldrich) and 2-chloro-4-trifluoromethylbenzenesulfonyl chloride in a similar manner as described in Example 421. $^1$H NMR (400 MHz, DMSO-d$_6$) δ 10.57 (s, 1H), 10.17 (s, 1H), 8.14 (d, J=1.0 Hz, 1H), 8.12 (d, J=8.3 Hz, 1H), 7.88 (dd, J=8.5, 1.4 Hz, 1H), 7.04 (d, J=2.5 Hz, 1H), 6.88 (dd, J=8.7, 2.5 Hz, 1H), 6.82 (d, J=8.7 Hz, 1H). MS (EI): m/z 384 (M+H).

Example 423

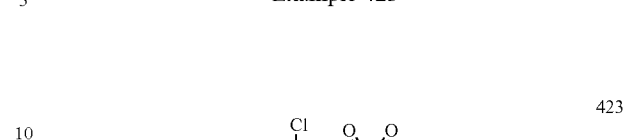

423

2-Chloro-N-(4-hydroxy-phenyl)-4-trifluoromethylbenzenesulfonamide (423). 2-Chloro-N-(4-hydroxy-phenyl)-4-trifluoromethylbenzenesulfonamide was synthesized (98%) from 4-aminophenol (Aldrich) and 2-chloro-4-trifluoromethylbenzenesulfonyl chloride in a similar manner as described in Example 421. $^1$H NMR (400 MHz, DMSO-d$_6$) δ 10.30 (s, 1H), 9.39 (s, 1H), 8.12 (s, 1H), 8.06 (d, J=8.2 Hz, 1H), 7.85 (d, J=8.1 Hz, 1H), 6.89 (m, 2H), 6.61 (m, 2H). MS (EI): m/z 384 (M+H).

Examples 424-432

The compounds of Table 18 were prepared using Method D described in Examples 70-91 and the corresponding arylsulfonyl chloride.

TABLE 18

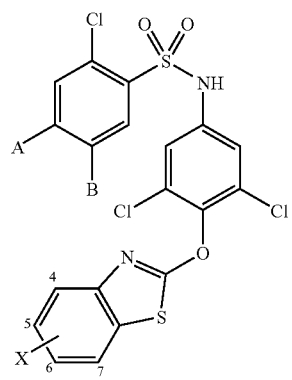

| Compound | X | A | B |
|---|---|---|---|
| 424 | 4-Cl | CF$_3$ | H |
| 425 | 4-Cl | Cl | H |
| 426 | 4-Cl | Cl | Me |
| 427 | 4-OMe | CF$_3$ | H |
| 428 | 4-OMe | Cl | H |
| 429 | 4-OMe | Cl | Me |
| 430 | 6-OCF$_3$ | CF$_3$ | H |
| 431 | 6-OCF$_3$ | Cl | H |
| 432 | 6-OCF$_3$ | Cl | Me |

Example 424

2-Chloro-N-[3,5-dichloro-4-(4-chloro-benzothiazol-2-yloxy)-phenyl]-4-trifluoromethyl-benzenesulfonamide (424). $^1$H NMR (400 MHz, DMSO-$d_6$) δ 11.65 (s, 1H), 8.37 (d, J=8.3 Hz, 1H), 8.21 (d, J=1.0 Hz, 1H), 8.00 (dd, J=8.3, 1.1 Hz, 1H), 7.96 (dd, J=8.1, 0.9 Hz, 1H), 7.55 (dd, J=8.0, 0.9 Hz, 1H), 7.36 (t, J=8.0 Hz, 1H), 7.33 (s, 2H). MS (EI): m/z 585 (M–H).

Example 425

2,4-Dichloro-N-[3,5-dichloro-4-(4-chloro-benzothiazol-2-yloxy)-phenyl]-benzenesulfonamide (425). $^1$H NMR (400 MHz, DMSO-$d_6$) δ 11.50 (s, 1H), 8.16 (d, J=8.6 Hz, 1H), 7.98-7.94 (m, 2H), 7.70 (dd, J=8.6, 2.1 Hz, 1H), 7.55 (dd, J=7.9, 0.8 Hz, 1H), 7.36 (t, J=8.0 Hz, 1H), 7.30 (s, 2H). MS (EI): m/z 551 (M–H).

Example 426

2,4-Dichloro-N-[3,5-dichloro-4-(4-chloro-benzothiazol-2-yloxy)-phenyl]-5-methyl-benzenesulfonamide (426). $^1$H NMR (400 MHz, DMSO-$d_6$) δ 11.43 (s, 1H), 8.19 (s, 1H), 7.96 (d, J=8.0 Hz, 1H), 7.90 (s, 1H), 7.55 (d, J=7.9 Hz, 1H), 7.36 (t, J=8.0 Hz, 1H), 7.31 (s, 2H), 2.40 (s, 3H). MS (EI): m/z 565 (M–H).

Example 427

2-Chloro-N-[3,5-dichloro-4-(4-methoxy-benzothiazol-2-yloxy)-phenyl]-4-trifluoromethyl-benzenesulfonamide (427). $^1$H NMR (400 MHz, DMSO-$d_6$) δ 11.65 (s, 1H), 8.38 (d, J=8.3 Hz, 1H), 8.20 (s, 1H), 8.00 (dd, J=8.3, 0.8 Hz, 1H), 7.51 (d, J=8.1 Hz, 1H), 7.32 (s, 2H), 7.30 (t, J=8.1 Hz, 1H), 7.00 (d, J=8.2 Hz, 1H), 3.79 (s, 3H). MS (EI): m/z 581 (M–H).

Example 428

2,4-Dichloro-N-[3,5-dichloro-4-(4-methoxy-benzothiazol-2-yloxy)-phenyl]-benzenesulfonamide (428). $^1$H NMR (400 MHz, DMSO-$d_6$) δ 11.49 (s, 1H), 8.17 (d, J=8.6 Hz, 1H), 7.96 (d, J=2.1 Hz, 1H), 7.71 (dd, J=8.6, 2.1 Hz, 1H), 7.51 (d, J=8.1 Hz, 1H), 7.30 (t, J=8.1 Hz, 1H), 7.28 (s, 2H), 7.01 (d, J=8.2 Hz, 1H), 3.81 (s, 3H). MS (EI): m/z 547 (M–H).

Example 429

2,4-Dichloro-N-[3,5-dichloro-4-(4-methoxy-benzothiazol-2-yloxy)-phenyl]-5-methyl-benzenesulfonamide (429). $^1$H NMR (400 MHz, DMSO-$d_6$) δ 11.42 (s, 1H), 8.20 (s, 1H), 7.90 (s, 1H), 7.51 (d, J=8.1 Hz, 1H), 7.30 (t, J=8.1 Hz, 1H), 7.29 (s, 2H), 7.01 (d, J=8.2 Hz, 1H), 3.81 (s, 3H), 2.41 (s, 3H). MS (EI): m/z 561 (M–H).

Example 430

2-Chloro-N-[3,5-dichloro-4-(6-trifluoromethoxy-benzothiazol-2-yloxy)-phenyl]-4-trifluoromethyl-benzenesulfonamide (430). $^1$H NMR (400 MHz, DMSO-$d_6$) δ 11.63 (s, 1H), 8.38 (d, J=8.2 Hz, 1H), 8.20 (d, J=1.2 Hz, 1H), 8.14 (d, J=1.6 Hz, 1H), 8.00 (dd, J=8.3, 1.2 Hz, 1H), 7.77 (d, J=8.8 Hz, 1H), 7.42 (dd, J=8.8, 2.0 Hz, 1H), 7.32 (s, 2H). MS (EI): m/z 635 (M–H).

Example 431

2,4-Dichloro-N-[3,5-dichloro-4-(6-trifluoromethoxy-benzothiazol-2-yloxy)-phenyl]-benzenesulfonamide (431). $^1$H NMR (400 MHz, DMSO-$d_6$) δ 11.49 (s, 1H), 8.18 (d, J=8.6 Hz, 1H), 8.15 (d, J=1.7 Hz, 1H), 7.96 (d, J=2.1 Hz, 1H), 7.79 (d, J=8.8 Hz, 1H), 7.71 (dd, J=8.6, 2.1 Hz, 1H), 7.42 (dd, J=8.7, 2.1 Hz, 1H), 7.29 (s, 2H). MS (EI): m/z 601 (M–H).

Example 432

2,4-Dichloro-N-[3,5-dichloro-4-(6-trifluoromethoxy-benzothiazol-2-yloxy)-phenyl]-5-methyl-benzenesulfonamide (432). $^1$H NMR (400 MHz, DMSO-$d_6$) δ 11.41 (s, 1H), 8.20 (s, 1H), 8.14 (d, J=1.7 Hz, 1H), 7.89 (s, 1H), 7.79 (d, J=8.9 Hz, 1H), 7.42 (d, J=8.8, 2.0 Hz, 1H), 7.30 (s, 2H), 2.41 (s, 3H). MS (EI): m/z 615 (M–H).

Example 433

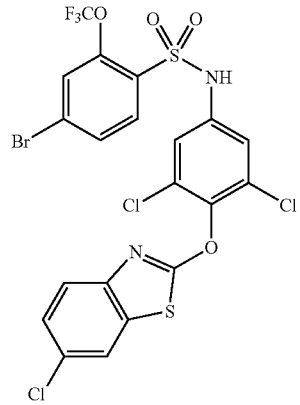

433

4-Bromo-N-[3,5-dichloro-4-(6-chloro-benzothiazol-2-yloxy)-phenyl]-2-trifluor methoxy-benzenesulfonamide (433). 4-Bromo-N-[3,5-dichloro-4-(6-chloro-benzothiazol-2-yloxy)-phenyl]-2-trifluoromethoxy-benzenesulfonamide was synthesized (83%) from 3,5-dichloro-4-(6-chloro-benzothiazol-2-yloxy)-phenylamine (420) and 4-bromo-2-trifluoromethoxybenzenesulfonyl chloride (Maybridge) in a similar manner as described in Examples 70-91. $^1$H NMR (400 MHz, DMSO-$d_6$) δ 11.37 (s, 1H), 8.16 (d, J=2.2 Hz, 1H), 8.03 (d, J=8.8 Hz, 1H), 7.91-7.87 (m, 2H), 7.68 (d, J=8.7 Hz, 1H), 7.47 (d, J=8.7, 2.2 Hz, 1H), 7.31 (s, 2H). MS (EI): m/z 645 (M–H).

Example 434

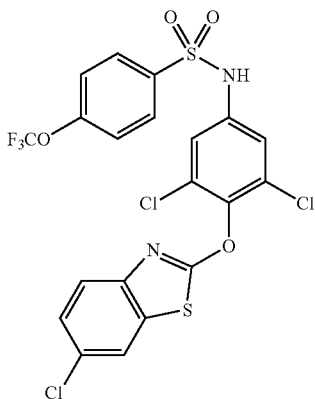

N-[3,5-Dichloro-4-(6-chloro-benzothiazol-2-yloxy)-phenyl]-4-trifluoromethoxy-benzenesulfonamide (434). N-[3,5-Dichloro-4-(6-chloro-benzothiazol-2-yloxy)-phenyl]-4-trifluoromethoxy-benzenesulfonamide was synthesized (83%) from 3,5-dichloro-4-(6-chloro-benzothiazol-2-yloxy)-phenylamine (420) and 4-trifluoromethoxybenzenesulfonyl chloride (Maybridge) in a similar manner as described in Examples 70-91. $^1$H NMR (400 MHz, DMSO-$d_6$) δ 11.16 (s, 1H), 8.15 (d, J=2.2 Hz, 1H), 8.03-7.98 (m, 2H), 7.68 (d, J=8.7 Hz, 1H), 7.65 (d, J=8.2 Hz, 2H), 7.46 (dd, J=8.7, 2.2 Hz, 1H), 7.31 (s, 2H). MS (EI): m/z 567 (M−H).

Example 435

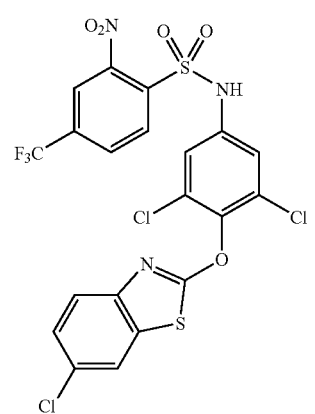

N-[3,5-Dichloro-4-(6-chloro-benzothiazol-2-yloxy)-phenyl]-2-nitro-4-trifluoromethyl-benzenesulfonamide (435). N-[3,5-Dichloro-4-(6-chloro-benzothiazol-2-yloxy)-phenyl]-2-nitro-4-trifluoromethyl-benzenesulfonamide was synthesized (48%) from 3,5-dichloro-4-(6-chloro-benzothiazol-2-yloxy)-phenylamine (420) and 2-nitro-4-trifluoromethylbenzenesulfonyl chloride (Aldrich) in a similar manner as described in Examples 70-91. $^1$H NMR (400 MHz, DMSO-$d_6$) δ 11.65 (br s, 1H), 8.61 (s, 1H), 8.32-8.28 (m, 2H), 8.15 (d, J=2.2 Hz, 1H), 7.68 (d, J=8.7 Hz, 1H), 7.46 (dd, J=8.7, 2.2 Hz, 1H), 7.34 (s, 2H). MS (EI): m/z 596 (M−H).

Example 436

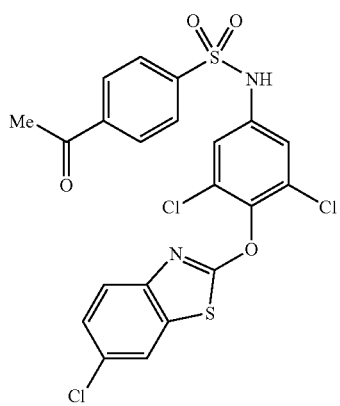

4-Acetyl-N-[3,5-dichloro-4-(6-chloro-benzothiazol-2-yloxy)-phenyl]-benzenesulfonamide (436). 4-Acetyl-N-[3,5-dichloro-4-(6-chloro-benzothiazol-2-yloxy)-phenyl]-benzenesulfonamide was synthesized (36%) from 3,5-dichloro-4-(6-chloro-benzothiazol-2-yloxy)-phenylamine (420) and 4-acetyl-benzenesulfonyl chloride (Fluka) in a similar manner as described in Examples 70-91. $^1$H NMR (400 MHz, DMSO-$d_6$) δ 11.24 (br s, 1H), 8.18 (dd, J=7.8, 1.7 Hz, 2H), 8.15 (d, J=2.2 Hz, 1H), 8.01 (d, J=7.8, 1.7 Hz, 2H), 7.67 (d, J=8.7 Hz, 1H), 7.46 (dd, J=8.7, 2.2 Hz, 1H), 7.32 (s, 2H), 2.63 (s, 3H). MS (EI): m/z 525 (M−H).

Example 437

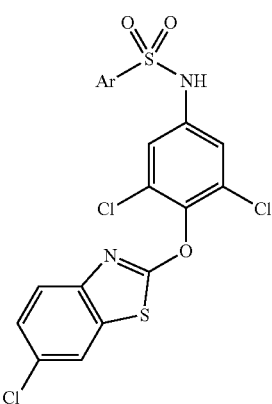

Compound 437 was synthesized in a similar manner as described in Example 334, from 3,5-dichloro-4-(6-chloro-benzothiazol-2-yloxy)-phenylamine (420) and corresponding arylsulfonyl chloride.

| Ar | Me Cl (2-Cl-3-Me-phenyl) | Me F (2-Me-4-F-phenyl) | PhSO₂-thiophene | 2,5-dichlorothiophene |
|---|---|---|---|---|
| Product | 40 mg | 30 mg | 30 mg | 40 mg |
| MS | 531(M – H) | 515(M – H) | 629(M – H) | 557(M – H) |

| Ar | 2-CF₃-phenyl | 2-Cl-4-CF₃-phenyl | 5-Cl-3-Br-thiophene | 5-Br-thiophene |
|---|---|---|---|---|
| Product | 10 mg | 25 mg | 10 mg | 10 mg |
| MS | 551(M – H) | 585(M – H) | 601(M – H) | 567(M – H) |

| Ar | 5-Cl-4-Br-thiophene | 4-NO₂-phenyl | 2-OMe-4-Cl-phenyl |
|---|---|---|---|
| Product | 40 mg | 15 mg | 40 mg |
| MS | 601(M – H) | 528(M – H) | 547(M – H) |

Example 438

2-Chloro-N-[3,5-dichloro-4-(6-nitro-benzothiazol-2-yloxy)-phenyl]-4-trifluoromethyl-benzenesulfonamide (438). To a solution of 2-chloro-N-(3,5-dichloro-4-hydroxy-phenyl)-4-trifluoromethyl-benzenesulfonamide (421, 1.52 g, 3.41 mmol) in 10 mL of DMF, was added NaH (Aldrich, 288 mg, 60%, 7.2 mmol). The mixture was stirred for 10 min, then 2-chloro-6-nitrobenzothiazole (411, 765 mg, 3.56 mmol) was added. The reaction mixture was stirred until no 421 remained by TLC. The mixture was diluted with EtOAc and 2N HCl, extracted 3× with EtOAc (100 mL). The organic layers were washed twice with a brine solution (100 mL), dried over Na₂SO₄ and concentrated. The residue was purified by chromatography (15%-20% EtOAc/hexanes) to give 1.5 g (74%) of product. $^1$H NMR (400 MHz, DMSO-d$_6$) δ 11.69 (s, 1H), 9.08 (d, J=2.4 Hz, 1H), 8.38 (d, J=8.3 Hz, 1H), 8.26 (dd, J=9.0, 2.4 Hz, 1H), 8.22 (s, 1H), 8.00 (d, J=8.4 Hz, 1H), 7.87 (d, J=9.0 Hz, 1H), 7.33 (s, 2H). MS (EI): m/z 596 (M–H).

Examples 439-459

The compounds listed in Table 19 were prepared from compounds 421-423 and 409-416 in a similar manner as described in Example 438.

TABLE 19

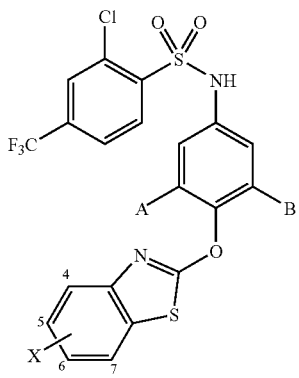

| Compound | X | A | B |
|---|---|---|---|
| 438 | 6-NO₂ | Cl | Cl |
| 441 | 6-SO₂Me | Cl | Cl |
| 442 | 6-NO₂ | Cl | H |
| 445 | 6-SO₂Me | Cl | H |
| 446 | 6-SO₂Me | H | H |
| 447 | 6-NO₂ | H | H |
| 450 | 6-Cl | H | H |
| 451 | 6-OMe | H | H |
| 452 | 4-OMe | H | H |
| 453 | 6-CF₃ | H | H |
| 454 | 6-CN | H | H |
| 455 | 5-NO₂ | Cl | Cl |
| 458 | 5-SO₂Me | Cl | Cl |
| 459 | 6-COMe | Cl | Cl |

Example 439

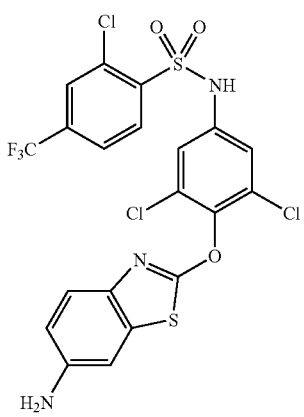

N-[4-(6-Amino-benzothiazol-2-yloxy)-3,5-dichloro-phenyl]-2-chloro-4-trifluoromethyl-benzenesulfonamide (439). N-[4-(6-Amino-benzothiazol-2-yloxy)-3,5-dichloro-phenyl]-2-chloro-4-trifluoromethyl-benzenesulfonamide was synthesized from 2-chloro-N-[3,5-dichloro-4-(6-nitro-benzothiazol-2-yloxy)-phenyl]-4-trifluoromethyl-benzenesulfonamide (438) in a similar manner as described in Examples 16-23 (Method A). $^1$H NMR (400 MHz, DMSO-$d_6$) δ 8.36 (d, J=8.2 Hz, 1H), 8.20 (s, 1H), 7.99 (dd, J=8.3, 1.1 Hz, 1H), 7.28 (d, J=8.6 Hz, 1H), 7.28 (s, 2H), 6.98 (d, J=2.2 Hz, 1H), 6.64 (dd, J=8.6, 2.2 Hz, 1H). MS (EI): m/z 568 (M+H).

Example 440

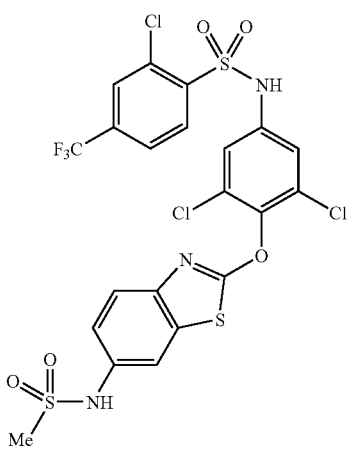

2-Chloro-N-[3,5-dichloro-4-(6-methanesulfonylamino-benzothiazol-2-yloxy)-phenyl]-4-trifluoromethyl-benzenesulfonamide (440). 2-Chloro-N-[3,5-dichloro-4-(6-methanesulfonylamino-benzothiazol-2-yloxy)-phenyl]-4-trifluoromethyl-benzenesulfonamide was synthesized from N-[4-(6-Amino-benzothiazol-2-yloxy)-3,5-dichloro-phenyl]-2-chloro-4-trifluoromethyl-benzenesulfonamide (439) and methanesulfonyl chloride (Aldrich) in a similar manner as described in Examples 70-91. $^1$H NMR (400 MHz, DMSO-$d_6$) δ 11.64 (s, 1H), 9.87 (s, 1H), 8.38 (d, J=8.3 Hz, 1H), 8.22 (s, 1H), 8.00 (d, J=8.2 Hz, 1H), 7.83 (d, J=1.8 Hz, 1H), 7.62 (d, J=8.8 Hz, 1H), 7.31 (s, 2H), 7.23 (dd, J=8.8, 1.5 Hz, 1H). MS (EI): m/z 644 (M−H).

Example 441

2-Chloro-N-[3,5-dichloro-4-(6-methanesulfonyl-benzothiazol-2-yloxy)-phenyl]-4-trifluoromethyl-benzenesulfonamide (441). $^1$H NMR (400 MHz, DMSO-$d_6$) δ 11.66 (s, 1H), 8.67 (d, J=1.6 Hz, 1H), 8.36 (d, J=8.3 Hz, 1H), 8.19 (s, 1H), 7.99 (d, J=8.1 Hz, 1H), 7.94 (dd, J=8.6, 1.8 Hz, 1H), 7.90 (d, J=8.6 Hz, 1H), 7.29 (s, 2H), 3.24 (s, 3H). MS (EI): m/z 629 (M−H).

Example 442

2-Chloro-N-[3-chloro-4-(6-nitro-benzothiazol-2-yloxy)-phenyl]-4-trifluoromethyl-benzenesulfonamide (442). $^1$H NMR (400 MHz, DMSO-$d_6$) δ 11.43 (s, 1H), 9.04 (d, J=2.4 Hz, 1H), 8.34 (d, J=8.2 Hz, 1H), 8.26 (dd, J=9.0, 2.5 Hz, 1H), 8.20 (d, J=1.0 Hz, 1H), 7.99 (dd, J=8.3, 1.1 Hz, 1H), 7.85 (d, J=9.0 Hz, 1H), 7.62 (d, J=8.9 Hz, 1H), 7.35 (d, J=2.6 Hz, 1H), 7.21 (dd, J=8.9, 2.6 Hz, 1H). MS (EI): m/z 562 (M−H).

Example 443

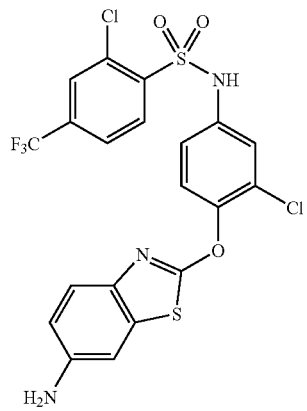

N-[4-(6-Amino-benzothiazol-2-yloxy)-3-chloro-phenyl]-2-chloro-4-trifluoromethyl-benzenesulfonamide (443). N-[4-(6-Amino-benzothiazol-2-yloxy)-3-chloro-phenyl]-2-chloro-4-trifluoromethyl-benzenesulfonamide was synthesized from 2-chloro-N-[3-chloro-4-(6-nitro-benzothiazol-2-yloxy)-phenyl]-4-trifluoromethyl-benzenesulfonamide (442) in a similar manner as described in Examples 16-23 (Method A). $^1$H NMR (400 MHz, DMSO-$d_6$) δ 8.31 (d, J=8.2 Hz, 1H), 8.18 (d, J=1.1 Hz, 1H), 7.97 (dd, J=8.3, 1.2 Hz, 1H), 7.49 (d, J=8.9 Hz, 1H), 7.30 (d, J=1.9 Hz, 1H), 7.28 (d, J=8.7 Hz, 1H), 7.15 (dd, J=8.9, 2.6 Hz, 1H), 6.94 (d, J=2.2 Hz, 1H), 6.64 (dd, J=8.7, 2.3 Hz, 1H). MS (EI): m/z 534 (M+H).

Example 444

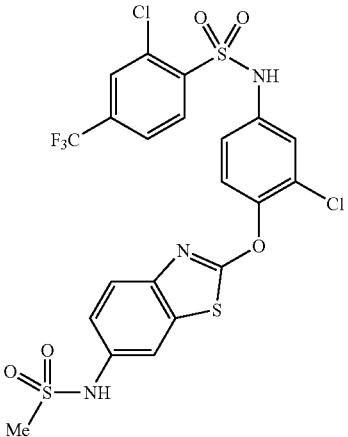

2-Chloro-N-[3-chloro-4-(6-methanesulfonylamino-benzothiazol-2-yloxy)-phenyl]-4-trifluoromethyl-benzenesulfonamide (444). 2-Chloro-N-[3-dichloro-4-(6-methanesulfonylamino-benzothiazol-2-yloxy)-phenyl]-4-trifluoromethyl-benzenesulfonamide was synthesized from N-[4-(6-Amino-benzothiazol-2-yloxy)-3-chloro-phenyl]-2-chloro-4-trifluoromethyl-benzenesulfonamide (443) and methanesulfonyl chloride (Aldrich) in a similar manner as described in Examples 70-91. $^1$H NMR (400 MHz, DMSO-$d_6$) δ 11.37 (s, 1H), 9.84 (s, 1H), 8.32 (d, J=8.3 Hz, 1H), 8.19 (s, 1H), 7.98 (d, J=8.3 Hz, 1H), 7.79 (d, J=1.9 Hz, 1H), 7.61 (d, J=8.7 Hz, 1H), 7.55 (d, J=8.8 Hz, 1H), 7.32 (d, J=1.9 Hz, 1H), 7.23 (dd, J=8.7, 1.5 Hz, 1H), 7.18 (dd, J=8.9, 1.9 Hz, 1H). MS (EI): m/z 610 (M−H).

Example 445

2-Chloro-N-[3-chloro-4-(6-methanesulfonyl-benzothiazol-2-yloxy)-phenyl]-4-trifluoromethyl-benzenesulfonamide (445). $^1$H NMR (400 MHz, DMSO-$d_6$) δ 11.42 (s, 1H), 8.63 (d, J=1.8 Hz, 1H), 8.34 (d, J=8.2 Hz, 1H), 8.20 (d, J=1.1 Hz, 1H), 7.99 (dd, J=8.3, 1.2 Hz, 1H), 7.93 (dd, J=8.6, 1.9 Hz, 1H), 7.88 (d, J=8.5 Hz, 1H), 7.61 (d, J=8.9 Hz, 1H), 7.35 (d, J=2.6 Hz, 1H), 7.21 (dd, J=8.9, 2.6 Hz, 1H), 3.24 (s, 3H). MS (EI): m/z 595 (M−H).

Example 446

2-Chloro-N-[4-(6-methanesulfonyl-benzothiazol-2-yloxy)-phenyl]-4-trifluoromethyl-benzenesulfonamide (446). $^1$H NMR (400 MHz, DMSO-$d_6$) δ 11.13 (s, 10H), 8.59 (d, J=1.3 Hz, 1H), 8.28 (d, J=8.3 Hz, 1H), 8.17 (s, 1H), 7.96 (d, J=8.2 Hz, 1H), 7.93 (dd, J=8.6, 1.9 Hz, 1H), 7.87 (d, J=8.5 Hz, 1H), 7.41 (d, J=9.0 Hz, 2H), 7.23 (d, J=8.9 Hz, 2H), 3.23 (s, 3H). MS (EI): m/z 561 (M−H).

Example 447

2-Chloro-N-[4-(6-nitro-benzothiazol-2-yloxy)-phenyl]-4-trifluoromethyl-benzenesulfonamide (447). $^1$H NMR (400 MHz, DMSO-$d_6$) δ 11.15 (s, 1H), 9.00 (d, J=2.5 Hz, 1H), 8.28 (d, J=9.2 Hz, 1H), 8.26 (dd, J=9.0, 2.5 Hz, 1H), 8.18 (s, 1H), 7.97 (dd, J=8.3, 1.2 Hz, 1H), 7.85 (d, J=9.0 Hz, 1H), 7.43 (d, J=9.0 Hz, 2H), 7.24 (d, J=9.0 Hz, 2H). MS (EI): m/z 528 (M−H).

Example 448

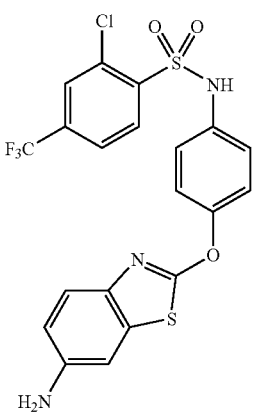

448

N-[4-(6-Amino-benzothiazol-2-yloxy)-phenyl]-2-chloro-4-trifluoromethyl-benzenesulfonamide (448). N-[4-(6-Amino-benzothiazol-2-yloxy)-phenyl]-2-chloro-4-trifluoromethyl-benzenesulfonamide was synthesized from 2-chloro-N-[4-(6-nitro-benzothiazol-2-yloxy)-phenyl]-4-trifluoromethyl-benzenesulfonamide (447) in a similar manner as described in Examples 16-23 (Method A). $^1$H NMR (400 MHz, DMSO-$d_6$) δ 11.02 (br s, 1H), 8.25 (d, J=8.3 Hz, 1H), 8.16 (d, J=1.0 Hz, 1H), 7.94 (dd, J=8.3, 1.0 Hz, 1H), 7.32-7.27 (m, 3H), 7.20-7.15 (m, 2H), 6.93 (d, J=2.2 Hz, 1H), 6.65 (dd, J=8.6, 2.3 Hz, 1H), 5.25 (br s, 2H). MS (EI): m/z 500 (M+H).

Example 449

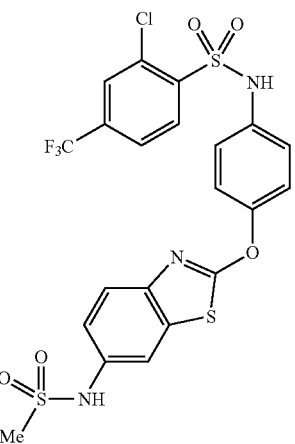

449

2-Chloro-N-[4-(6-methanesulfonylamino-benzothiazol-2-yloxy)-phenyl]-4-trifluoromethyl-benzenesulfonamide (449). 2-Chloro-N-[4-(6-methanesulfonylamino-benzothiazol-2-yloxy)-phenyl]-4-trifluoromethyl-benzenesulfonamide was synthesized from N-[4-(6-amino-benzothiazol-2-yloxy)-phenyl]-2-chloro-4-trifluoromethyl-benzenesulfonamide (448) and methanesulfonyl chloride (Aldrich) in a similar manner as described in Examples 70-91. $^1$H NMR (400 MHz, DMSO-$d_6$) δ 11.07 (s, 1H), 9.82 (s, 1H), 8.26 (d, J=8.2 Hz, 1H), 8.16 (d, J=1.1 Hz, 1H), 7.95 (dd, J=8.3, 1.2 Hz, 1H), 7.75 (d, J=2.2 Hz, 1H), 7.62 (d, J=8.7 Hz, 1H), 7.37-7.34 (m, 2H), 7.24 (dd, J=8.7, 2.2 Hz, 1H), 7.23-7.19 (m, 2H). MS (EI): m/z 576 (M−H).

Example 450

2-Chloro-N-[4-(6-chloro-benzothiazol-2-yloxy)-phenyl]-4-trifluoromethyl-benzenesulfonamide (450). $^1$H NMR (400 MHz, DMSO-$d_6$) 11.10 (s, 1H), 8.27 (d, J=8.2 Hz, 1H), 8.17 (s, 1H), 8.07 (d, J=2.2 Hz, 1H), 7.96 (dd, J=8.3, 1.2 Hz, 1H), 7.65 (d, J=8.7 Hz, 1H), 7.44 (dd, J=8.6, 2.2 Hz, 1H), 7.40-7.35 (m, 2H), 7.23-7.19 (m, 2H). MS (EI): m/z 517 (M−H).

Example 451

2-Chloro-N-[4-(6-methoxy-benzothiazol-2-yloxy)phenyl]-4-trifluoromethyl-benzenesulfonamide (451). $^1$H NMR (400 MHz, DMSO-$d_6$) δ 11.06 (s, 1H), 8.26 (d, J=8.2 Hz, 1H), 8.16 (d, J=1.2 Hz, 1H), 7.95 (dd, J=8.3, 1.2 Hz, 1H), 7.55 (d, J=8.9 Hz, 1H), 7.52 (d, J=2.6 Hz, 1H), 7.36-7.32 (m, 2H), 7.22-7.17 (m, 2H), 7.00 (dd, J=8.9, 2.7 Hz, 1H), 3.77 (s, 3H). MS (EI): m/z 513 (M−H).

Example 452

2-Chloro-N-[4-(4-methoxy-benzothiazol-2-yloxy)-phenyl]-4-trifluoromethyl-benzenesulfonamide (452). $^1$H NMR (400 MHz, DMSO-$d_6$) δ 11.07 (s, 1H), 8.26 (d, J=8.2 Hz, 1H), 8.16 (d, J=1.2 Hz, 1H), 7.95 (dd, J=8.3, 1.3 Hz, 1H), 7.45 (dd, J=8.0, 0.8 Hz, 1H), 7.36-7.31 (m, 2H), 7.27 (t, J=8.1 Hz, 1H), 7.23-7.18 (m, 2H), 6.99 (dd, J=8.1, 0.6 Hz, 1H), 3.83 (s, 3H). MS (EI): m/z 513 (M−H).

Example 453

2-Chloro-N-[4-(6-trifluoromethyl-benzothiazol-2-yloxy)-phenyl]-4-trifluoromethyl-benzenesulfonamide (453). $^1$H NMR (400 MHz, DMSO-$d_6$) δ 11.12 (s, 1H), 8.44 (s, 1H), 8.28 (d, J=8.3 Hz, 1H), 8.17 (d, J=0.9 Hz, 1H), 7.96 (dd, J=8.3, 1.2 Hz, 1H), 7.84 (d, J=8.5 Hz, 1H), 7.73 (dd, J=8.6, 1.8 Hz, 1H), 7.43-7.37 (m, 2H), 7.26-7.20 (m, 2H). MS (EI): m/z 551 (M−H).

Example 454

2-Chloro-N-[4-(6-cyano-benzothiazol-2-yloxy)-phenyl]-4-trifluoromethyl-benzenesulfonamide (454). $^1$H NMR (400 MHz, DMSO-$d_6$) δ 11.13 (s, 1H), 8.50 (d, J=1.5 Hz, 1H), 8.28 (d, J=8.2 Hz, 1H), 8.17 (d, J=0.9 Hz, 1H), 7.96 (dd, J=8.3, 1.0 Hz, 1H), 7.84 (dd, J=8.5, 1.6 Hz, 1H), 7.81 (d, J=8.5 Hz, 1H), 7.43-7.37 (m, 2H), 7.26-7.20 (m, 2H). MS (EI): m/z 508 (M−H).

Example 455

2-Chloro-N-[3,5-dichloro-4-(5-nitro-benzothiazol-2-yloxy)phenyl]-4-trifluoromethyl-benzenesulfonamide (455). $^1$H NMR (400 MHz, DMSO-$d_6$) δ 11.66 (s, 1H), 8.48 (d, J=1.8 Hz, 1H), 8.30 (d, J=8.9 Hz, 1H), 8.25-8.20 (m, 2H), 8.22 (s, 1H), 8.01 (d, J=8.2 Hz, 1H), 7.33 (s, 2H). MS (EI): m/z 596 (M−H).

Example 456

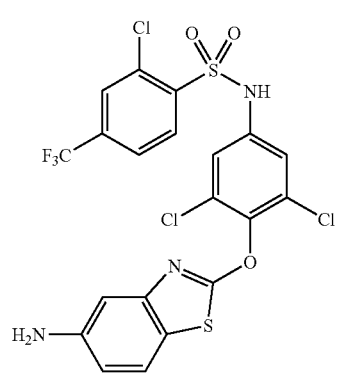

N-[4-(5-Amino-benzothiazol-2-yloxy)-3,5-dichloro-phenyl]-2-chloro-4-trifluoromethyl-benzenesulfonamide (456). N-[4-(5-Amino-benzothiazol-2-yloxy)-3,5-dichloro-phenyl]-2-chloro-4-trifluoromethyl-benzenesulfonamide was synthesized from 2-chloro-N-[3,5-dichloro-4-(5-nitro-benzothiazol-2-yloxy)-phenyl]-4-trifluoromethyl-benzenesulfonamide (455) in a similar manner as described in Examples 16-23 (Method A). $^1$H NMR (400 MHz, DMSO-$d_6$) δ 8.37 (d, J=8.2 Hz, 1H), 8.19 (s, 1H), 8.00 (dd, J=8.3, 1.1 Hz, 1H), 7.49 (d, J=8.6 Hz, 1H), 7.30 (s, 2H), 6.77 (d, J=2.1 Hz, 1H), 6.63 (dd, J=8.6, 2.1 Hz, 1H). MS (EI): m/z 568 (M+H).

Example 457

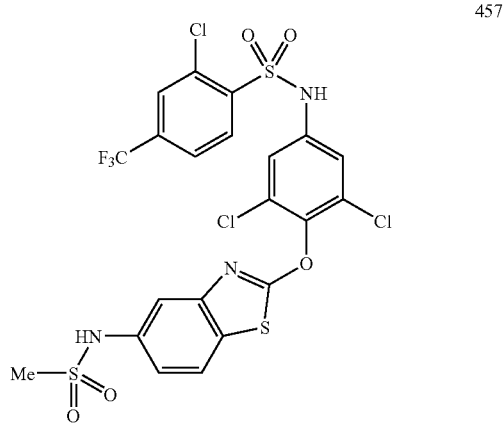

2-Chloro-N-[3,5-dichloro-4-(5-methanesulfonylamino-benzothiazol-2-yloxy)-phenyl]-4-trifluoromethyl-benzenesulfonamide (457). 2-Chloro-N-[3,5-dichloro-4-(5-methanesulfonylamino-benzothiazol-2-yloxy)-phenyl]-4-trifluoromethyl-benzenesulfonamide was synthesized from N-[4-(5-Amino-benzothiazol-2-yloxy)-3,5-dichloro-phenyl]-2-chloro-4-trifluoromethyl-benzenesulfonamide (456) and methanesulfonyl chloride (Aldrich) in a similar manner as described in Examples 70-91. $^1$H NMR (400 MHz, DMSO-$d_6$) δ 11.63 (s, 1H), 9.87 (s, 1H), 8.38 (d, J=8.3 Hz, 1H), 8.20 (s, 1H), 8.00 (d, J=8.3 Hz, 1H), 7.91 (d, J=8.6 Hz, 1H), 7.44 (d, J=1.7 Hz, 1H), 7.32 (s, 2H), 7.21 (dd, J=8.7, 1.6 Hz, 1H). MS (EI): m/z 644 (M−H).

Example 458

2-Chloro-N-[3,5-dichloro-4-(5-methanesulfonyl-benzothiazol-2-yloxy)-phenyl]-4-trifluoromethyl-benzenesulfonamide (458). $^1$H NMR (400 MHz, DMSO-$d_6$) δ 11.65 (s, 1H), 8.38 (d, J=8.2 Hz, 1H), 8.29 (d, J=8.4 Hz, 1H), 8.22 (s, 1H), 8.19 (d, J=1.6 Hz, 1H), 8.01 (dd, J=8.2, 1.0 Hz, 1H), 7.88 (dd, J=8.5, 1.7 Hz, 1H), 7.34 (s, 2H), 3.24 (s, 3H). MS (EI): m/z 629 (M−H).

Example 459

N-[4-(6-Acetyl-benzothiazol-2-yloxy)-3,5-dichloro-phenyl]-2-chloro-4-trifluoromethyl-benzenesulfonamide (459). $^1$H NMR (400 MHz, DMSO-$d_6$) δ 11.62 (s, 1H), 8.68 (d, J=1.7 Hz, 1H), 8.38 (d, J=8.2 Hz, 1H), 8.21 (s, 1H), 8.02-7.97 (m, 2H), 7.76 (d, J=8.5 Hz, 1H), 7.32 (s, 2H), 2.61 (s, 3H). MS (EI): m/z 629 (M−H).

Example 501

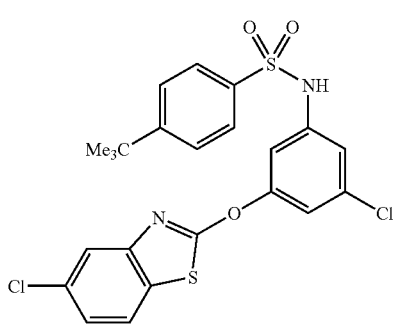

4-tert-Butyl-N-[3-chloro-5-(5-chloro-benzothiazole-2-yloxy)]-benzenesulfonamide (501). 4-tert-Butyl-N-[3-chloro-5-(5-chloro-benzothiazole-2-yloxy)]-benzenesulfonamide was synthesized (62%) from aniline 273 using Method D described in Examples 70-91. $^1$H NMR (400 MHz, DMSO-d$_6$) δ 10.9 (s, 1H), 8.3 (d, J=8.6 Hz, 1H), 7.82 (d, J=2.1 Hz, 1H), 7.78 (d, J=8.5 Hz, 2H), 7.63 (d, J=8.5 Hz, 2H), 7.45 (dd, J=8.6, 2.1 Hz, 1H), 7.38 (dd, J=1.9, 1.9 Hz, 1H), 7.16 (dd, J=1.9, 1.9 Hz, 1H), 7.12 (dd, J=1.8, 1.8 Hz, 1H), 1.3 (s, 9H). MS (EI): m/z 505 (100, M–H), 506 (33, M–H), 507 (94, M–H), 508 (30, M–H), 509 (15, M–H).

Example 502

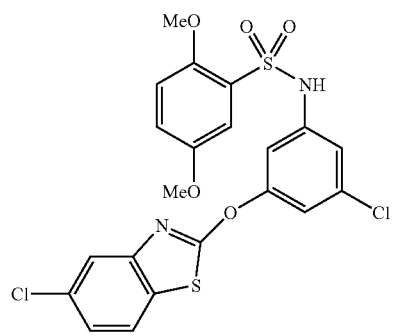

N-[3-Chloro-5-(5-chloro-benzothiazole-2-yloxy)-phenyl]-2,5-dimethoxybenzenesulfonamide (502). N-[3-Chloro-5-(5-chloro-benzothiazole-2-yloxy)-phenyl]-2,5-dimethoxybenzenesulfonamide was synthesized (55%) from aniline 273 using Method D described in Examples 70-91. $^1$H NMR (400 MHz, DMSO-d$_6$) δ 10.8 (s, 1H), 8.1 (d, J=8.6 Hz, 1H), 7.8 (d, J=2.1 Hz, 1H), 7.45 (dd, J=8.6, 2.1 Hz, 2H), 7.34-7.28 (m, 2H), 7.23 (dd, J=9.0, 3.0 Hz, 1H), 7.18 (d, J=9.1 Hz, 1H), 7.15-7.1 (m, 2H), 3.9 (s, 3H), 3.6 (s, 3H). MS (EI): m/z 509 (100, M–H), 510 (28, M–H), 511 (64, M–H), 512 (22, M–H), 513 (18, M–H).

Example 503

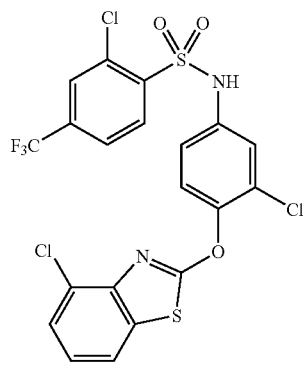

2-Chloro-N-[3-chloro-4-(4-chloro-benzothiazol-2-oxy)-phenyl]-4-trifluoromethylbenzenesulfonamide (503). 2-Chloro-N-[3-chloro-4-(4-chloro-benzothiazol-2-oxy)-phenyl]-4-trifluoromethylbenzenesulfonamide was synthesized (84%) in a similar manner as described in Example 424. $^1$H NMR (400 MHz, DMSO-d$_6$) δ 11.4 (s, 1H), 8.33 (d, J=8.9 Hz, 1H), 8.2 (s, 1H), 7.99 (d, J=8.3, Hz, 2H), 7.93 (d, J=8.0 Hz, 1H), 7.62 (d, J=9.0, Hz, 1H), 7.54 (d, J=8.0 Hz, 1H), 7.39-7.32 (m, 2H), 7.22 (dd, J=9.0, 2.5 Hz, 1H). MS (EI): m/z 551 (92, M–H), 552 (23, M–H), 553 (100, M–H), 554 (25, M–H), 555 (40, M–H).

Example 504

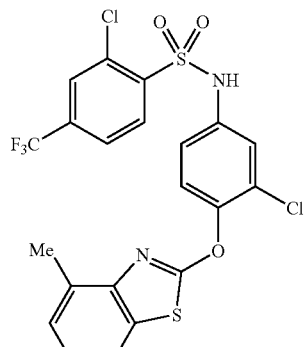

2-Chloro-N-[3-chloro-4-(4-methyl-benzothiazol-2-oxy)-phenyl]-4-trifluoromethylbenzenesulfonamide (504). 2-Chloro-N-[3-chloro-4-(4-methyl-benzothiazol-2-oxy)-phenyl]-4-trifluoromethylbenzenesulfonamide was synthesized (45%) from phenol 422 in a similar manner as described in Example 438. $^1$H NMR (400 MHz, DMSO-d$_6$) δ 11.4 (s, 1H), 8.33 (d, J=8.2 Hz, 1H), 8.2 (s, 1H), 7.99 (d, J=8.3, Hz, 1H), 7.73 (dd, J=7.2, 1.9 Hz, 1H), 7.6 (d, J=8.9 Hz, 1H), 7.35 (d, J=2.6 Hz, 1H), 7.3-7.28 (m, 1H), 7.25 (d, J=7.4, Hz, 1H), 7.2 (d, J=8.4, 2.6 Hz, 1H), 2.35 (s, 3H). MS (EI): m/z 531 (100, M–H), 532 (28, M–H), 533 (75, M–H), 534 (16, M–H), 535 (15, M–H).

Example 505

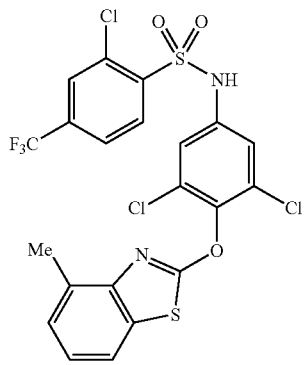

2-Chloro-N-[3,5-dichloro-4-(4-methyl-benzothiazol-2-oxy)-phenyl]-4-trifluoromethylbenzenesulfonamide (505). 2-Chloro-N-[3,5-dichloro-4-(4-methyl-benzothiazol-2-oxy)-phenyl]-4-trifluoromethylbenzenesulfonamide was synthesized (16%) from phenol 421 in a similar manner as described in Example 438. $^1$H NMR (400 MHz, DMSO-d$_6$) δ 11.6 (s, 1H), 8.38 (d, J=8.3 Hz, 1H), 8.22 (s, 1H), 8.0 (d, J=8.3, Hz, 1H), 7.76 (dd, J=9.0, 2.9 Hz, 1H), 7.34 (s, 2H), 7.28-7.22 (m, 2H), 2.35 (s, 3H). MS (EI): m/z 565 (100, M–H), 566 (28, M–H), 567 (75, M–H), 568 (16, M–H), 569 (15, M–H).

Example 600

Using methods similar to Lehmann, et al., ibid., selected compounds exhibited the following IC$_{50}$ values in a PPARγ ligand binding assay utilizing [$^3$H]—BRL 49653 as the radioligand. IC$_{50}$ values are defined as the concentration of test compounds required to reduce by 50% the specific binding of [$^3$H]—BRL 49653 and are represented by (+) <30 μM; (++) <10 μM; (+++) <1 μM.

TABLE 20

| Compound | PPARγ Binding IC$_{50}$ |
| --- | --- |
| 3 | +++ |
| 4.1 | +++ |
| 4.2 | +++ |
| 4.3 | +++ |
| 5.2 | +++ |
| 5.3 | ++ |
| 40 | +++ |
| 41 | ++ |
| 42 | +++ |
| 43 | +++ |
| 44 | +++ |
| 45 | +++ |
| 46 | +++ |
| 47 | +++ |
| 48 | +++ |
| 49 | +++ |
| 50 | +++ |
| 71 | +++ |
| 72 | +++ |
| 73 | +++ |
| 74 | +++ |
| 75 | +++ |
| 76 | ++ |
| 77 | ++ |
| 78 | +++ |
| 79 | +++ |

TABLE 20-continued

| Compound | PPARγ Binding IC$_{50}$ |
| --- | --- |
| 80 | +++ |
| 81 | +++ |
| 82 | +++ |
| 83 | +++ |
| 84 | +++ |
| 85 | +++ |
| 86 | +++ |
| 87 | +++ |
| 88 | +++ |
| 89 | +++ |
| 90 | +++ |
| 91 | +++ |
| 103 | +++ |
| 104 | ++ |
| 106 | +++ |
| 224 | +++ |
| 225 | +++ |
| 226 | +++ |
| 231 | +++ |
| 232 | +++ |
| 237 | +++ |
| 238 | +++ |
| 283 | ++ |
| 284 | +++ |
| 285 | +++ |
| 286 | ++ |
| 287 | +++ |
| 288 | +++ |
| 289 | +++ |
| 290 | + |
| 291 | + |
| 292 | ++ |
| 293 | +++ |
| 294 | + |
| 295 | ++ |
| 296 | ++ |
| 297 | ++ |
| 298 | +++ |
| 299 | +++ |
| 300 | +++ |
| 301 | +++ |
| 302 | +++ |
| 303 | +++ |
| 304 | +++ |
| 305 | +++ |
| 306 | +++ |
| 307 | ++ |
| 308 | +++ |
| 309 | +++ |
| 310 | +++ |
| 311 | +++ |
| 322 | ++ |
| 323 | ++ |
| 324 | +++ |
| 331 | +++ |
| 332 | +++ |
| 333 | +++ |
| 424 | ++ |
| 424 | ++ |
| 425 | ++ |
| 425 | ++ |
| 426 | +++ |
| 426 | +++ |
| 427 | +++ |
| 427 | +++ |
| 428 | +++ |
| 428 | +++ |
| 429 | +++ |
| 429 | +++ |
| 433 | +++ |
| 434 | ++ |
| 435 | +++ |
| 436 | ++ |
| 438 | +++ |
| 440 | +++ |
| 441 | +++ |
| 442 | +++ |
| 444 | +++ |

TABLE 20-continued

| Compound | PPARγ Binding IC$_{50}$ |
|---|---|
| 445 | +++ |
| 455 | ++ |
| 457 | +++ |
| 458 | +++ |
| 501 | − |
| 502 | − |
| 503 | + |
| 504 | + |
| 505 | + |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a metabolic disorder comprising administering to a subject having the metabolic disorder a therapeutically effective amount of a compound having the formula:

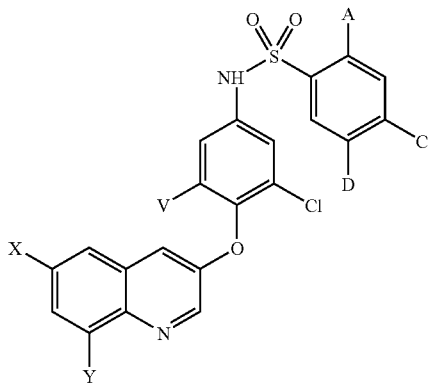

wherein
A is Cl or CF$_3$;
C is Cl or CF$_3$;
D is H or CH$_3$;
V is F or Cl;
X is a member selected from the group consisting of H, CH$_3$, COOH, and CO$_2$CH$_3$; and
Y is a member selected from the group consisting of H, CO$_2$H and CO$_2$CH$_3$;
or a pharmaceutically acceptable salt thereof;
wherein the metabolic disorder is selected from the group consisting of diabetes, obesity, hypercholesterolemia, hyperlipidemia, dyslipidemia, hypertriglylceridemia, hyperglycemia, insulin resistance and hyperinsulinemia.

2. The method of claim 1, wherein the subject is a human.

3. The method of claim 1, wherein the administration is oral.

4. The method of claim 1, wherein the administration is parenteral.

5. The method of claim 1, wherein the administration is topical.

6. The method of claim 1, wherein the metabolic disorder is mediated by PPARγ.

7. The method of claim 1, wherein the compound is admininistered in the form of a pharmaceutical composition comprising the compound, or a pharmaceutically acceptable salt thereof, and a pharmaceutically acceptable carrier or excipient.

8. The method of claim 7, wherein the compound is in a unit dosage form.

9. The method of claim 8, wherein the unit dosage form is a packaged preparation.

10. The method of claim 7, wherein the pharmaceutical composition is a tablet, capsule, power, cachet, or lozenge.

11. The method of claim 7, wherein the amount of the compound in the pharmaceutical composition is about 0.1 mg to about 100 mg.

12. The method of claim 11, wherein the amount of the compound in the pharmaceutical composition is about 1.0 mg to about 100 mg.

13. The method of claim 8, wherein the unit dosage form contains about 5% of the compound.

14. The method of claim 1, wherein the compound is administered as a daily dose.

15. The method of claim 1, wherein about 0.001 mg/kg to about 10 mg/kg of the compound is administered to the subject.

16. The method of claim 15, wherein about 0.1 mg/kg to about 10 mg/kg of the compound is administered to the subject.

* * * * *

UNITED STATES PATENT AND TRADEMARK OFFICE
CERTIFICATE OF CORRECTION

| | | |
|---|---|---|
| PATENT NO. | : 7,960,408 B2 | Page 1 of 1 |
| APPLICATION NO. | : 12/372699 | |
| DATED | : June 14, 2011 | |
| INVENTOR(S) | : McGee et al. | |

It is certified that error appears in the above-identified patent and that said Letters Patent is hereby corrected as shown below:

Title Page;

On page 1 of the patent, left column, in item (73) "Assignee," replace "Amgen Inc., Thousand Oaks, CA (US)" with -- Amgen Inc., Thousand Oaks, CA (US) and Japan Tobacco, Inc., Tokyo (JP) --.

Signed and Sealed this
Twenty-third Day of August, 2011

David J. Kappos
*Director of the United States Patent and Trademark Office*